(12) United States Patent
Chain

(10) Patent No.: US 8,703,137 B2
(45) Date of Patent: Apr. 22, 2014

(54) TREATMENT OF TAUOPATHIES

(75) Inventor: Daniel G. Chain, New York, NY (US)

(73) Assignee: Intellect Neurosciences Inc., New York, NY (US)

(*) Notice: Subject to any disclaimer, the term of this patent is extended or adjusted under 35 U.S.C. 154(b) by 0 days.

(21) Appl. No.: 13/363,214

(22) Filed: Jan. 31, 2012

(65) Prior Publication Data

US 2012/0244146 A1  Sep. 27, 2012

Related U.S. Application Data

(60) Provisional application No. 61/438,083, filed on Jan. 31, 2011.

(51) Int. Cl.
*A61K 39/00* (2006.01)
*A61K 39/395* (2006.01)

(52) U.S. Cl.
USPC ............... 424/139.1; 424/133.1; 424/141.1; 514/17.7; 514/17.8

(58) Field of Classification Search
None
See application file for complete search history.

(56) References Cited

U.S. PATENT DOCUMENTS

| | | | |
|---|---|---|---|
| 3,955,137 A | 5/1976 | Harrington et al. | |
| 3,978,797 A | 9/1976 | Harrington et al. | |
| 4,092,603 A | 5/1978 | Harrington | |
| 4,166,817 A | 9/1979 | Ferres et al. | |
| 5,492,812 A | 2/1996 | Voohies | |
| 6,232,437 B1 | 5/2001 | Vandermeeren et al. | |
| 6,376,205 B1 | 4/2002 | Wischik et al. | |
| 6,762,179 B2 | 7/2004 | Cochran et al. | |
| 6,953,794 B2 | 10/2005 | Wischik et al. | |
| 7,238,788 B2 | 7/2007 | Lee | |
| 7,256,190 B2 | 8/2007 | Cochran et al. | |
| 7,335,505 B2 | 2/2008 | Wischik et al. | |
| 7,335,652 B2 | 2/2008 | Wischik et al. | |
| 7,488,727 B2 | 2/2009 | Cochran et al. | |
| 7,534,786 B2 | 5/2009 | Wischik et al. | |
| 7,605,179 B2 | 10/2009 | Wischik et al. | |
| 7,713,962 B2 | 5/2010 | Wischik et al. | |
| 7,737,138 B2 | 6/2010 | Wischik et al. | |
| 7,790,881 B2 | 9/2010 | Storey et al. | |
| 7,834,237 B2 | 11/2010 | Wischik et al. | |
| 7,901,689 B2 | 3/2011 | Chain | |
| 8,012,936 B2 | 9/2011 | Sigurdsson et al. | |
| 8,173,127 B2 | 5/2012 | Chain | |
| 2004/0078835 A1 | 4/2004 | Wischik et al. | |
| 2004/0082763 A1 | 4/2004 | Novak | |
| 2006/0088548 A1 | 4/2006 | Chain | |
| 2006/0167227 A1 | 7/2006 | Kontsekova | |
| 2008/0050383 A1 | 2/2008 | Sigurdsson et al. | |
| 2008/0207603 A1 | 8/2008 | Storey et al. | |
| 2008/0207604 A1 | 8/2008 | Wischik et al. | |
| 2008/0219929 A1 | 9/2008 | Wischik et al. | |
| 2009/0054419 A1 | 2/2009 | Wischik et al. | |
| 2009/0075984 A1 | 3/2009 | Wischik et al. | |
| 2009/0123936 A1 | 5/2009 | Novak | |
| 2009/0209526 A1 | 8/2009 | Wischik et al. | |
| 2010/0280975 A1 | 11/2010 | Wischik et al. | |
| 2010/0285605 A1 | 11/2010 | Wischik et al. | |
| 2010/0290986 A1 | 11/2010 | Wischik et al. | |
| 2010/0316564 A1 | 12/2010 | Sigurdsson | |
| 2011/0142824 A1 | 6/2011 | Burbridge et al. | |
| 2011/0177109 A1 | 7/2011 | Smith, III et al. | |
| 2012/0087861 A1 | 4/2012 | Nitsch et al. | |
| 2012/0244159 A1 | 9/2012 | Chain | |

FOREIGN PATENT DOCUMENTS

WO  WO 2012/045882  4/2012
WO  WO 2012/149365  11/2012

OTHER PUBLICATIONS

Basurto-Islas et al. 2008 "Accumulation of Aspartic acid 421 and glutamic acid 391 cleaved tau in neurofibrillary tangles correlates with progressoin in alzheimer's disease" J neuropathol Exp Neurol 67(5):470-483.*
Panza et al. 2009 "Beyond the neurotransmitter-focused approach in treating Alzheimer's disease: drugs targeting beta-amyloid and tau protein" Aging Clin Exp Res 21(6): abstract.*
Rafii and Aisen 2009 "Recent developments in Alzheimer's disease therapeutics" BMC Medicine 7(7):1-4.*
International Search Report issued on Aug. 17, 2012, in connection with International Application PCT/US2012/023375.
Written Opinion of the International Searching Authority issued on Aug. 17, 2012, in connection with International Application PCT/US2012/023375.
Sengupta et al., "Degradation of Tau Protein by Puromycin-Sensitive Aminopeptidase in Vitro", Biochemistry, Nov. 24, 2006, vol. 45, pp. 15111-15119.
Gamblin et al., "Caspase cleavage of tau: Linking amyloid and neurofibrillary tangles in Alzheimer's disease", Proceedings of the National Academy of Sciences, Aug. 19, 2003,vol. 100, No. 17, pp. 10032-10037.
Yamamoto et al., "Phosphorylation of tau at serine 416 by Ca2+/calmodulin-dependent protein kinase II in neuronal soma in brain", Journal of Neurochemistry, Jul. 5, 2005, vol. 94, pp. 1438-1447.
Vestergaard et al., "Detection of Alzheimer's tau protein using localised surface plasmon resonance-based immunochip", Talanta, Jun. 17 ,2007 ,vol. 74, pp. 1039-1042.

(Continued)

*Primary Examiner* — Jeffrey Stucker
*Assistant Examiner* — Adam M Weidner
(74) *Attorney, Agent, or Firm* — Davidson, Davidson & Kappel, LLC

(57) ABSTRACT

The invention is directed to methods of treatment of Alzheimer's disease and other tauopathies, via the administration of antibodies having specificity to abnormal forms of tau protein, the antibodies showing no binding and/or reactivity to a normal tau protein and being administered under conditions and in amounts effective to prevent or treat Alzheimer's disease or other tauopathies. In certain embodiments, the antibodies are selective for soluble truncated tau protein truncated at (i) its C-terminus after the glutamic acid residue Glu391, or (ii) at the aspartic acid residue Asp421, or (iii) at its N-terminus at the aspartic acid residue Asp13, or (iv) a combination of (i)-(iii). Further aspects of the invention are directed to the administration of an immunogen comprising an abnormal tau, preferably a soluble truncated tau.

44 Claims, 1 Drawing Sheet

(56) References Cited

OTHER PUBLICATIONS

Lars M. Ittner et al., "Amlyiod-B and tau—a toxic pas de deux in Alzheimer's disease", Nature Reviews, NeuroScience, Feb. 2011, vol. 12.

Marc Dhenain, "Preclinical evaluation of anti-amyloid and anti-Tau therapies by RECALL-VAX technology", RECALL-VAX Technology, 2012.

Alix de Calignon et al., "Caspase activation precedes and leads to tangles", vol. 464: 12, Apr. 2, 2010.

B. Kovacech et al., Tau Truncation in a productive Pottranslational Modification of Neurofibrillary Degeneration in Alzheimer's Disease, Current Alzheimer's Research, 2010, pp. 708-716.

Robert A. Rissman et al., "Caspase-cleavage of tau is an early event in Alzheimer disease tangle pathology", The Journal of Clinical Investigation, Jul. 2001, vol. 114, pp. 115-130.

Khurana V, Elson-Schwab I, Fulga TA, Sharp KA, Loewen CA, et al.. Lysosomal Dysfunction Promotes Cleavage and Neurotoxicity of Tau In Vivo. PLoS Genet 6(7): e1001026. doi:10.1371/journal.pgen. 1001026, (2010).

Peleg M. Horowitz et al., Early Changes and Capase-6 Cleavage of Tau in Alzheimers Disease, The Journal of Neuroscience, Sep. 8, 2004, vol. 24(36) pp. 7895-7902.

Patrice Delobel et al, "Analysis of Tau Phosphorylation and Truncation in a Mouse Model of Human Tauopathy", Molecular Pathogenesis of Genetic and Inherited Diseases; The American Journal of Pathology, vol. 172, Jan. 2008. pp. 123-131.

Ayodeji A. Asuni et al., "Immunotherapy Targeting Pathological Tau Conformers in a Tangle Mouse Model Reduces Brain Pathology with Associated Functional Improvements", Neurobiology of Disease, The Journal of Neuroscience, Aug. 22, 2007, vol. 27(34), pp. 9115-9129.

Einar M. Sigurdsson, "Tau-Focused Immunotherapy for Alzheimers Disease and Related Tauopathies", Current Alzheimer Research, Jun. 2009, pp. 446-450.

Einar M.Sigurdsson, "Immunotherapy Tageting Pathological Tau Protein in Aizheimers Disease and Related Tauopathies", journal of Alzheirners Disease 15, 2008, pp. 157-168.

Qipeng Zhang et al., Truncated tau at D421 is associated with neurodegeneration and tangle formation in the brain of Alzheimer transgenic models, Acta Neuropathol , 2009. vol. 117, pp. 687-697.

Invitrogen, "Mouse (monoclonal) Anti-tau (421/422) Cleavage Site Specific Antibody, Unconjugated", Product Analysis Sheet. Catalog No. AHB0061, (2010).

Millipore, Anti-cleaved-Tau (Asp421), clone C3, Uniprot No. P10636, Jan. 16, 2011, http://www.millipore.com/catalogue/item/36-017.

Allal Boutajangout et al., Immunotherapy targeting pathological tau prevents cognitive decline in a new tangle mouse model, Journal Section: Neurobiology of Disease, (2010).

International Preliminary Report of Patentability issued on Aug. 6, 2013, in connection with International Application No. PCT/US2012/023375.

* cited by examiner

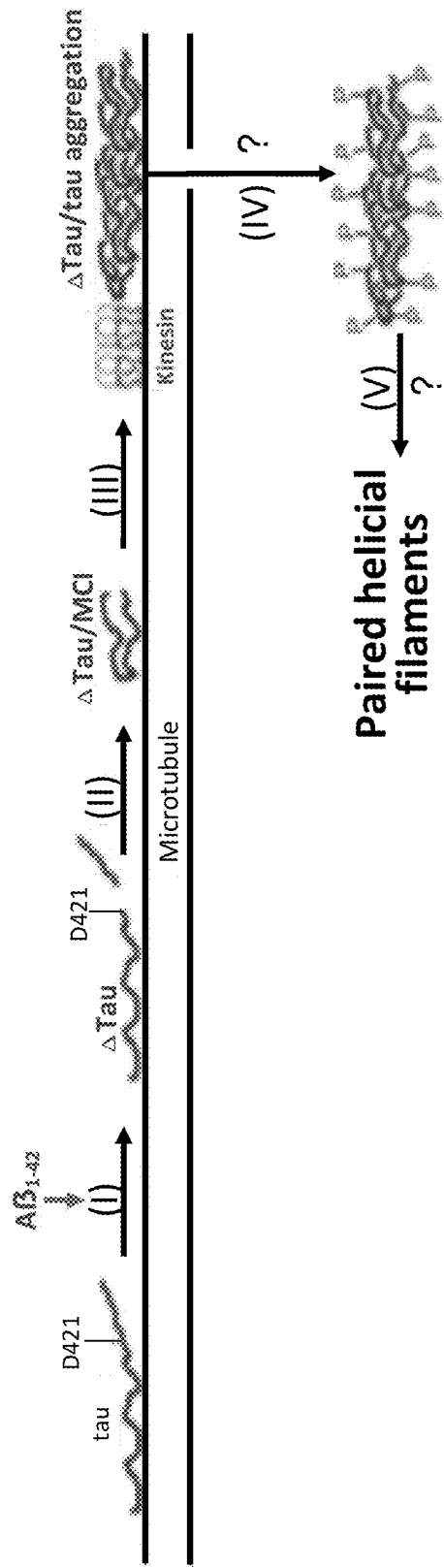

SEQUENCE LISTING

```
<160> NUMBER OF SEQ ID NOS: 117

<210> SEQ ID NO 1
<211> LENGTH: 441
<212> TYPE: PRT
<213> ORGANISM: Artificial Sequence
<220> FEATURE:
<223> OTHER INFORMATION: HTAU40

<400> SEQUENCE: 1

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
                20                  25                  30

Gln Asp Gln Glu Gly Asp Thr Asp Ala Gly Leu Lys Glu Ser Pro Leu
            35                  40                  45

Gln Thr Pro Thr Glu Asp Gly Ser Glu Glu Pro Gly Ser Glu Thr Ser
        50                  55                  60

Asp Ala Lys Ser Thr Pro Thr Ala Glu Asp Val Thr Ala Pro Leu Val
65                  70                  75                  80

Asp Glu Gly Ala Pro Gly Lys Gln Ala Ala Gln Pro His Thr Glu
                85                  90                  95

Ile Pro Glu Gly Thr Thr Ala Glu Glu Ala Gly Ile Gly Asp Thr Pro
            100                 105                 110

Ser Leu Glu Asp Glu Ala Ala Gly His Val Thr Gln Ala Arg Met Val
        115                 120                 125

Ser Lys Ser Lys Asp Gly Thr Gly Ser Asp Asp Lys Lys Ala Lys Gly
    130                 135                 140

Ala Asp Gly Lys Thr Lys Ile Ala Thr Pro Arg Gly Ala Ala Pro Pro
145                 150                 155                 160

Gly Gln Lys Gly Gln Ala Asn Ala Thr Arg Ile Pro Ala Lys Thr Pro
                165                 170                 175

Pro Ala Pro Lys Thr Pro Pro Ser Ser Gly Glu Pro Pro Lys Ser Gly
            180                 185                 190

Asp Arg Ser Gly Tyr Ser Ser Pro Gly Ser Pro Gly Thr Pro Gly Ser
        195                 200                 205

Arg Ser Arg Thr Pro Ser Leu Pro Thr Pro Pro Thr Arg Glu Pro Lys
    210                 215                 220

Lys Val Ala Val Val Arg Thr Pro Pro Lys Ser Pro Ser Ser Ala Lys
225                 230                 235                 240

Ser Arg Leu Gln Thr Ala Pro Val Pro Met Pro Asp Leu Lys Asn Val
                245                 250                 255

Lys Ser Lys Ile Gly Ser Thr Glu Asn Leu Lys His Gln Pro Gly Gly
            260                 265                 270

Gly Lys Val Gln Ile Ile Asn Lys Lys Leu Asp Leu Ser Asn Val Gln
        275                 280                 285
```

```
Ser Lys Cys Gly Ser Lys Asp Asn Ile Lys His Val Pro Gly Gly Gly
    290                 295                 300
Ser Val Gln Ile Val Tyr Lys Pro Val Asp Leu Ser Lys Val Thr Ser
305                 310                 315                 320
Lys Cys Gly Ser Leu Gly Asn Ile His His Lys Pro Gly Gly Gly Gln
                325                 330                 335
Val Glu Val Lys Ser Glu Lys Leu Asp Phe Lys Asp Arg Val Gln Ser
            340                 345                 350
Lys Ile Gly Ser Leu Asp Asn Ile Thr His Val Pro Gly Gly Gly Asn
        355                 360                 365
Lys Lys Ile Glu Thr His Lys Leu Thr Phe Arg Glu Asn Ala Lys Ala
370                 375                 380
Lys Thr Asp His Gly Ala Glu Ile Val Tyr Lys Ser Pro Val Val Ser
385                 390                 395                 400
Gly Asp Thr Ser Pro Arg His Leu Ser Asn Val Ser Ser Thr Gly Ser
                405                 410                 415
Ile Asp Met Val Asp Ser Pro Gln Leu Ala Thr Leu Ala Asp Glu Val
            420                 425                 430
Ser Ala Ser Leu Ala Lys Gln Gly Leu
        435                 440

<210> SEQ ID NO 2
<211> LENGTH: 410
<212> TYPE: PRT
<213> ORGANISM: Artificial
<220> FEATURE:
<223> OTHER INFORMATION: Human Tau 2N3R

<400> SEQUENCE: 2

Met Ala Glu Pro Arg Gln Glu Phe Glu Val Met Glu Asp His Ala Gly
1                   5                   10                  15
Thr Tyr Gly Leu Gly Asp Arg Lys Asp Gln Gly Gly Tyr Thr Met His
            20                  25                  30
Gln Asp Gln Glu Gly Asp Thr Asp Ala Gly Leu Lys Glu Ser Pro Leu
        35                  40                  45
Gln Thr Pro Thr Glu Asp Gly Ser Glu Glu Pro Gly Ser Glu Thr Ser
    50                  55                  60
Asp Ala Lys Ser Thr Pro Thr Ala Glu Asp Val Thr Ala Pro Leu Val
65                  70                  75                  80
Asp Glu Gly Ala Pro Gly Lys Gln Ala Ala Gln Pro His Thr Glu
                85                  90                  95
Ile Pro Glu Gly Thr Thr Ala Glu Glu Ala Gly Ile Gly Asp Thr Pro
            100                 105                 110
Ser Leu Glu Asp Glu Ala Ala Gly His Val Thr Gln Ala Arg Met Val
        115                 120                 125
Ser Lys Ser Leu Asp Gly Thr Gly Ser Asp Asp Lys Lys Ala Lys Gly
    130                 135                 140
Ala Asp Gly Lys Thr Lys Ile Ala Thr Pro Arg Gly Ala Ala Pro Pro
145                 150                 155                 160
Gly Gln Lys Gly Gln Ala Asn Ala Thr Arg Ile Pro Ala Lys Thr Pro
                165                 170                 175
Pro Ala Pro Lys Thr Pro Pro Ser Ser Gly Glu Pro Pro Lys Ser Gly
            180                 185                 190
Asp Arg Ser Gly Tyr Ser Ser Pro Gly Ser Pro Gly Thr Pro Gly Ser
        195                 200                 205
```

```
Arg Ser Arg Thr Pro Ser Leu Pro Thr Pro Thr Arg Glu Pro Lys
    210                 215                 220

Lys Val Ala Val Val Arg Thr Pro Pro Lys Ser Pro Ser Ser Ala Lys
225                 230                 235                 240

Ser Arg Leu Gln Thr Ala Pro Val Pro Met Pro Asp Leu Lys Asn Val
                245                 250                 255

Lys Ser Lys Ile Gly Ser Thr Glu Asn Leu Lys His Gln Pro Gly Gly
                260                 265                 270

Gly Lys Val Gln Ile Val Tyr Lys Pro Val Asp Leu Ser Lys Val Thr
            275                 280                 285

Ser Lys Cys Gly Ser Leu Gly Asn Ile His His Lys Pro Gly Gly Gly
290                 295                 300

Gln Val Glu Val Lys Ser Glu Lys Leu Asp Phe Lys Asp Arg Val Gln
305                 310                 315                 320

Ser Lys Ile Gly Ser Leu Asp Asn Ile Thr His Val Pro Gly Gly Gly
                325                 330                 335

Asn Lys Lys Ile Glu Thr His Lys Leu Thr Phe Arg Glu Asn Ala Lys
                340                 345                 350

Ala Lys Thr Asp His Gly Ala Glu Ile Val Tyr Lys Ser Pro Val Val
            355                 360                 365

Ser Gly Asp Thr Ser Pro Ala His Leu Ser Asn Val Ser Ser Thr Gly
370                 375                 380

Ser Ile Asp Met Val Asp Ser Pro Gln Leu Ala Thr Leu Ala Asp Glu
385                 390                 395                 400

Val Ser Ala Ser Leu Ala Lys Gln Gly Leu
                405                 410

<210> SEQ ID NO 3
<211> LENGTH: 412
<212> TYPE: PRT
<213> ORGANISM: Artificial Sequence
<220> FEATURE:
<223> OTHER INFORMATION: Human Tau 1N4R

<400> SEQUENCE: 3

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
            20                  25                  30

Gln Asp Gln Glu Gly Asp Thr Asp Ala Gly Leu Lys Glu Ser Pro Leu
        35                  40                  45

Gln Thr Pro Thr Gly Asp Gly Ser Glu Glu Pro Gly Ser Glu Thr Ser
    50                  55                  60

Asp Ala Lys Ser Thr Pro Thr Ala Glu Ala Glu Ala Gly Ile Gly
65                  70                  75                  80

Asp Thr Pro Ser Leu Glu Asp Glu Ala Ala Gly His Val Thr Gln Ala
                85                  90                  95

Arg Met Val Ser Lys Ser Leu Asp Gly Thr Gly Ser Asp Asp Lys Lys
            100                 105                 110

Ala Lys Gly Ala Asp Gly Lys Thr Leu Ile Ala Thr Pro Arg Gly Ala
        115                 120                 125

Ala Pro Pro Gly Gln Lys Gly Gln Ala Asn Ala Thr Arg Ile Pro Ala
    130                 135                 140

Lys Thr Pro Pro Ala Pro Lys Thr Pro Ser Ser Gly Glu Pro Pro
145                 150                 155                 160

Lys Ser Gly Asp Arg Ser Gly Tyr Ser Ser Pro Gly Ser Pro Gly Thr
```

```
                  165                 170                 175
Pro Gly Ser Arg Ser Arg Thr Pro Ser Leu Pro Thr Pro Pro Thr Arg
            180                 185                 190

Glu Pro Lys Lys Val Ala Val Val Arg Thr Pro Pro Lys Ser Pro Ser
        195                 200                 205

Ser Ala Lys Ser Arg Leu Gln Thr Ala Pro Val Pro Met Pro Asp Leu
    210                 215                 220

Lys Asn Val Lys Ser Lys Ile Gly Ser Thr Glu Asn Leu Lys His Gln
225                 230                 235                 240

Pro Gly Gly Gly Lys Val Gln Ile Ile Asn Lys Lys Leu Asp Leu Ser
                245                 250                 255

Asn Val Gln Ser Lys Cys Gly Ser Leu Asp Asn Ile Leu His Val Pro
            260                 265                 270

Gly Gly Gly Ser Val Gln Ile Val Tyr Lys Pro Val Asp Leu Ser Lys
        275                 280                 285

Val Thr Ser Lys Cys Gly Ser Leu Gly Asn Ile His His Lys Pro Gly
    290                 295                 300

Gly Gly Gln Val Glu Val Lys Ser Glu Lys Leu Asp Phe Lys Asp Arg
305                 310                 315                 320

Val Gln Ser Lys Ile Gly Ser Leu Asp Asn Ile Thr His Val Pro Gly
                325                 330                 335

Gly Gly Asn Lys Lys Ile Glu Thr His Lys Leu Thr Phe Arg Glu Asn
            340                 345                 350

Ala Lys Ala Lys Thr Asp His Gly Ala Glu Ile Val Tyr Lys Ser Pro
        355                 360                 365

Val Val Ser Gly Asp Thr Ser Pro Arg His Leu Ser Asn Val Ser Ser
    370                 375                 380

Thr Gly Ser Ile Asp Met Val Asp Ser Pro Gln Leu Ala Thr Leu Ala
385                 390                 395                 400

Asp Glu Val Ser Ala Ser Leu Ala Lys Gln Gly Leu
                405                 410

<210> SEQ ID NO 4
<211> LENGTH: 383
<212> TYPE: PRT
<213> ORGANISM: Artificial Sequence
<220> FEATURE:
<223> OTHER INFORMATION: Human Tau ON4R

<400> SEQUENCE: 4

Met Ala Glu Pro Arg Gln Glu Phe Glu Val Met Glu Asp His Ala Gly
1               5                   10                  15

Thr Tyr Gly Leu Gly Asp Arg Leu Asp Gln Gly Gly Tyr Thr Met His
            20                  25                  30

Gln Asp Gln Glu Gly Asp Thr Asp Ala Gly Leu Lys Ala Glu Glu Ala
        35                  40                  45

Gly Ile Gly Asp Thr Pro Ser Leu Glu Asp Glu Ala Ala Gly His Val
    50                  55                  60

Thr Gln Ala Arg Met Val Ser Lys Ser Lys Asp Gly Thr Gly Ser Asp
65                  70                  75                  80

Asp Lys Lys Ala Lys Gly Ala Asp Gly Lys Thr Lys Ile Ala Thr Pro
                85                  90                  95

Arg Gly Ala Ala Pro Pro Gly Gln Lys Gly Gln Ala Asn Ala Thr Arg
            100                 105                 110

Ile Pro Ala Lys Thr Pro Pro Ala Pro Lys Thr Pro Pro Ser Ser Gly
        115                 120                 125
```

Glu Pro Pro Lys Ser Gly Asp Arg Ser Gly Tyr Ser Ser Pro Gly Ser
            130                 135                 140

Pro Gly Thr Pro Gly Ser Arg Ser Arg Thr Pro Ser Leu Pro Thr Pro
145                 150                 155                 160

Pro Thr Arg Glu Pro Lys Lys Val Ala Val Ala Thr Pro Pro Lys
                165                 170                 175

Ser Pro Ser Ser Ala Lys Ser Arg Leu Gln Thr Ala Pro Val Pro Met
            180                 185                 190

Pro Asp Leu Lys Asn Val Lys Ser Leu Ile Gly Ser Thr Glu Asn Leu
            195                 200                 205

Lys His Gln Pro Gly Gly Gly Lys Val Gln Ile Ile Asn Lys Lys Leu
            210                 215                 220

Asp Leu Ser Asn Val Gln Ser Lys Cys Gly Ser Lys Asp Asn Ile Lys
225                 230                 235                 240

His Val Pro Gly Gly Gly Ser Val Gln Ile Val Tyr Lys Pro Val Asp
                245                 250                 255

Leu Ser Lys Val Thr Ser Lys Cys Gly Ser Leu Gly Asn Ile His His
            260                 265                 270

Lys Pro Gly Gly Gly Gln Val Glu Val Lys Ser Glu Lys Leu Asp Phe
            275                 280                 285

Lys Asp Arg Val Gln Ser Lys Ile Gly Ser Leu Asp Asn Ile Thr His
            290                 295                 300

Val Pro Gly Gly Gly Asn Lys Lys Ile Glu Thr His Lys Leu Thr Phe
305                 310                 315                 320

Arg Glu Asn Ala Lys Ala Leu Thr Asp His Gly Ala Glu Ile Val Tyr
                325                 330                 335

Lys Ser Pro Val Val Ser Gly Asp Thr Ser Pro Arg His Leu Ser Asn
            340                 345                 350

Val Ser Ser Thr Gly Ser Ile Asp Met Val Asp Ser Pro Gln Leu Ala
            355                 360                 365

Thr Leu Ala Asp Glu Val Ser Ala Ser Leu Ala Lys Gln Gly Leu
            370                 375                 380

<210> SEQ ID NO 5
<211> LENGTH: 381
<212> TYPE: PRT
<213> ORGANISM: Artificial Sequence
<220> FEATURE:
<223> OTHER INFORMATION: Human Tau 1N3R

<400> SEQUENCE: 5

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
            20                  25                  30

Gln Asp Gln Glu Gly Asp Thr Asp Ala Gly Leu Lys Glu Ser Pro Leu
        35                  40                  45

Gln Thr Pro Thr Glu Asp Gly Ser Glu Glu Pro Gly Ser Glu Thr Ser
    50                  55                  60

Asp Ala Lys Ser Thr Pro Thr Ala Glu Ala Glu Glu Ala Gly Ile Gly
65                  70                  75                  80

Asp Thr Pro Ser Leu Glu Asp Glu Ala Ala Gly His Val Thr Gln Ala
                85                  90                  95

Arg Met Val Ser Lys Ser Lys Asp Gly Thr Gly Ser Asp Asp Lys Lys
            100                 105                 110

```
Ala Lys Gly Ala Asp Gly Lys Thr Lys Ile Ala Thr Pro Arg Gly Ala
        115                 120                 125

Ala Pro Pro Gly Gln Lys Gly Gln Ala Asn Ala Thr Arg Ile Pro Ala
    130                 135                 140

Lys Thr Pro Pro Ala Pro Lys Thr Pro Pro Ser Ser Gly Glu Pro Pro
145                 150                 155                 160

Lys Ser Gly Asp Arg Ser Gly Tyr Ser Ser Pro Gly Ser Pro Gly Thr
                165                 170                 175

Pro Gly Ser Arg Ser Arg Thr Pro Ser Leu Pro Thr Pro Pro Thr Arg
            180                 185                 190

Glu Pro Lys Lys Val Ala Val Val Arg Thr Pro Pro Lys Ser Pro Ser
        195                 200                 205

Ser Ala Lys Ser Arg Leu Gln Thr Ala Pro Val Pro Met Pro Asp Leu
    210                 215                 220

Lys Asn Val Lys Ser Lys Ile Gly Ser Thr Glu Asn Leu Lys His Gln
225                 230                 235                 240

Pro Gly Gly Gly Lys Val Gln Ile Val Tyr Lys Pro Val Asp Leu Ser
                245                 250                 255

Lys Val Thr Ser Lys Cys Gly Ser Leu Gly Asn Ile His His Lys Pro
            260                 265                 270

Gly Gly Gly Gln Val Glu Val Lys Ser Glu Lys Leu Asp Phe Lys Asp
        275                 280                 285

Arg Val Gln Ser Lys Ile Gly Ser Leu Asp Asn Ile Thr His Val Pro
    290                 295                 300

Gly Gly Gly Asn Lys Lys Ile Glu Thr His Lys Leu Thr Phe Arg Glu
305                 310                 315                 320

Asn Ala Lys Ala Lys Thr Asp His Gly Ala Glu Ile Val Tyr Lys Ser
                325                 330                 335

Pro Val Val Ser Gly Asp Thr Ser Pro Arg His Leu Ser Asn Val Ser
            340                 345                 350

Ser Thr Gly Ser Ile Asp Met Val Asp Ser Pro Gln Leu Ala Thr Leu
        355                 360                 365

Ala Asp Glu Val Ser Ala Ser Leu Ala Lys Gln Gly Leu
    370                 375                 380

<210> SEQ ID NO 6
<211> LENGTH: 352
<212> TYPE: PRT
<213> ORGANISM: Artificial Sequence
<220> FEATURE:
<223> OTHER INFORMATION: Human Tau 0N3R

<400> SEQUENCE: 6

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
            20                  25                  30

Gln Asp Gln Glu Gly Asp Thr Asp Ala Gly Leu Lys Ala Glu Glu Ala
        35                  40                  45

Gly Ile Gly Asp Thr Pro Ser Leu Glu Asp Glu Ala Ala Gly His Val
    50                  55                  60

Thr Gln Ala Arg Met Val Ser Lys Ser Lys Asp Gly Thr Gly Ser Asp
65                  70                  75                  80

Asp Lys Lys Ala Lys Gly Ala Asp Gly Lys Thr Lys Ile Ala Thr Pro
                85                  90                  95

Arg Gly Ala Ala Pro Pro Gly Gln Lys Gly Gln Ala Asn Ala Thr Arg
```

```
                        100                 105                 110
Ile Pro Ala Lys Thr Pro Pro Ala Pro Lys Thr Pro Ser Ser Gly
            115                 120                 125

Glu Pro Pro Lys Ser Gly Asp Arg Ser Gly Tyr Ser Ser Pro Gly
130                 135                 140

Pro Gly Thr Pro Gly Ser Arg Ser Arg Thr Pro Ser Leu Pro Thr Pro
145                 150                 155                 160

Pro Thr Arg Glu Pro Lys Lys Val Ala Val Arg Thr Pro Pro Lys
            165                 170                 175

Ser Pro Ser Ser Ala Lys Ser Arg Leu Gln Thr Ala Pro Val Pro Met
                180                 185                 190

Pro Asp Leu Lys Asn Val Lys Ser Lys Ile Gly Ser Thr Glu Asn Leu
            195                 200                 205

Lys His Gln Pro Gly Gly Gly Lys Val Gln Ile Val Tyr Lys Pro Val
    210                 215                 220

Asp Leu Ser Lys Val Thr Ser Lys Cys Gly Ser Leu Gly Asn Ile His
225                 230                 235                 240

His Lys Pro Gly Gly Gly Gln Val Glu Val Lys Ser Glu Lys Leu Asp
            245                 250                 255

Phe Lys Asp Arg Val Gln Ser Lys Ile Gly Ser Leu Asp Asn Ile Thr
            260                 265                 270

His Val Pro Gly Gly Gly Asn Lys Lys Ile Gly Thr His Lys Leu Thr
            275                 280                 285

Phe Arg Glu Asn Ala Lys Ala Lys Thr Asp His Gly Ala Glu Ile Val
        290                 295                 300

Tyr Lys Ser Pro Val Val Ser Gly Asp Thr Ser Pro Arg His Leu Ser
305                 310                 315                 320

Asn Val Ser Ser Thr Gly Ser Ile Asp Met Val Asp Ser Pro Gln Leu
                325                 330                 335

Ala Thr Leu Ala Asp Glu Val Ser Ala Ser Leu Ala Lys Gln Gly Leu
            340                 345                 350

<210> SEQ ID NO 7
<211> LENGTH: 11
<212> TYPE: PRT
<213> ORGANISM: Artificial Sequence
<220> FEATURE:
<223> OTHER INFORMATION: Tau3-13

<400> SEQUENCE: 7

Glu Pro Arg Gln Glu Phe Glu Val Met Glu Asp
1               5                   10

<210> SEQ ID NO 8
<211> LENGTH: 10
<212> TYPE: PRT
<213> ORGANISM: Artificial Sequence
<220> FEATURE:
<223> OTHER INFORMATION: Tau4-13

<400> SEQUENCE: 8

Pro Arg Gln Glu Phe Glu Val Met Glu Asp
1               5                   10

<210> SEQ ID NO 9
<211> LENGTH: 8
<212> TYPE: PRT
<213> ORGANISM: Artificial Sequence
<220> FEATURE:
<223> OTHER INFORMATION: Tau5-13
```

```
<400> SEQUENCE: 9

Gln Glu Phe Glu Val Met Glu Asp
1               5

<210> SEQ ID NO 10
<211> LENGTH: 7
<212> TYPE: PRT
<213> ORGANISM: Artificial Sequence
<220> FEATURE:
<223> OTHER INFORMATION: tau6-13

<400> SEQUENCE: 10

Glu Phe Glu Val Met Glu Asp
1               5

<210> SEQ ID NO 11
<211> LENGTH: 6
<212> TYPE: PRT
<213> ORGANISM: Artificial Sequence
<220> FEATURE:
<223> OTHER INFORMATION: Tau7-13

<400> SEQUENCE: 11

Phe Glu Val Met Glu Asp
1               5

<210> SEQ ID NO 12
<211> LENGTH: 5
<212> TYPE: PRT
<213> ORGANISM: Artificial Sequence
<220> FEATURE:
<223> OTHER INFORMATION: Tau8-13

<400> SEQUENCE: 12

Glu Val Met Glu Asp
1               5

<210> SEQ ID NO 13
<211> LENGTH: 4
<212> TYPE: PRT
<213> ORGANISM: Artificial Sequence
<220> FEATURE:
<223> OTHER INFORMATION: Tau9-13

<400> SEQUENCE: 13

Val Met Glu Asp
1

<210> SEQ ID NO 14
<211> LENGTH: 3
<212> TYPE: PRT
<213> ORGANISM: Artificial Sequence
<220> FEATURE:
<223> OTHER INFORMATION: Tau10-13

<400> SEQUENCE: 14

Met Glu Asp
1

<210> SEQ ID NO 15
<211> LENGTH: 12
<212> TYPE: PRT
<213> ORGANISM: Artificial Sequence
<220> FEATURE:
<223> OTHER INFORMATION: Tau14-25

<400> SEQUENCE: 15
```

-continued

His Ala Gly Thr Tyr Gly Leu Gly Asp Arg Lys Asp
1               5                   10

<210> SEQ ID NO 16
<211> LENGTH: 11
<212> TYPE: PRT
<213> ORGANISM: Artificial Sequence
<220> FEATURE:
<223> OTHER INFORMATION: Tau14-24

<400> SEQUENCE: 16

His Ala Gly Thr Tyr Gly Leu Gly Asp Arg Lys
1               5                   10

<210> SEQ ID NO 17
<211> LENGTH: 7
<212> TYPE: PRT
<213> ORGANISM: Artificial Sequence
<220> FEATURE:
<223> OTHER INFORMATION: Tau14-23

<400> SEQUENCE: 17

His Ala Gly Thr Tyr Gly Leu
1               5

<210> SEQ ID NO 18
<211> LENGTH: 9
<212> TYPE: PRT
<213> ORGANISM: Artificial Sequence
<220> FEATURE:
<223> OTHER INFORMATION: Tau14-22

<400> SEQUENCE: 18

His Ala Gly Thr Tyr Gly Leu Gly Asp
1               5

<210> SEQ ID NO 19
<211> LENGTH: 8
<212> TYPE: PRT
<213> ORGANISM: Artificial Sequence
<220> FEATURE:
<223> OTHER INFORMATION: Tau14-21

<400> SEQUENCE: 19

His Ala Gly Thr Tyr Gly Leu Gly
1               5

<210> SEQ ID NO 20
<211> LENGTH: 7
<212> TYPE: PRT
<213> ORGANISM: Artificial Sequence
<220> FEATURE:
<223> OTHER INFORMATION: Tau14-20

<400> SEQUENCE: 20

His Ala Gly Thr Tyr Gly Leu
1               5

<210> SEQ ID NO 21
<211> LENGTH: 6
<212> TYPE: PRT
<213> ORGANISM: Artificial Sequence
<220> FEATURE:
<223> OTHER INFORMATION: Tau14-19

<400> SEQUENCE: 21

His Ala Gly Thr Tyr Gly

```
<210> SEQ ID NO 22
<211> LENGTH: 5
<212> TYPE: PRT
<213> ORGANISM: Artificial Sequence
<220> FEATURE:
<223> OTHER INFORMATION: Tau14-18

<400> SEQUENCE: 22

His Ala Gly Thr Tyr
1               5

<210> SEQ ID NO 23
<211> LENGTH: 4
<212> TYPE: PRT
<213> ORGANISM: Artificial Sequence
<220> FEATURE:
<223> OTHER INFORMATION: Tau14-17

<400> SEQUENCE: 23

His Ala Gly Thr
1

<210> SEQ ID NO 24
<211> LENGTH: 11
<212> TYPE: PRT
<213> ORGANISM: Artificial Sequence
<220> FEATURE:
<223> OTHER INFORMATION: Tau392-402 of htau40

<400> SEQUENCE: 24

Ile Val Tyr Lys Ser Pro Val Val Ser Gly Asp
1               5                   10

<210> SEQ ID NO 25
<211> LENGTH: 10
<212> TYPE: PRT
<213> ORGANISM: Artificial Sequence
<220> FEATURE:
<223> OTHER INFORMATION: tau392-401

<400> SEQUENCE: 25

Ile Val Tyr Lys Ser Pro Val Val Ser Gly
1               5                   10

<210> SEQ ID NO 26
<211> LENGTH: 9
<212> TYPE: PRT
<213> ORGANISM: Artificial Sequence
<220> FEATURE:
<223> OTHER INFORMATION: tau392-400

<400> SEQUENCE: 26

Ile Val Tyr Lys Ser Pro Val Val Ser
1               5

<210> SEQ ID NO 27
<211> LENGTH: 8
<212> TYPE: PRT
<213> ORGANISM: Artificial Sequence
<220> FEATURE:
<223> OTHER INFORMATION: tau392-399

<400> SEQUENCE: 27

Ile Val Tyr Lys Ser Pro Val Val
1               5
```

```
<210> SEQ ID NO 28
<211> LENGTH: 7
<212> TYPE: PRT
<213> ORGANISM: Artificial Sequence
<220> FEATURE:
<223> OTHER INFORMATION: tau392-398

<400> SEQUENCE: 28

Ile Val Tyr Lys Ser Pro Val
1               5

<210> SEQ ID NO 29
<211> LENGTH: 6
<212> TYPE: PRT
<213> ORGANISM: Artificial Sequence
<220> FEATURE:
<223> OTHER INFORMATION: 392-397

<400> SEQUENCE: 29

Ile Val Tyr Lys Ser Pro
1               5

<210> SEQ ID NO 30
<211> LENGTH: 5
<212> TYPE: PRT
<213> ORGANISM: Artificial Sequence
<220> FEATURE:
<223> OTHER INFORMATION: tau392-396

<400> SEQUENCE: 30

Ile Val Tyr Lys Ser
1               5

<210> SEQ ID NO 31
<211> LENGTH: 4
<212> TYPE: PRT
<213> ORGANISM: Artificial Sequence
<220> FEATURE:
<223> OTHER INFORMATION: tau392-395

<400> SEQUENCE: 31

Ile Val Tyr Lys
1

<210> SEQ ID NO 32
<211> LENGTH: 3
<212> TYPE: PRT
<213> ORGANISM: Artificial Sequence
<220> FEATURE:
<223> OTHER INFORMATION: tau392-394

<400> SEQUENCE: 32

Ile Val Tyr
1

<210> SEQ ID NO 33
<211> LENGTH: 11
<212> TYPE: PRT
<213> ORGANISM: Artificial Sequence
<220> FEATURE:
<223> OTHER INFORMATION: tau392-402

<400> SEQUENCE: 33

Pro Gln Leu Ala Thr Leu Ala Asp Glu Val Ser
1               5                   10

<210> SEQ ID NO 34
```

```
<211> LENGTH: 10
<212> TYPE: PRT
<213> ORGANISM: Artificial Sequence
<220> FEATURE:
<223> OTHER INFORMATION: tau392-401

<400> SEQUENCE: 34

Pro Gln Leu Ala Thr Leu Ala Asp Glu Val
1               5                   10

<210> SEQ ID NO 35
<211> LENGTH: 9
<212> TYPE: PRT
<213> ORGANISM: Artificial Sequence
<220> FEATURE:
<223> OTHER INFORMATION: tau392-400

<400> SEQUENCE: 35

Pro Gln Leu Ala Thr Leu Ala Asp Glu
1               5

<210> SEQ ID NO 36
<211> LENGTH: 8
<212> TYPE: PRT
<213> ORGANISM: Artificial Sequence
<220> FEATURE:
<223> OTHER INFORMATION: tau392-399

<400> SEQUENCE: 36

Pro Gln Leu Ala Thr Leu Ala Asp
1               5

<210> SEQ ID NO 37
<211> LENGTH: 7
<212> TYPE: PRT
<213> ORGANISM: Artificial Sequence
<220> FEATURE:
<223> OTHER INFORMATION: tau392-398

<400> SEQUENCE: 37

Pro Gln Leu Ala Thr Leu Ala
1               5

<210> SEQ ID NO 38
<211> LENGTH: 6
<212> TYPE: PRT
<213> ORGANISM: Artificial Sequence
<220> FEATURE:
<223> OTHER INFORMATION: tau392-397

<400> SEQUENCE: 38

Pro Gln Leu Ala Thr Leu
1               5

<210> SEQ ID NO 39
<211> LENGTH: 5
<212> TYPE: PRT
<213> ORGANISM: Artificial Sequence
<220> FEATURE:
<223> OTHER INFORMATION: tau396-396

<400> SEQUENCE: 39

Pro Gln Leu Ala Thr
1               5

<210> SEQ ID NO 40
<211> LENGTH: 4
<212> TYPE: PRT
```

```
<213> ORGANISM: Artificial Sequence
<220> FEATURE:
<223> OTHER INFORMATION: tau392-395

<400> SEQUENCE: 40

Pro Gln Leu Ala
1

<210> SEQ ID NO 41
<211> LENGTH: 3
<212> TYPE: PRT
<213> ORGANISM: Artificial Sequence
<220> FEATURE:
<223> OTHER INFORMATION: 392-394

<400> SEQUENCE: 41

Pro Gln Leu
1

<210> SEQ ID NO 42
<211> LENGTH: 10
<212> TYPE: PRT
<213> ORGANISM: Artificial Sequence
<220> FEATURE:
<223> OTHER INFORMATION: Tau392-402

<400> SEQUENCE: 42

Ser Pro Gln Leu Ala Thr Leu Ala Asp Glu
1               5                   10

<210> SEQ ID NO 43
<211> LENGTH: 9
<212> TYPE: PRT
<213> ORGANISM: Artificial Sequence
<220> FEATURE:
<223> OTHER INFORMATION: tau392-401

<400> SEQUENCE: 43

Ser Pro Gln Leu Ala Thr Leu Ala Asp
1               5

<210> SEQ ID NO 44
<211> LENGTH: 8
<212> TYPE: PRT
<213> ORGANISM: Artificial Sequence
<220> FEATURE:
<223> OTHER INFORMATION: tau392-400

<400> SEQUENCE: 44

Ser Pro Gln Leu Ala Thr Leu Ala
1               5

<210> SEQ ID NO 45
<211> LENGTH: 7
<212> TYPE: PRT
<213> ORGANISM: Artificial Sequence
<220> FEATURE:
<223> OTHER INFORMATION: tau392-399

<400> SEQUENCE: 45

Ser Pro Gln Leu Ala Thr Leu
1               5

<210> SEQ ID NO 46
<211> LENGTH: 6
<212> TYPE: PRT
<213> ORGANISM: Artificial Sequence
<220> FEATURE:
```

```
<223> OTHER INFORMATION: tau392-398

<400> SEQUENCE: 46

Ser Pro Gln Leu Ala Thr
1               5

<210> SEQ ID NO 47
<211> LENGTH: 5
<212> TYPE: PRT
<213> ORGANISM: Artificial Sequence
<220> FEATURE:
<223> OTHER INFORMATION: tau392-397

<400> SEQUENCE: 47

Ser Pro Gln Leu Ala
1               5

<210> SEQ ID NO 48
<211> LENGTH: 4
<212> TYPE: PRT
<213> ORGANISM: Artificial Sequence
<220> FEATURE:
<223> OTHER INFORMATION: tau392-396

<400> SEQUENCE: 48

Ser Pro Gln Leu
1

<210> SEQ ID NO 49
<211> LENGTH: 3
<212> TYPE: PRT
<213> ORGANISM: Artificial Sequence
<220> FEATURE:
<223> OTHER INFORMATION: tau392-395

<400> SEQUENCE: 49

Ser Pro Gln
1

<210> SEQ ID NO 50
<211> LENGTH: 8
<212> TYPE: PRT
<213> ORGANISM: Artificial Sequence
<220> FEATURE:
<223> OTHER INFORMATION: tau391-399

<400> SEQUENCE: 50

Asp Ser Pro Gln Leu Ala Thr Leu
1               5

<210> SEQ ID NO 51
<211> LENGTH: 11
<212> TYPE: PRT
<213> ORGANISM: Artificial Sequence
<220> FEATURE:
<223> OTHER INFORMATION: tau381-391 of htau40

<400> SEQUENCE: 51

Asn Ala Lys Ala Lys Thr Asp His Gly Ala Glu
1               5                   10

<210> SEQ ID NO 52
<211> LENGTH: 10
<212> TYPE: PRT
<213> ORGANISM: Artificial Sequence
<220> FEATURE:
<223> OTHER INFORMATION: tau382-391
```

```
<400> SEQUENCE: 52

Ala Lys Ala Lys Thr Asp His Gly Ala Glu
1               5                   10

<210> SEQ ID NO 53
<211> LENGTH: 9
<212> TYPE: PRT
<213> ORGANISM: Artificial Sequence
<220> FEATURE:
<223> OTHER INFORMATION: tau383-391

<400> SEQUENCE: 53

Lys Ala Lys Thr Asp His Gly Ala Glu
1               5

<210> SEQ ID NO 54
<211> LENGTH: 8
<212> TYPE: PRT
<213> ORGANISM: Artificial Sequence
<220> FEATURE:
<223> OTHER INFORMATION: tau384-391

<400> SEQUENCE: 54

Ala Lys Thr Asp His Gly Ala Glu
1               5

<210> SEQ ID NO 55
<211> LENGTH: 7
<212> TYPE: PRT
<213> ORGANISM: Artificial Sequence
<220> FEATURE:
<223> OTHER INFORMATION: tau381-391

<400> SEQUENCE: 55

Lys Thr Asp His Gly Ala Glu
1               5

<210> SEQ ID NO 56
<211> LENGTH: 6
<212> TYPE: PRT
<213> ORGANISM: Artificial Sequence
<220> FEATURE:
<223> OTHER INFORMATION: 386-391

<400> SEQUENCE: 56

Thr Asp His Gly Ala Glu
1               5

<210> SEQ ID NO 57
<211> LENGTH: 5
<212> TYPE: PRT
<213> ORGANISM: Artificial Sequence
<220> FEATURE:
<223> OTHER INFORMATION: tau387-391

<400> SEQUENCE: 57

Asp His Gly Ala Glu
1               5

<210> SEQ ID NO 58
<211> LENGTH: 4
<212> TYPE: PRT
<213> ORGANISM: Artificial Sequence
<220> FEATURE:
<223> OTHER INFORMATION: tau388-391

<400> SEQUENCE: 58
```

```
His Gly Ala Glu
1

<210> SEQ ID NO 59
<211> LENGTH: 3
<212> TYPE: PRT
<213> ORGANISM: Artificial Sequence
<220> FEATURE:
<223> OTHER INFORMATION: tau389-391

<400> SEQUENCE: 59

Gly Ala Glu
1

<210> SEQ ID NO 60
<211> LENGTH: 11
<212> TYPE: PRT
<213> ORGANISM: Artificial Sequence
<220> FEATURE:
<223> OTHER INFORMATION: tau381-391

<400> SEQUENCE: 60

Ser Ser Thr Gly Ser Ile Asp Met Val Asp Ser
1               5                   10

<210> SEQ ID NO 61
<211> LENGTH: 10
<212> TYPE: PRT
<213> ORGANISM: Artificial Sequence
<220> FEATURE:
<223> OTHER INFORMATION: tau381-391

<400> SEQUENCE: 61

Ser Thr Gly Ser Ile Asp Met Val Asp Ser
1               5                   10

<210> SEQ ID NO 62
<211> LENGTH: 9
<212> TYPE: PRT
<213> ORGANISM: Artificial Sequence
<220> FEATURE:
<223> OTHER INFORMATION: tau383-391

<400> SEQUENCE: 62

Thr Gly Ser Ile Asp Met Val Asp Ser
1               5

<210> SEQ ID NO 63
<211> LENGTH: 7
<212> TYPE: PRT
<213> ORGANISM: Artificial Sequence
<220> FEATURE:
<223> OTHER INFORMATION: tau381-391

<400> SEQUENCE: 63

Ser Ile Asp Met Val Asp Ser
1               5

<210> SEQ ID NO 64
<211> LENGTH: 7
<212> TYPE: PRT
<213> ORGANISM: Artificial Sequence
<220> FEATURE:
<223> OTHER INFORMATION: tau385-391

<400> SEQUENCE: 64

Ser Ile Asp Met Val Asp Ser
1               5
```

```
<210> SEQ ID NO 65
<211> LENGTH: 6
<212> TYPE: PRT
<213> ORGANISM: Artificial Sequence
<220> FEATURE:
<223> OTHER INFORMATION: tau386-391

<400> SEQUENCE: 65

Ile Asp Met Val Asp Ser
1               5

<210> SEQ ID NO 66
<211> LENGTH: 5
<212> TYPE: PRT
<213> ORGANISM: Artificial Sequence
<220> FEATURE:
<223> OTHER INFORMATION: 387-391

<400> SEQUENCE: 66

Asp Met Val Asp Ser
1               5

<210> SEQ ID NO 67
<211> LENGTH: 4
<212> TYPE: PRT
<213> ORGANISM: Artificial Sequence
<220> FEATURE:
<223> OTHER INFORMATION: tau388-391

<400> SEQUENCE: 67

Met Val Asp Ser
1

<210> SEQ ID NO 68
<211> LENGTH: 3
<212> TYPE: PRT
<213> ORGANISM: Artificial Sequence
<220> FEATURE:
<223> OTHER INFORMATION: tau389-391

<400> SEQUENCE: 68

Val Asp Ser
1

<210> SEQ ID NO 69
<211> LENGTH: 11
<212> TYPE: PRT
<213> ORGANISM: Artificial Sequence
<220> FEATURE:
<223> OTHER INFORMATION: tau381-391

<400> SEQUENCE: 69

Asn Val Ser Ser Thr Gly Ser Ile Asp Met Val
1               5                   10

<210> SEQ ID NO 70
<211> LENGTH: 10
<212> TYPE: PRT
<213> ORGANISM: Artificial Sequence
<220> FEATURE:
<223> OTHER INFORMATION: tau382-391

<400> SEQUENCE: 70

Val Ser Ser Thr Gly Ser Ile Asp Met Val
1               5                   10
```

<210> SEQ ID NO 71
<211> LENGTH: 9
<212> TYPE: PRT
<213> ORGANISM: Artificial Sequence
<220> FEATURE:
<223> OTHER INFORMATION: tau383-391

<400> SEQUENCE: 71

Ser Ser Thr Gly Ser Ile Asp Met Val
1               5

<210> SEQ ID NO 72
<211> LENGTH: 8
<212> TYPE: PRT
<213> ORGANISM: Artificial Sequence
<220> FEATURE:
<223> OTHER INFORMATION: tau384-391

<400> SEQUENCE: 72

Ser Thr Gly Ser Ile Asp Met Val
1               5

<210> SEQ ID NO 73
<211> LENGTH: 7
<212> TYPE: PRT
<213> ORGANISM: Artificial Sequence
<220> FEATURE:
<223> OTHER INFORMATION: tau385-391

<400> SEQUENCE: 73

Thr Gly Ser Ile Asp Met Val
1               5

<210> SEQ ID NO 74
<211> LENGTH: 6
<212> TYPE: PRT
<213> ORGANISM: Artificial Sequence
<220> FEATURE:
<223> OTHER INFORMATION: tau386-391

<400> SEQUENCE: 74

Gly Ser Ile Asp Met Val
1               5

<210> SEQ ID NO 75
<211> LENGTH: 5
<212> TYPE: PRT
<213> ORGANISM: Artificial Sequence
<220> FEATURE:
<223> OTHER INFORMATION: tau387-391

<400> SEQUENCE: 75

Ser Ile Asp Met Val
1               5

<210> SEQ ID NO 76
<211> LENGTH: 3
<212> TYPE: PRT
<213> ORGANISM: Artificial Sequence
<220> FEATURE:
<223> OTHER INFORMATION: 389-391

<400> SEQUENCE: 76

Asp Met Val
1

<210> SEQ ID NO 77
<211> LENGTH: 3

```
<212> TYPE: PRT
<213> ORGANISM: Artificial Sequence
<220> FEATURE:
<223> OTHER INFORMATION: tau389-391

<400> SEQUENCE: 77

Asp Met Val
1

<210> SEQ ID NO 78
<211> LENGTH: 11
<212> TYPE: PRT
<213> ORGANISM: Artificial Sequence
<220> FEATURE:
<223> OTHER INFORMATION: tau410-421

<400> SEQUENCE: 78

Asn Val Ser Thr Gly Ser Ile Asp Met Val Asp
1               5                   10

<210> SEQ ID NO 79
<211> LENGTH: 10
<212> TYPE: PRT
<213> ORGANISM: Artificial Sequence
<220> FEATURE:
<223> OTHER INFORMATION: tau411-421

<400> SEQUENCE: 79

Val Ser Thr Gly Ser Ile Asp Met Val Asp
1               5                   10

<210> SEQ ID NO 80
<211> LENGTH: 9
<212> TYPE: PRT
<213> ORGANISM: Artificial Sequence
<220> FEATURE:
<223> OTHER INFORMATION: tau412-421

<400> SEQUENCE: 80

Ser Thr Gly Ser Ile Asp Met Val Asp
1               5

<210> SEQ ID NO 81
<211> LENGTH: 8
<212> TYPE: PRT
<213> ORGANISM: Artificial Sequence
<220> FEATURE:
<223> OTHER INFORMATION: tau413-421

<400> SEQUENCE: 81

Thr Gly Ser Ile Asp Met Val Asp
1               5

<210> SEQ ID NO 82
<211> LENGTH: 7
<212> TYPE: PRT
<213> ORGANISM: Artificial Sequence
<220> FEATURE:
<223> OTHER INFORMATION: tau414-421

<400> SEQUENCE: 82

Gly Ser Ile Asp Met Val Asp
1               5

<210> SEQ ID NO 83
<211> LENGTH: 6
<212> TYPE: PRT
<213> ORGANISM: Artificial Sequence
```

```
<220> FEATURE:
<223> OTHER INFORMATION: tau415-421

<400> SEQUENCE: 83

Ser Ile Asp Met Val Asp
1               5

<210> SEQ ID NO 84
<211> LENGTH: 5
<212> TYPE: PRT
<213> ORGANISM: Artificial Sequence
<220> FEATURE:
<223> OTHER INFORMATION: tau416-421

<400> SEQUENCE: 84

Ile Asp Met Val Asp
1               5

<210> SEQ ID NO 85
<211> LENGTH: 4
<212> TYPE: PRT
<213> ORGANISM: Artificial Sequence
<220> FEATURE:
<223> OTHER INFORMATION: tau417-421

<400> SEQUENCE: 85

Asp Met Val Asp
1

<210> SEQ ID NO 86
<211> LENGTH: 10
<212> TYPE: PRT
<213> ORGANISM: Artificial Sequence
<220> FEATURE:
<223> OTHER INFORMATION: TauC3 immunizing peptide

<400> SEQUENCE: 86

Ser Ser Thr Gly Ser Ile Asp Met Val Asp
1               5                   10

<210> SEQ ID NO 87
<211> LENGTH: 10
<212> TYPE: PRT
<213> ORGANISM: Artificial Sequence
<220> FEATURE:
<223> OTHER INFORMATION: tau422-432

<400> SEQUENCE: 87

Ser Pro Gln Leu Ala Thr Leu Ala Asp Glu
1               5                   10

<210> SEQ ID NO 88
<211> LENGTH: 9
<212> TYPE: PRT
<213> ORGANISM: Artificial Sequence
<220> FEATURE:
<223> OTHER INFORMATION: tau422-431

<400> SEQUENCE: 88

Ser Pro Gln Leu Ala Thr Leu Ala Asp
1               5

<210> SEQ ID NO 89
<211> LENGTH: 8
<212> TYPE: PRT
<213> ORGANISM: Artificial Sequence
<220> FEATURE:
<223> OTHER INFORMATION: tau422-430
```

```
<400> SEQUENCE: 89

Ser Pro Gln Leu Ala Thr Leu Ala
1               5

<210> SEQ ID NO 90
<211> LENGTH: 7
<212> TYPE: PRT
<213> ORGANISM: Artificial Sequence
<220> FEATURE:
<223> OTHER INFORMATION: tau422-429

<400> SEQUENCE: 90

Ser Pro Gln Leu Ala Thr Leu
1               5

<210> SEQ ID NO 91
<211> LENGTH: 6
<212> TYPE: PRT
<213> ORGANISM: Artificial Sequence
<220> FEATURE:
<223> OTHER INFORMATION: tau422-428

<400> SEQUENCE: 91

Ser Pro Gln Leu Ala Thr
1               5

<210> SEQ ID NO 92
<211> LENGTH: 5
<212> TYPE: PRT
<213> ORGANISM: Artificial Sequence
<220> FEATURE:
<223> OTHER INFORMATION: tau422-427

<400> SEQUENCE: 92

Ser Pro Gln Leu Ala
1               5

<210> SEQ ID NO 93
<211> LENGTH: 4
<212> TYPE: PRT
<213> ORGANISM: Artificial Sequence
<220> FEATURE:
<223> OTHER INFORMATION: tau422-426

<400> SEQUENCE: 93

Ser Pro Gln Leu
1

<210> SEQ ID NO 94
<211> LENGTH: 3
<212> TYPE: PRT
<213> ORGANISM: Artificial Sequence
<220> FEATURE:
<223> OTHER INFORMATION: tau422-424

<400> SEQUENCE: 94

Ser Pro Gln
1

<210> SEQ ID NO 95
<211> LENGTH: 14
<212> TYPE: PRT
<213> ORGANISM: tetanus toxin bacteria

<400> SEQUENCE: 95

Gln Tyr Ile Lys Ala Asn Ser Lys Phe Ile Gly Ile Thr Glu
```

<210> SEQ ID NO 96
<211> LENGTH: 14
<212> TYPE: PRT
<213> ORGANISM: tetanus toxin bacteria

<400> SEQUENCE: 96

Gln Tyr Ile Lys Ala Asn Ser Lys Phe Ile Gly Ile Thr Glu
1               5                   10

<210> SEQ ID NO 97
<211> LENGTH: 15
<212> TYPE: PRT
<213> ORGANISM: Hepatitis B virus

<400> SEQUENCE: 97

Phe Phe Leu Leu Thr Arg Ile Leu Thr Ile Phe Gln Ser Leu Asp
1               5                   10                  15

<210> SEQ ID NO 98
<211> LENGTH: 14
<212> TYPE: PRT
<213> ORGANISM: Pertussis toxin bacteria

<400> SEQUENCE: 98

Val Arg Val His Val Ser Lys Glu Glu Gln Tyr Tyr Asp Tyr
1               5                   10

<210> SEQ ID NO 99
<211> LENGTH: 16
<212> TYPE: PRT
<213> ORGANISM: tetanus toxin bacteria

<400> SEQUENCE: 99

Lys Lys Gln Tyr Ile Lys Ala Asn Ser Lys Phe Ile Gly Ile Thr Glu
1               5                   10                  15

<210> SEQ ID NO 100
<211> LENGTH: 16
<212> TYPE: PRT
<213> ORGANISM: tetanus toxin bacteria

<400> SEQUENCE: 100

Lys Lys Phe Asn Asn Phe Thr Val Ser Phe Trp Leu Arg Val Pro Lys
1               5                   10                  15

<210> SEQ ID NO 101
<211> LENGTH: 15
<212> TYPE: PRT
<213> ORGANISM: Pertussis toxin bacteria

<400> SEQUENCE: 101

Tyr Met Ser Gly Leu Ala Val Arg Val His Val Ser Lys Glu Glu
1               5                   10                  15

<210> SEQ ID NO 102
<211> LENGTH: 16
<212> TYPE: PRT
<213> ORGANISM: Tetanus toxin bacteria

<400> SEQUENCE: 102

Tyr Asp Pro Asn Tyr Leu Arg Thr Asp Ser Asp Lys Asp Arg Phe Leu
1               5                   10                  15

-continued

<210> SEQ ID NO 103
<211> LENGTH: 24
<212> TYPE: PRT
<213> ORGANISM: Pertussis toxin bacteria

<400> SEQUENCE: 103

Gly Ala Tyr Ala Arg Cys Pro Asn Gly Thr Arg Ala Leu Thr Val Ala
1 5 10 15

Glu Leu Arg Gly Asn Ala Glu Leu
20

<210> SEQ ID NO 104
<211> LENGTH: 15
<212> TYPE: PRT
<213> ORGANISM: Measles virus

<400> SEQUENCE: 104

Leu Ser Glu Ile Lys Gly Val Ile Val His Arg Leu Glu Gly Val
1 5 10 15

<210> SEQ ID NO 105
<211> LENGTH: 20
<212> TYPE: PRT
<213> ORGANISM: measles virus

<400> SEQUENCE: 105

Gly Ile Leu Glu Ser Arg Gly Ile Lys Ala Arg Ile Thr His Val Ser
1 5 10 15

Thr Glu Ser Tyr
20

<210> SEQ ID NO 106
<211> LENGTH: 16
<212> TYPE: PRT
<213> ORGANISM: Tetanus toxin bacteria

<400> SEQUENCE: 106

Trp Val Arg Asp Ile Ile Asp Asp Phe Thr Asn Glu Ser Ser Gln Lys
1 5 10 15

<210> SEQ ID NO 107
<211> LENGTH: 16
<212> TYPE: PRT
<213> ORGANISM: Tetanus toxin bacteria

<400> SEQUENCE: 107

Asp Val Ser Thr Ile Val Pro Tyr Ile Gly Pro Ala Leu Asn His Val
1 5 10 15

<210> SEQ ID NO 108
<211> LENGTH: 24
<212> TYPE: PRT
<213> ORGANISM: Clamydia trachomitis

<400> SEQUENCE: 108

Ala Leu Asn Ile Trp Asp Arg Phe Asp Val Phe Cys Thr Leu Gly Ala
1 5 10 15

Thr Thr Tyr Leu Lys Glu Asn Ser
20

<210> SEQ ID NO 109
<211> LENGTH: 23
<212> TYPE: PRT
<213> ORGANISM: Diphteria toxin bacteria -continued

<400> SEQUENCE: 109

Asp Ser Glu Thr Ala Asp Asn Leu Glu Lys Thr Val Ala Ala Leu Ser
1               5                   10                  15

Ile Leu Pro Gly Ile Gly Cys
            20

<210> SEQ ID NO 110
<211> LENGTH: 39
<212> TYPE: PRT
<213> ORGANISM: Diphteria toxin bacteria

<400> SEQUENCE: 110

Glu Glu Ile Val Ala Gln Ser Ile Ala Leu Ser Ser Leu Met Val Ala
1               5                   10                  15

Gln Ala Ile Pro Leu Val Gly Glu Leu Val Asp Ile Gly Phe Ala Ala
20 25 30

Thr Asn Phe Val Glu Ser Cys
35

<210> SEQ ID NO 111
<211> LENGTH: 21
<212> TYPE: PRT
<213> ORGANISM: Plasmodium falciparum

<400> SEQUENCE: 111

Asp Ile Glu Lys Lys Ile Ala Lys Met Glu Lys Ala Ser Ser Val Phe
1 5 10 15

Asn Val Val Asn Ser
20

<210> SEQ ID NO 112
<211> LENGTH: 16
<212> TYPE: PRT
<213> ORGANISM: Schistom mansoni

<400> SEQUENCE: 112

Lys Trp Phe Lys Thr Asn Ala Pro Asn Gly Val Asp Glu Lys Ile Arg
1 5 10 15

<210> SEQ ID NO 113
<211> LENGTH: 14
<212> TYPE: PRT
<213> ORGANISM: Escherichia coli

<400> SEQUENCE: 113

Gly Leu Gln Gly Lys Ile Ala Asp Ala Val Lys Ala Lys Gly
1 5 10

<210> SEQ ID NO 114
<211> LENGTH: 19
<212> TYPE: PRT
<213> ORGANISM: Escherichia coli

<400> SEQUENCE: 114

Gly Leu Ala Ala Gly Leu Val Gly Met Ala Ala Pro Ala Met Val Glu
1 5 10 15

Asp Val Asn

<210> SEQ ID NO 115
<211> LENGTH: 20
<212> TYPE: PRT
<213> ORGANISM: Escherichia coli -continued

```
<400> SEQUENCE: 115

Ser Thr Glu Thr Gly Asn Gln His His Tyr Gln Thr Arg Val Val Ser
1               5                   10                  15

Asn Ala Asn Lys
            20

<210> SEQ ID NO 116
<211> LENGTH: 27
<212> TYPE: PRT
<213> ORGANISM: Artificial Sequence
<220> FEATURE:
<223> OTHER INFORMATION: anti delta tau peptide

<400> SEQUENCE: 116

Val Asp Asp Ala Leu Ile Asn Ser Thr Lys Ile Tyr Ser Tyr Phe Pro
1               5                   10                  15

Ser Val Gly Pro Ser Leu Ile Asp Met Val Asp
            20                  25

<210> SEQ ID NO 117
<211> LENGTH: 26
<212> TYPE: PRT
<213> ORGANISM: Artificial Sequence
<220> FEATURE:
<223> OTHER INFORMATION: anti-Ab peptide

<400> SEQUENCE: 117

Asp Ala Glu Phe Gly Pro Ser Leu Val Asp Asp Ala Leu Ile Asn Ser
1               5                   10                  15

Thr Lys Ile Tyr Ser Tyr Phe Pro Ser Val
            20                  25
```

TREATMENT OF TAUOPATHIES

BACKGROUND OF THE INVENTION

Alzheimer's disease (AD) is a common chronic progressive neurodegenerative disease in which there is an irreversible loss of cognitive and behavioral functions. The disease can persevere for over 10 years, advancing from mild symptoms to extremely severe manifestations. AD is said to afflict approximately 10% of the population over the age of 65 and more than 30% of the population over the age of 80.

Pathologically, Alzheimer's disease presents as extracellular amyloid plaques and intracellular neurofibrillary tangles. The neurofibrillary tangles are composed, e.g., of the microtubule-binding protein tau, which is assembled into paired helical and straight filaments. It has been suggested that these entities may be functionally linked, although the mechanisms by which amyloid deposition promotes pathological tau filament assembly is not clear.

The common denominator of intracellular neurofibrillary structures (neurofibrillary tangles, dystrophic neurites, and neurophil threads) is paired helical filaments (PHFs). The major protein subunit of the PHFs is microtubule associated protein tau in abnormally hyperphosphorylated form (Grundke-Iqbal et al., 1986; Wischik et al., 1988 a,b). Neurons with neurofibrillary changes degenerate, and the degree of this degeneration directly correlates with the degree of dementia in the affected individuals (Blessed et al., 1968).

Normal tau is a microtubule associated protein that distributes mainly to axons. Tau protein takes part in modulating the assembly, spatial organization and behavior of microtubules (MT) in neurons and probably glial cell bodies (Drewes et al., 1998; Drubin and Kirschner, 1986; Lo-Presti et al., 1995). Tau proteins are encoded by a single gene located on chromosome 17, but are detected as multiple isoforms in tissue extracts from adult brains (Goedert et al., 1989; Himmler A., 1989; Kosik et al., 1989). Heterogeneity of tau proteins is in part due to alternative splicing, giving rise to six isoforms in the adult human brain. These distinct isoforms differ by the presence or absence of 29- or 58-amino acid inserts in the amino-terminal region and by the addition or deletion of a tandem repeat (which can be repeated either 3 or 4 times) in a carboxy-terminal region of tau referred to as microtubule binding domain. This region is composed of imperfect repeats of 31 or 32 amino acid residues. Referring to the longest human tau protein isoform, htau40, containing all inserts (441 amino acid long) in humans, the smallest tau isoform contains 352 amino acid residues with three tandem repeats in the MT-binding domain and no amino terminal inserts, whereas the largest isoform contains 441 residues with four repeats and both amino terminal inserts.

A number of neurological diseases are known to have filamentous cellular inclusions containing microtubule associated protein tau, e.g., Alzheimer's disease (AD), progressive supranuclear palsy (PSP), corticobasal degeneration (CBD), Pick's disease (PiD) and a group of related disorders collectively termed frontotemporal dementia with Parkinsonism linked to chromosome 17 (FTDP-17), amyotropic lateral sclerosis (ALS), Creutzfeldt-Jakob disease (CJD), dementia pugilistica (DP), Gerstmann-Straussler-Scheinker disease (GSSD), Lewy body disease and Huntington disease (Dickinson et al., 1998; DiFiglia et al., 1997; Formo, 1986; Hirano and Zimmerman, 1962; Nishimura et al., 1995; Prusiner 1996; Reed et al., 1998; Roberts, 1998; Schmidt et al., 1996; Shankar et al., 1989; Spillantini et al., 1998). Although the etiology, clinical symptoms, pathologic findings and the biochemical composition of inclusions in these diseases are different, there is emerging evidence suggesting that the mechanisms involved in aggregation of normal cellular proteins to form various filamentous inclusions are comparable. It is believed, that an initial alteration in conformation of microtubule associated protein tau, that initiates generation of nuclei or seeds for filament assembly, is one of the key features. This process can be influenced by the post-translational modification of normal proteins, by mutation or deletion of certain genes and by factors that bind normal proteins and thus alter their conformation.

The tau protein is very hydrophilic, and is one of the most soluble proteins known. It can be readily extracted from brain tissue or cultured cells. Therefore, the aggregation of tau protein in AD is highly suspicious. In comparison, filamentous tau extracted from Alzheimer's diseased brain tissues is relatively insoluble. Besides phosphorylation, insoluble and normal soluble tau differ in the extent of posttranslational modifications, which include glycosylation, glycation, ubiquitination and racemization (Kenessey et al., 1995; Ko et al., 1999; Mori et al., 1987; Wang et al., 1996; Yan et al., 1994).

It has previously been reported that tau in AD brain neurofibrillary deposits is truncated at its C-terminus at the glutamic acid residue Glu391 (Novak, et al., 1989; Novak, et al., 1993). Truncation of tau at Glu391 leads to AD-specific conformational changes that are recognized by the conformational antibody MN423 (Novak, et al., 1989; Novak, et al., 1993; Csokova, et al., 2006; Skrabana, et al., 2006; and Skrabana, et al., 2007).

The mechanism by which tau protein is modified to take part in filament formation in AD is unknown. Phosphorylation of tau affects the potential of tau to form aggregates, producing either stimulatory or inhibitory effects, presumably depending on the site of phosphorylation (Crowther et al., 1994; Schneider et al., 1999). Hyperphosphorylation of tau at many sites appears to precede assembly into filaments, based on findings in mouse lines expressing human tau with FTDP-17T mutations (Lewis et al. 2000; Allen et al. 2002). Many in vitro studies taken together suggest (a) that the microtubule binding domain is important for assembly of tau filaments; and (b) that formation of tau filaments requires conformational change(s) of tau. These studies also indicate that none of tau modifications described therein are alone capable to induce filamentous tau formations that correlate with clinical expression of Alzheimer's disease.

Asuni et al., "Immunotherapy Targeting Pathological Tau Conformers in a Tangle Mouse Model Reduces Brain Pathology with Associated Functional Improvements", Journal of Neuroscience, 27 (34): 9115-9129 (Aug. 2, 2007) discussed a study in which they sought to determine the effectiveness of active immunization directed against phosphorylated tau conformers in the CNS by immunizing P301L mice with a phosphorylated tau epitope with subsequent analysis of tau pathology and associated functional impairments. They determined that active immunization with a phosphorylated tau epitope Tau 379-408 (P-$_{Ser396,404}$) reduces aggregated tau in the brain and slows progression of the tangle-related behavioral pheno-type in the mice.

Gamblin et al. "Caspase Cleavage of Tau: Linking Amyloid and Neurofibrillary Tangles of Alzheimer's Disease", PNAS Vol 100, No. 17, pp. 10032-10037 (Aug. 19, 2003), reported that tau is proteolyzed by multiple caspases at a highly conserved aspartate residue ($Asp^{421}$) in its C terminus in vitro and in neurons treated with amyloid-β ($Aβ_{1-42}$) peptide. Tau was reported to be rapidly cleaved at $Asp^{421}$ in Aβ-treated neurons (within 2 hours), and its proteolysis appears to precede the nuclear events of apoptosis. Gamblin et al. also demonstrated that caspase cleavage of tau generates a truncated protein that lacks its C-terminal 20 amino acids and assembles more rapidly and more extensively into tau filaments in vitro than wild-type tau. Using a monoclonal antibody that specifically recognizes tau truncated at $Asp^{421}$, Gamblin et al. showed that tau is proteolytically cleaved at this site in the fibrillar pathologies of AD brain, and suggested that Aβ peptides promote pathological tau filament assembly in neurons by triggering caspase cleavage of tau and generating a proteolytic product with enhanced polymerization kinetics.

Delobel et al., "Analysis of Tau Phosphorylation and Truncation in a Mouse Model of Human Tauopathy", American Journal of Pathology, Vol. 172, No. 1, pp. 123-131 (January 2008), investigated the time course of the appearance of phosphorylated and truncated tau in the brain and spinal cord of mice transgenic for human P301S tau protein. They reported that soluble tau was strongly phosphorylated at 1 to 6 months, and low levels of phosphorylated, sarkosyl-insoluble tau were detected at 2 months with a steady increase up to 6 months of age. They further reported that tau truncated at D421 was detected at low levels in Tris-soluble and detergent soluble tau at 3-6 months of age. They concluded that the late appearance and low abundance of tau ending at D421 indicates that it is unlikely that truncation at this site is necessary for the assembly of tau into filaments.

Zhang et al., "Truncated Tau at D421 is Associated with Neurodegeneration and Tangle Formation in the Brain of Alzheimer Transgenic Models", Acta Neuropathol 117:687-697 (2009), analyzed spatial relationships among tau truncation, tau phosphorylation and neurodegeneration or tangle formation in a tau P302L mice and in a triple transgenic mouse model that produces both amyloid plaques and neurofibrillary tangles. They reported that a few neurons were detected that contained abundant truncated tau but were lacking hyperphosphorylation, and these neurons exhibited nuclear condensation, while truncated tau was commonly associated with high immunoreactivity of hyperphosphorylated tau and dense Gallyas silver staining. They concluded that tau truncation appears after tau hyperphosphyorylation in the brain of these two transgenic mouse models, and that accumulation of truncated tau, in the absence or the presence of physhorylated tau, is closely associated with a subset of neurons undergoing degeneration or containing neurofibrillary tangles.

Likewise, Khurana, et al. (2010), "Lysosomal Dysfunction Promotes Cleavage and Neurotoxicity of Tau InVivo", PLoS Genet 6(7): e1001026. doi:10.1371/journal.pgen.1001026, demonstrated that removing cathepsin D in adult postmitotic neurons leads to aberrant lysosomal expansion and caspase activation in vivo, suggesting a mechanism for C-terminal truncation of tau. They concluded that caspase cleavage of tau may be a molecular mechanism through which lysosomal dysfunction and neurodegeneration are causally linked in AD.

Sigurdsson, "Tau-Focused Immunotherapy for Alzheimer's Disease and Related Tauopathies", Current Alzheimer Research, Vo. 6, pp. 446-450 (2009), immunized transgenic mice expressing the P301L tau mutation with a 30 amino acid tau fragment that contained two phosphorylation sites that are prominent in AD (Tau 379-408[P-Ser396,404] and found that active immunization targeting this AD phospho-tau epitope reduces aggregated tau in the brain and prevents/slows progression of the tangle-related behavioral phenotype, including cognitive impairment. He concluded that these antibodies enter the brain and bind to pathological tau within neurons although the therapeutic effect may be at least in part due to clearance of extracellular tau that may have biological effects.

Calignon et al., "Caspase Activation Precedes and Leads to Tangles", Nature Vol. 464/22, pp. 1201-1205 (April 2010), using in vivo multiphoton imaging to observe tangles and activation of executioner caspases in living tau transgenic mice (Tg4510 strain), found that caspase activation occurs first, and precedes tangle formation by hours to days. Based on this data, Calignon et al. proposed that caspase activation cleaves tau to initiate tangle formation, then truncated tau recruits normal tau to misfold and form tangles. They further suggested that tangles are "off pathway" to acute neuronal death, and that soluble tau rather than fibrillar tau may be the critical toxic moiety underlying neurodegeneration.

Kovacech et al., "Tau Truncation is a Productive Posttranslational Modification of Neurofibrillary Degeneration in Alzheimer's Disease", Current Alzheimer Research, Vol 7, pp. 708-716 (2010), conclude that two posttranslational modifications of tau found in AD are assumed to play an inducing role in the neurofibrillary degeneration; truncation and hyperphosphorylation, and that it is impossible to precisely determine the temporal role of phosphorylation in the development of tau pathology because tau mutations are known to alter the conformation of the protein and lead to its higher and faster phosphorylation in vitro.

Horowitz et al., "Early N-Terminal Changes and Caspase-6 Cleavage of Tau in Alzheimer's Disease", The Journal of Neuroscience, 24(36), pp. 7895-7902 (2004), reported immunohistochemical staining in a cohort of 35 cases ranging from noncognitively impaired to early AD with a panel of three N-terminal anti-tau antibodies: Tau-12, 5A6, and 9G3-pY18. Of these three, the phosphorylation-independent epitope of 5A6 was the earliest to emerge in the pathological lesions of tau, followed by the appearance of the Tau-12 epitope. It was reported that the unmasking of the Tau-12 epitope in more mature 5A6-positive tangles was not correlated with tau phosphorylation at tyrosine 18 (9G3-pY18). The extreme N-terminus of tau was lost later in the course of tangle evolution, correlating temporally with the appearance of a C-terminal caspase-truncated epitope lacking residues 422-441. In addition, caspase-6 cleaved the N terminus of tau in vitro, preventing immunoreactivity with both Tau-12 and 5A6, with the in vitro caspase-6 truncation site being identified as Asp13. The authors concluded that their results suggested a role for caspase-6 and N-terminal truncation of tau during neurofibrillary tangle evolution and the progression of AD.

It would be desirable to provide treatments which could interfere in the initiation of tau changes leading to filament formation or which could interfere with filament formation leading to tangles in disease conditions such as AD, and to develop therapeutic agents and dosage forms to treat, prevent or interfere in the progression of tauopathies.

Citation of any document herein is not intended as an admission that such document is pertinent prior art, or considered material to the patentability of any claim of the present application. Any statement as to content or a date of any document is based on the information available to applicant at the time of filing and does not constitute an admission as to the correctness of such a statement.

SUMMARY OF THE INVENTION

An object of the present invention is therefore to provide methods of treatment, therapeutic agents and compositions for therapeutic intervention in and/or prevention of Alzheimer's disease and other tauopathies.

It is a further object of the invention to provide antibodies capable of selectively recognizing a tau truncated at its C-terminus (e.g., at the glutamic acid residue Glu391 or at the aspartic acid residue Asp421) or its N-terminus (e.g., at amino acid Asp13) (e.g., tau1-13, tau14-441, tau14-391, tau391-414, tau1-391, tau1-421, tau14-421, tau14-410, tau391-410, tau14-412, tau391-412, tau 14-383, tau14-381, or tau 14-355, or a fragment of any of the foregoing). These antibodies would only recognize, bind or show reactivity with truncated tau, but will not recognize, bind or show reactivity with a normal tau protein (e.g., a full length untruncated htau40). In other words, these antibodies would recognize the neoepitope created by cleavage of tau (i.e., the amino acid sequences of the free N-terminus or the free C-terminus of the peptide created by cleavage of tau), but will not recognize the same sequence of amino acids present in the normal tau protein. These antibodies are therefore not expected to affect the biological functions of the normal tau protein, and, in the preferred embodiments, are expected to clear the peptides created by cleavage of tau and minimize or prevent the neurofiblary tangles formation. These antibodies may therefore be used in the treatment and/or prevention of AD and other tauopathies and in the preparation of pharmaceutical compositions (e.g., vaccines) for the treatment and prevention of these disorders.

It is an additional object of the invention to provide antibodies capable of selectively recognizing an abnormally phosphorylated truncated tau, preferably, tau1-13, tau 14-441, tau14-391, tau391-414, tau1-391, tau1-421, tau14-421, tau14-410, tau391-410, tau14-412, tau391-412, tau 14-383, tau14-381, or tau 14-355, or a fragment of any of the foregoing (e.g., tau phosphorylated at one or more of the following locations: Ser199, Ser202, Ser214, Ser235, Ser396, Ser404, Thr205, Thr231, and Thr212). These antibodies would only recognize, bind or show reactivity with the abnormally phosphorylated truncated tau, but will not recognize, bind or show reactivity with a normal tau protein (i.e., a full length untruncated htau40). In other words, these antibodies would recognize the neoepitope created by the cleavage and abnormal phosphorylation of tau, but would not recognize the same but not phosphorylated sequence of amino acids which is present internally in the normal tau protein. These antibodies are also not expected to affect the biological functions of the normal tau protein and/or inhibit caspase cleavage of tau, and, in the preferred embodiments, are expected to clear the peptides created by cleavage of tau and minimize or prevent the neurofiblary tangles formation, and are used to treat and/or prevent AD and other tauopathies.

In preferred embodiments, antibodies useful in the present invention should be suitable for (i) inhibition, reduction, clearance and elimination of tau truncated at its C-terminus, e.g., at the glutamic acid residue Glu391 or at the aspartic acid residue Asp421, or its N-terminus (e.g., at the aspartic acid residue Asp13), (ii) inhibition, reduction, clearance and elimination of abnormal phosphorylated truncated tau (e.g., tau phosphorylated at Ser396 and/or Ser404), and/or (iii) suitable for the prevention of the neurofiblary tangles formation and/or increased clearance of the neurofiblary tangles, all without affecting the biological functions of the normal tau protein. These antibodies should therefore be suitable for symptomatic treatment and prevention of Alzheimer's disease and other tauopathies and/or for the preparation of a pharmaceutical composition for the treatment of these disorders.

It is a further object of the invention is to provide an isolated immunogenic peptide comprising or consisting of an amino acid sequence which is identical to the amino acid sequence of the neoepitope created by cleavage of tau, e.g., at the glutamic acid residue Glu391, at the aspartic acid residue Asp421, or at the aspartic acid residue Asp13, or a fragment of such peptide, which may be used for inducing an immunogenic response in a mammal, and, in the preferred embodiments, is for use in the treatment and/or prevention of Alzheimer's disease and other tauopathies and/or for the preparation of a pharmaceutical composition for the treatment of these disorders.

It is a further object of the invention to provide a mimotope comprising two peptides fused together with or without spacer residues, the first peptide mimicking the structure of the neoepitope created by cleavage of tau (i.e., the amino acid sequences bound to the free N- or C-terminus portions of a peptide created by cleavage of tau) in a mammal, and the second peptide mimicking the structure of a T cell epitope derived from a different source (e.g., tetanus toxoid), which mimotope is suitable for inducing an immune response in a mammal, and, in the preferred embodiments, is for use in the treatment and/or prevention of AD and other tauopathies and/or in the preparation of a pharmaceutical composition for the treatment of these disorders.

These objects are addressed with the present invention which relates in one preferred aspect to a method of treating or preventing or slowing the progression of a tangle-related behavioral phenotype in a subject, comprising administering to a subject in need of therapy for Alzheimer's disease or other tauopathies of one or more antibodies with a specificity to abnormal forms of soluble truncated tau protein which is or is potentially neurotoxic, said antibody showing no binding and/or reactivity with a normal tau protein. These antibodies are preferably specific for the neoepitope created by cleavage of tau, do not recognize the same sequence of amino acids present internally in the normal tau protein and are administered under conditions and in an amount(s) effective to slow, inhibit and/or reverse a tangle-related behavioral phenotype in the subject. In certain preferred embodiments, the antibodies have specificity to a tau truncated at its C-terminus at the glutamic acid residue Glu391 or at the aspartic acid residue Asp421, and/or a tau truncated at its N-terminus at the aspartic acid residue Asp13 (e.g., tau1-13, tau 14-441, tau14-391, tau391-414, tau1-391, tau1-421, tau14-421, tau14-410, tau391-410, tau14-412, tau391-412, tau 14-383, tau14-381, or tau 14-355, or a fragment of any of the foregoing) and are administered under conditions and in an amount(s) effective to slow, inhibit and/or reverse a tangle-related behavioral phenotype in the subject. In certain embodiments, these antibodies selectively recognize a peptide comprising or consisting an amino acid sequence of amino acids 2-30, or a fragment thereof, of tau; a peptide comprising or consisting of an amino acid sequence of amino acids 380-405, or a fragment thereof, of tau; and/or a peptide comprising or consisting of an amino acid sequence comprising or consisting of amino acids 410-436, or a fragment thereof, of tau; which peptide(s) is(are) created by cleavage of tau; and do not recognize these sequence when these sequences are present internally in the uncleaved/untruncated tau. In some of these embodiments, these antibodies selectively recognize a C-terminal of tau1-421 (ΔTau), e.g., amino acid sequences comprising or consisting of tau416-421, tau417-421, tau418-421, or tau419-421 of ΔTau, do not recognize these sequences in htau40, and do not inhibit caspase cleavage of tau (e.g., at Asp421).

The invention is also related to the administration to a subject in need of therapy for Alzheimer's disease or other tauopathies, of one or more antibodies with a specificity to abnormal forms of tau protein which are conformationally different from normal tau and/or specificity to truncated tau, said antibodies showing no binding and/or reactivity with a normal tau protein. These antibodies are preferably specific for the neoepitope created by cleavage of tau, and do not recognize the same sequence of amino acids when present internally in the normal tau protein. In certain preferred embodiments, the antibodies have specificity to a tau truncated at its C-terminus at the glutamic acid residue Glu391 or at the aspartic acid residue Asp421, and/or a tau truncated at its N-terminus at the aspartic acid residue Asp13 (e.g., tau1-13, tau14-441, tau14-391, tau391-414, tau1-391, tau1-421, tau14-421, tau14-410, tau391-410, tau14-412, tau391-412, tau 14-383, tau14-381, or tau 14-355, or a fragment of any of the foregoing), and are administered under conditions and in an amount(s) effective to prevent aggregation, inhibit aggregation and/or promote clearance of aggregates from the brain of a subject. In some of these embodiments, these antibodies selectively recognize a C-terminal of tau1-421 (ΔTau), e.g., amino acid sequences comprising or consisting of tau416-421, tau417-421, tau418-421, or tau419-421 of ΔTau, do not recognize these sequences in htau40, and do not inhibit caspase cleavage of tau (e.g., at Asp421).

Another aspect of the present invention includes a method of slowing progression of a tangle-related behavioral phenotype in a subject. This method includes administration to a subject in need of therapy for Alzheimer's disease or other tauopathies, of one or more antibodies with specificity to abnormal forms of tau protein (e.g., truncated tau) which are linear or conformationally different from normal tau, said antibodies showing no binding and/or reactivity with a normal tau protein. These antibodies are preferably specific for the neoepitope created by cleavage of tau and do not recognize the same sequence of amino acids present internally in the normal tau protein. These antibodies are therefore not expected to affect the biological functions of the normal tau protein, and, in the preferred embodiments, are expected to clear the peptides created by cleavage of tau and minimize or prevent the neurofiblary tangles formation. In certain preferred embodiments, the antibodies have specificity to a tau truncated at its C-terminus at the glutamic acid residue Glu391 or at the aspartic acid residue Asp421, and/or a tau truncated at its N-terminus at the aspartic acid residue Asp13 (e.g., tau1-13, tau 14-441, tau14-391, tau391-414, tau1-391, tau1-421, tau14-421, tau14-410, tau391-410, tau14-412, tau391-412, tau 14-383, tau14-381, or tau 14-355, or a fragment of any of the foregoing), and are administered under conditions and in an amount(s) effective to slow, inhibit and/or reverse a tangle-related behavioral phenotype in the subject.

In another aspect of the present invention, the antibodies administered selectively recognize a phosphorylated form of the abnormal tau protein (i.e., a truncated tau) and show no binding and/or reactivity with a normal tau protein. These antibodies are therefore not expected to affect the biological functions of the normal tau protein, and, in the preferred embodiments, are expected to clear the peptides created by cleavage of tau and minimize or prevent the neurofiblary tangles formation.

In certain preferred embodiments, the antibodies administered selectively recognize a phosphorylated form of a tau truncated at its C-terminus at the glutamic acid residue Glu391 or at the aspartic acid residue Asp421, or a tau truncated at its N-terminus at the aspartic acid residue Asp13. Preferably, only the linear or conformationally different form of truncated tau protein is selectively recognized by the antibodies of the present invention, and the antibodies show no binding and/or affinity with the normal tau protein (i.e., shows no reactivity to the normal untruncated htau40). In certain embodiments, these antibodies recognize a phosphorylated peptide comprising or consisting an amino acid sequence of amino acids 1-30, or a fragment thereof, of tau; a phosphorylated peptide comprising or consisting of an amino acid sequence of amino acids 380-405, or a fragment thereof, of tau; and/or a phosphorylated peptide comprising or consisting of an amino acid sequence of amino acids 410-436, or a fragment thereof, of tau; which peptide(s) is(are) created by cleavage of tau; and do not recognize these sequences when these sequences are present internally in the uncleaved/untruncated tau. In some of these embodiments, these antibodies selectively recognize a C-terminal of ΔTau, e.g., amino acid sequences comprising or consisting of tau416-421, tau417-421, tau418-421, or tau419-421 of ΔTau, and do not recognize these sequences in htau40.

The invention is further directed to a pharmaceutical composition comprising one or more antibodies with specificity to a tau protein truncated at its C-terminus and/or N-terminus. In certain embodiments, the antibody selectively recognizes a soluble, pre-tangle tau protein truncated at the glutamic acid residue Glu391, or at the aspartic acid residue Asp421, or at its N-terminus at the aspartic acid residue Asp13. In preferred embodiments, the antibodies show no binding and/or affinity with the normal tau protein (i.e., show no reactivity to the normal untruncated tau protein). In some of these embodiments, the antibody is specific for ΔTau, and shows no binding and/or affinity to htau40. In the preferred embodiments, the composition is for the treatment of Alzheimer's disease.

The invention is further directed to a pharmaceutical composition for the treatment and/or prevention of Alzheimer's disease, the composition comprising a plurality of antibodies which are specific for the neoepitope created by cleavage of tau (i.e., the amino acid sequences bound to the free N- or C-terminus portions of a peptide created by cleavage of tau), and do not recognize the same sequence of amino acids when present internally in the normal tau protein. In the preferred embodiments, the neoepitope comprises or consists of a sequence selected from SEQ ID No: 7-94 or 116, or a fragment thereof.

The invention is further directed to antibodies that recognize either linear or conformational free-end epitopes of truncated tau. In preferred embodiments, the antibodies show no binding and/or affinity with the normal tau protein (i.e., shows no reactivity to the normal untruncated tau protein).

The invention is also directed in part to an immunogenic peptide (e.g., an isolated immunogenic peptide), comprising a portion or fragment of a truncated tau, e.g., expressed by a virus or bacteria, incorporated into a genome or episome of the virus or bacteria (i.e., the virus or bacteria comprises a gene encoding for the immunogenic peptide), isolated from a mammal, synthesized chemically, or produced using recombinant DNA techniques, as part of an immunogenic composition. In all of these embodiments, the immunogenic portion of the peptides comprises a linear sequence of two, three, four, five, six, seven, eight, nine, or ten amino acids covalently bound to a free N-terminus or a free C-terminus of a truncated tau, which sequence is identical to the sequence of the first two, three, four, five, six, seven, eight, nine or ten amino acids or the last two, three, four, five, six, seven, eight, nine or ten amino acids of a peptide (e.g., ΔTau) created by cleavage of tau. In certain preferred embodiments, the immunogenic peptide comprises a portion of a tau protein truncated at its C-terminus at the glutamic acid residue Glu391, a portion of the tau protein truncated at its C-terminus at the aspartic acid residue Asp421, a tau truncated at its N-terminus at the aspartic acid residue Asp13, or combinations thereof (e.g., tau1-13, tau14-441, tau14-391, tau391-414, tau1-391, tau1-421, tau14-421, tau14-410, tau391-410, tau14-412, tau391-412, tau 14-383, tau14-381, or tau 14-355, or a fragment of any of the foregoing). The immunogenic portion of the peptide, in the preferred embodiments, comprises or consists of an amino acid sequence which is selected from SEQ ID Nos: 7-94 or 116, or a fragment thereof. The immunogenic peptide is capable of inducing an immunogenic response in a mammal, and, preferably, is for use in the treatment and/or prevention of Alzheimer's disease and other tauopathies and/or in the preparation of a pharmaceutical composition for the treatment of these disorders. In the preferred embodiments, the immunogenic response is the production of the neoepitope-specific antibodies described herein, e.g., in-situ of a living mammal (e.g., human).

The invention is also directed to a mimotope comprising two peptides fused together with or without spacer residues, the first peptide mimicking the structure of the neoepitope created by cleavage of tau (i.e., the amino acid sequences bound to the free N- or C-terminus portions of a peptide created by cleavage of tau) in a mammal, and the second peptide mimicking the structure of a T cell epitope derived from a different source (e.g., tetanus toxoid), which mimotope is suitable for inducing an immune response in a mammal. In the preferred embodiments, the immunogenic response is the production of the neoepitope-specific antibodies described herein. In the preferred embodiments, is for use in the treatment and/or prevention of Alzheimer's disease and other tauopathies and/or in the preparation of a pharmaceutical composition for the treatment of these disorders.

The invention is also directed to a pharmaceutical composition comprising a mimotope comprising two peptides fused together with or without spacer residues, the first peptide mimicking the structure of the neoepitope created by cleavage of tau (i.e., the amino acid sequences bound to the free N- or C-terminus portions of a peptide created by cleavage of tau) in a mammal, and the second peptide mimicking the structure of a T cell epitope derived from a different source (e.g., tetanus toxoid), which mimotope is suitable for inducing an immune response in a mammal. In the preferred embodiments, the immunogenic response is the production of the neoepitope-specific antibodies described herein. The composition is used for inducing an immunogenic response in a mammal, and, in the preferred embodiments, for the treatment and/or prevention of Alzheimer's disease and other tauopathies and/or in the preparation of a pharmaceutical composition for the treatment of these disorders.

The invention is further directed to a pharmaceutical composition comprising (i) a mimotope comprising two peptides fused together with or without spacer residues, the first peptide mimicking the structure of the neoepitope created by cleavage of tau (i.e., the amino acid sequences bound to the free N- or C-terminus portions of a peptide created by cleavage of tau) in a mammal, and the second peptide mimicking the structure of a T cell epitope derived from a different source (e.g., tetanus toxoid); (ii) a mimotope comprising two peptides fused together with or without spacer residues, the first peptide mimicking the structure of the neoepitope created by cleavage of APP (i.e., the amino acid sequences bound to the free N- or C-terminus portions of a peptide created by cleavage of APP) in a mammal, and the second peptide mimicking the structure of a T cell epitope derived from a different source (e.g., tetanus toxoid). The composition is used for inducing an immunogenic response in a mammal, and in the preferred embodiments, is for use in the treatment and/or prevention of Alzheimer's disease and other tauopathies and/or in the preparation of a pharmaceutical composition for the treatment of these disorders.

The invention is further directed to a method of treating, preventing, and/or slowing progression of a tangle-related behavioral phenotype in a subject, comprising administering to a subject in need of such treatment one or more free end-specific antibodies generated from synthetic peptides comprising immunogenic linear or conformational sequences of abnormal tau, the antibodies that selectively recognize free ends of truncated tau (e.g., soluble truncated tau), and show no reactivity (binding or affinity to normal untruncated tau). In certain embodiments, these antibodies may (i) inhibit or slow down, e.g., tau polymerization and formation of neurofibrillary tangles, and (ii) promote clearance of abnormal tau and/or the agents responsible for formation of abnormal tau.

Another aspect of the present invention includes a method of preventing or treating Alzheimer's Disease or other tauopathies in a subject, via the administration of a truncated tau protein, preferably a tau truncated at its C-terminus at the glutamic acid residue Glu391 or at the aspartic acid residue Asp421 (e.g., ΔTau), and/or a tau truncated at its N-terminus at the aspartic acid residue Asp13, or a fragment of any of the foregoing, under conditions and in the amounts to induce in-situ production of free end-specific antibodies to the truncated protein(s) and effective to prevent or treat Alzheimer's Disease or other tauopathies. In the preferred embodiments, the free end-specific antibodies selectively recognize a peptide comprising or consisting an amino acid sequence of amino acids 2-30, or a fragment thereof, of tau; a peptide comprising or consisting of an amino acid sequence of amino acids 380-405, or a fragment thereof, of tau; and/or a peptide comprising or consisting of an amino acid sequence of amino acids 410-436, or a fragment thereof, of tau; which peptide(s) is(are) created by cleavage of tau; but do not recognize these sequence when these sequences are present internally in the uncleaved/untruncated tau. In some of these embodiments, the method comprises administration of ΔTau, or a fragment thereof, and the antibodies produced in response to this administration selectively recognize a C-terminal of ΔTau, and do not recognize these sequences in htau40.

Another aspect of the present invention includes a method of slowing progression of a tangle-related behavioral phenotype in a subject. This method includes administration to a subject in need of therapy for Alzheimer's disease or other tauopathies, of a truncated tau protein, preferably a tau truncated at its C-terminus at glutamic acid residue Glu391 or at the aspartic acid residue Asp421, and/or a tau truncated at its N-terminus at the aspartic acid residue Asp13, under conditions and in the amounts to induce in situ production of free end-specific antibodies to the truncated protein(s) and effective to slow, inhibit and/or reverse a tangle-related behavioral phenotype in a subject.

The invention is further directed in part to a gene therapy vector operably linked to a gene encoding for an immunogen, the immunogen comprising a portion of a truncated tau protein. In certain embodiments, the truncated tau protein is selected from the group consisting of a tau protein truncated at its C-terminus at the glutamic acid residue Glu391, a tau protein truncated at the aspartic acid residue Asp421, a tau truncated at its N-terminus at the aspartic acid residue Asp13, and combinations thereof (e.g., tau1-13, tau 14-441, tau14-391, tau391-414, tau1-391, tau1-421, tau14-421, tau14-410, tau391-410, tau14-412, tau391-412, tau 14-383, tau14-381, or tau 14-355, or a fragment of any of the foregoing). In some of these embodiments, the immunogen comprises or consists of the last ten, nine, eight, seven, six, five, four or three amino acids of ΔTau.

The invention is also directed in part to a pharmaceutical composition comprising naked DNA encoding an immunogen comprising a portion of the protein selected from the group consisting of a tau protein truncated at its C-terminus at the glutamic acid residue Glu391, a tau protein truncated at the aspartic acid residue Asp421, a tau truncated at its N-terminus at the aspartic acid residue Asp13, and combinations thereof (e.g., tau1-13, tau 14-441, tau14-391, tau391-414, tau1-391, tau1-421, tau14-421, tau14-410, tau391-410, tau14-412, tau391-412, tau 14-383, tau14-381, or tau 14-355, or a fragment of any of the foregoing, and combinations thereof).

The invention is further directed to a vaccine which comprises a portion of one or more abnormal or truncated tau protein(s) as set forth herein in combination with a pharmaceutically acceptable carrier, or a vaccine which comprises one or more antibodies specific for a portion(s) of an abnormal or truncated tau protein(s) as set forth herein and capable of crossing the blood brain barrier in combination with a pharmaceutically acceptable carrier. In the preferred embodiments, the vaccine is for the treatment of Alzheimer's disease, and comprises a mimotope fused with a bacterial peptide, the mimotope mimicking the structure of the neoepitope created by cleavage of tau (i.e., the amino acid sequences bound to the free N- or C-terminus portions of a peptide created by cleavage of tau) in a mammal, and the bacterial peptide comprising or consisting of a natural bacterial tetanus toxoid or equivalent. The use of the mimotope, in the preferred embodiments, prevents a possibility of an autoimmune response which does not apply to a bacterial peptide. The vaccine may or may not comprise an additional mimitope comprising a mimotope mimicking the structure of the neoepitope created by cleavage of APP (i.e., the amino acid sequences bound to the free N- or C-terminus portions of a peptide created by cleavage of APP) in a mammal, the additional mimitope fused, with or without spacer residues, to a bacterial peptide which is a natural bacterial tetanus toxoid or equivalent. The vaccine is for inducing an immunogenic response in a mammal. In the preferred embodiments, the immunogenic response is the production of the neoepitope-specific antibodies described herein. In the preferred embodiments, the vaccine is for use in the treatment and/or prevention of Alzheimer's disease and other tauopathies and/or in the preparation of a pharmaceutical composition for the treatment of these disorders.

The invention is further directed to a vaccine which comprises a mimotope mimicking the structure of the neoepitope created by cleavage of tau in a mammal, the mimotope fused, with or without spacer residues, to a bacterial peptide comprising or consisting of a natural bacterial tetanus toxoid or equivalent, wherein the neoepitope comprises or consists of an amino acid sequence of amino acids 1-30, or a fragment thereof, of tau; a peptide comprising or consisting of an amino acid sequence of amino acids 380-405, or a fragment thereof, of tau; and/or a peptide comprising or consisting of an amino acid sequence of amino acids 410-436, or a fragment thereof, of tau; and the mimotope is suitable for inducing an immunogenic response in a mammal. In some of these embodiments, the neoepitope comprises or consists of amino acids 16-421, 17-421, 18-421, or 19-421 of ΔTau. In the preferred embodiments, the vaccine is for use in a pharmaceutical composition for the treatment and/or prevention of Alzheimer's disease and other tauopathies.

The invention is further directed to a vaccine which comprises (i) a mimotope mimicking the structure of the neoepitope created by cleavage of tau in a mammal (e.g., at Asp421), the mimotope fused, with or without spacer residues, to a bacterial peptide comprising or consisting a structure of a T cell epitope derived from a different source (e.g., tetanus toxoid); and (ii) a mimotope mimicking the structure of the neoepitope created by cleavage of Aβ in a mammal, fused, with or without spacer residues, to a bacterial peptide comprising or consisting the structure of a T cell epitope derived from a different source (e.g., tetanus toxoid). The T cell epitope in the first mimotope and the second mimotope may be the same or different. In certain embodiments, the T cell epitope in the first mimotope and in the second mimotope comprise the same structure as a well-studied tetanus toxoid promiscuous epitope of SEQ ID No: 95 (Ho et al., 1990; Panina-Bordignon et al. 1989), as this epitope is known to work in a number of diverse human genetic backgrounds (Valmori et al., 1992 and 1994). In the preferred embodiments, the vaccine is for the treatment and/or prevention of Alzheimer's disease and other tauopathies.

In certain embodiments, the invention is directed to a pharmaceutical composition comprising a chimeric peptide(s) comprising (i) a 2-10 or 2-6 amino acid residue from the free N- or C-terminus of a truncated tau (e.g., ΔTau) fused together with or without a spacer to (ii) a promiscuous T helper cell epitope derived from a different source than the amino acid residue. The truncated tau is selected from the group consisting of tau truncated at its C-terminus at the glutamic acid residue Glu391 or at the aspartic acid residue Asp421, or a tau truncated at its N-terminus, e.g., at the aspartic acid residue Asp13. In certain embodiments, the truncated tau is ΔTau. In certain embodiments, the T helper cell epitope is the well-studied tetanus toxoid promiscuous epitope of SEQ ID No: 95. The composition comprising an immunizing effective amount of the chimeric peptide or peptides and a pharmaceutically acceptable carrier, excipient, diluent, or auxiliary agent may then be administered to a mammal (e.g., human) to induce formation of antibodies which are specific for the neoepitope created by cleavage of tau (i.e., the amino acid sequences bound to the free N- or C-terminus portions of a peptide created by cleavage of tau), and do not recognize the same sequence of amino acids when present in the normal tau protein.

The promiscuous T helper cell epitope may be a T cell epitope derived from, e.g., tetanus toxin, pertussis toxin, diphtheria toxin, measles virus F protein, hepatitis B virus surface antigen, *Chlamydia* trachomitis major outer membrane protein, *Plasmodium falciparum circumsporozoite*, *Schistosoma mansoni* triose phosphate isomerase, or *Escherichia coli* TraT. In the preferred embodiments the T cell epitope is a well-studied tetanus toxoid promiscuous epitope of SEQ ID No: 95 (Ho et al., 1990; Panina-Bordignon et al. 1989), as this epitope is known to work in a number of diverse human genetic backgrounds (Valmori et al., 1992 and 1994).

Further aspects of the invention are directed to a truncated tau protein wherein the last 20 amino acids at the C-terminal or N-terminal of tau are taken off and are not present in the truncated protein (e.g., ΔTau); the immunogenic portion of the truncated tau protein; genes encoding for truncated protein and/or peptide containing the immunogenic portion of the protein; antibodies selective/specific for the truncated protein-monoclonal, polyclonal, chimeric, recombinant, humanized, and portions of any of the foregoing; produced in situ and ex situ; transgenic "animals" secreting antibodies selective/specific for the truncated protein; active immunization (administration of truncated protein or immunogenic portions thereof to a subject); passive immunization (administration of antibodies in accordance with the invention to a subject); and pharmaceutical formulations for active and passive immunizations.

The immunogenic fragment of the truncated tau, in certain embodiments, comprises a linear sequence of two, three, four, five, six or seven amino acids covalently bound to a free N-terminus or a free C-terminus, which sequence is identical to the sequence of the first two, three, four, five, six or seven amino acids or the last two, three, four, five, six or seven amino acids of a peptide (e.g., ΔTau) created by cleavage of tau. In certain embodiments, the peptide comprises or consists of an amino acid sequence of amino acids 1-30, or a fragment thereof, of tau; an amino acid sequence of amino acids 380-405, or a fragment thereof, of tau; or an amino acid sequence of amino acids 410-436, or a fragment thereof. In some of these embodiments, the sequence comprises or consists of amino acids 16-421, 17-421, 18-421, or 19-421 of ΔTau.

In one embodiment, the immunogenic fragment of the truncated tau comprises a linear sequence of at least five amino acids of the tau protein which ensures that the specific free amino group at the N-terminus constitutes an essential part of the epitope recognized by the new linear epitope free-end specific antibody. In other embodiments, fragments of truncated tau have at least the last 20, 30 or 45 amino acids of the truncated tau, and linear epitope free-end specific or conformation-specific antibodies are generated. In certain further preferred embodiments, the invention is directed to a vaccine which is a combination of a composition providing immunization against cleavage products of tau (i.e., truncated tau protein) and a composition providing immunization against cleavage products of APP.

In certain preferred embodiments, the composition providing immunization against truncated tau protein comprises a chimeric peptide(s) comprising (i) a 2-10 or 2-6 amino acid residue from the free N- or C-terminus of a truncated tau (e.g., ΔTau) fused together with or without a spacer to (ii) a promiscuous T helper cell epitope derived from a different source than the amino acid residue; and the composition providing immunization against cleavage product of APP comprises a chimeric peptide(s) comprising (i) a 2-10 or 2-6 amino acid residue from the free N or C terminus of a truncated APP (e.g., $A\beta_{1-40}, A\beta_{1-42}, A\beta_{1-43}$, etc.) fused with or without a spacer to (ii) a promiscuous T helper cell epitope derived from a different source than the amino acid residue. The T cell epitope in the composition providing immunization against cleavage products of tau and in the composition providing immunization against cleavage products of APP may be the same or different. In certain embodiments, the T cell epitope of both compositions comprises the well-studied tetanus toxoid promiscuous epitope of SEQ ID No: 95.

"Antibody" as used herein is meant to include intact molecules and fragments thereof, as well as synthetic and biological derivatives thereof, such as for example Fab, F(ab'$_2$ an F$_1$, fragments-free or expressed, e.g., on the surface of filamentous phage on pIII or pVIII or other surface proteins, or on the surface of bacteria, which are capable of binding an antigen. Fab, F(ab'$_2$ and F$_1$, fragments lack the F$_C$ fragments of intact antibody, clear more rapidly from the circulation and may have less non-specific tissue binding of antibody. Furthermore F$_1$, antibody (often called as minibody) can be easily engineered to carry on its C-terminus specific tracer and used for early intravital presymptomatic diagnosis of AD, since stage I, II and III of AD that is recognized by the antibodies according to the present invention is not associated with intellectual decline. The term antibody encompasses, e.g., chimeric and humanized antibodies. The antibody may be a monoclonal antibody or a polyclonal antibody. It also encompasses recombinant antibodies. The antibodies may preferably be linear antibodies, or conformational antibodies.

The terms "does not bind," "does not recognize," and "does not show reactivity" as used in the present application mean either that an antibody shows no detectible binding with a peptide or protein (e.g., htau40), or that the antibody's equilibrium constant KD with the peptide or protein is from $1 \times 10^{-4}$ molar to $1 \times 10^{-6}$ M, as measured by a surface plasmon resonance assay utilizing peptide captured on streptavidin chip.

The terms "binds specifically," "specifically recognize," "selectively recognizes," "having specificity," and "specific for" as used in the present specification mean that an antibody binds the antigen it is specific for (e.g., the neopitope created by cleavage of htau at Asp421) with equilibrium constant KD of from $1 \times 10^{-9}$ M to $1 \times 10^{-11}$ M, as measured by a surface plasmon resonance assay utilizing peptide captured on strepvidin chip; and has an equilibrium constant KD with other peptides or proteins (e.g., htau40) which is from $1 \times 10^{-4}$ M to $1 \times 10^{-6}$ M, as measured by the surface plasmon resonance assay utilizing peptide captured on strepvidin chip, or shows no detectible binding with these other peptides or proteins.

The term "tau protein" as used in the present application refers to the any one of known isoforms of tau (e.g., longest isoform of human microtubule associated protein tau containing all alternatively spliced inserts as described in M. Goedert et al., 1989 (htau40)).

The term "humanized antibody" is referred herein above to an antibody in which the complementary-determining regions (CDRs) of a mouse or other non-human antibody are grafted onto a human antibody framework. By human antibody framework is meant the entire human antibody excluding the CDRs.

The term "chimeric antibody" refers to an antibody in which the whole of the variable regions of a mouse or rat antibody are expressed along with human constant regions.

The term "treating" is referred hereinabove to delay or prevent the onset slow the progression or ameliorate the symptoms related to Alzheimer's disease or other disease or disorder characterized by Aβ deposition.

The term "mimotope" as used in the present application is a macromolecule, often a peptide (i.e., an immunogenic peptide or immunogen), which mimics the structure of an epitope.

The term "tauopathy" refers to tau-related disorders or conditions, e.g., Alzheimer's Disease, Progressive Supranuclear Palsy (PSP), Corticobasal Degeneration (CBD), Pick's Disease, Frontotemporal dementia and Parkinsonism associated with chromosome 17 (FTDP-17), Parkinson's disease, stroke, traumatic brain injury, mild cognitive impairment and the like.

The terms "immunogen" refers to a molecule capable of being bound by an antibody, a B cell receptor (BCR), or a T cell receptor (TCR) if presented by MHC molecules. The term "immunogen", as used herein, also encompasses T-cell epitopes. An immunogen can additionally be capable of being recognized by the immune system and/or being capable of inducing a humoral immune response and/or cellular immune response leading to the activation of B- and/or T-lymphocytes. This may, however, require that, at least in certain cases, the immunogen contains or is linked to a T helper cell epitope and is given an adjuvant. An immunogen can have one or more epitopes (e.g., B- and T-epitopes). The "immunogen" as used herein may also be mixtures of several individual immunogens. The term "immunogen" encompasses, but are not limited to, peptides.

As used herein, the term "phosphorylated" in reference to an amino acid residue refers to the presence of a phosphate group on the side chain of the residue where a hydroxyl group is otherwise normally present. Such phosphorylation typically occurs as a substitution of the hydrogen atom from a hydroxyl group for a phosphate group (—PO$_3$H$_2$). As recognized by those of skill in the art, depending on the pH of the local environment, this phosphate group can exist as an uncharged, neutral group (—PO$_3$H$_2$), or with a single (—PO$_3$H$^-$), or double (—PO$_3^{2-}$) negative charge Amino acid residues that can typically be phosphorylated include the side chains of serine, threonine, and tyrosine.

The articles "a" and "an" are used herein to refer to one or to more than one (i.e., to at least one) of the grammatical object of the article. By way of example, "an element" means one element or more than one element. Further, unless otherwise required by context, singular terms shall include pluralities and plural terms shall include the singular unless the content clearly dictates otherwise.

The term "isolated" with respect to an immunogenic peptide refer to a peptide that by virtue of its origin or source of derivation (1) is not associated with naturally associated components that accompany it in its native state, (2) is substantially free of other proteins from the same species, (3) is expressed by a cell from a different species, or (4) does not occur in nature. Thus, a peptide that is chemically synthesized or synthesized in a cellular system different from the cell from which it naturally originates will be "isolated" from its naturally associated components. A peptide may also be rendered substantially free of naturally associated components by isolation, using protein purification techniques well known in the art.

The term "neoepitope" as used in the present application refers to a non-naturally occurring epitope created as a result of cleavage of a pre-cursor protein (e.g., tau, APP, etc.) and/or phosphorylated Tau.

BRIEF DESCRIPTION OF THE DRAWINGS

FIG. 1 shows a mechanism for the formation of neurofiblary tangles.

DETAILED DESCRIPTION OF THE INVENTION

A proposed model for the formation of neurofiblary tangles stipulates that apoptotic stimuli (e.g., $A\beta_{1-42}$) results in caspase-cleavage of tau, e.g., at amino acid Asp421, which leads to increased pathological formation of neurofibrillary filaments (NTFs) and paired helical filaments (PHFs), as well as pathological tau aggregation. For example, Rissman et al., J. Clin. Invest. 114: 121-130 (2004), propose the mechanism for the formation of neurofiblary tangles shown in FIG. 1. According to Rissman et al., exposure to apoptotic stimuli such as $A\beta_{1-42}$ result in caspase-cleavage of tau after Asp421 (I); caspase-cleaved tau rapidly adopts the MC1 conformational epitope (II), which leads to increased filament formation and tau aggregation (III); to compensate for tau aggregation, tau may subsequently be hyperphosphorylated and disassociate from microtubule (IV); and, as a result, caspase cleavage of tau may lead to PHF formation (V).

Increased formation of pathological NTFs and PHFs and pathological tau aggregation is commonly seen in mammals suffering from progressive neurodegenerative disorders (e.g., AD and other tauopathies) and is associated with loss of cognitive and behavioral functions in mammals. Since cleavage of tau by executioner caspases after exposure to an apoptotic stimuli (e.g., Aβ) is thought to result in a form that is especially prone to tangle formation, an inhibition or decrease of the caspase-cleaved tau should therefore decrease and/or prevent formation of pathological NTF and PHF and pathological tau aggregation Inhibition or decrease of the caspase-cleaved tau should also be useful in the treatment and/or prevention of the progressive neurodegenerative diseases.

The present invention is directed to antibodies specific for free ends of truncated tau (e.g., caspase-cleaved htau40 (e.g., ΔTau) and showing no binding and/or reactivity with the normal tau and uses of these antibodies in the treatment and/or prevention of AD and other tauopathies, in clearance of soluble truncated tau from the brain of a patient suffering from AD or another tauopathy, and in preparation of pharmaceutical compositions for the treatment and/or prevention of these disorders. These antibodies would recognize the neoepitope created by cleavage of tau (e.g., C-terminus of ΔTau), but will not recognize the same sequence of amino acids present in the normal tau protein (e.g., htau40), which lacks the neoepitope. These antibodies are not expected to affect the biological functions of the normal tau protein, and are expected to clear the peptides created by cleavage of tau and minimize or prevent the pathological NTFs and PHFs formation and pathological tau aggregation. These antibodies are also not expected to inhibit caspase cleavage of htau40 at Asp421.

The antibodies that can selectively recognize the free end(s) (neoepitope(s)) of soluble tau peptides (e.g., ΔTau) formed by the cleavage of tau (e.g., htau40), while not recognizing and showing no reactivity with full length tau protein, are believed to be capable of directly inhibiting polymerization of tau and/or formation of NTFs, PHFs and/or other pathological tau precursors. One significance of using these neoepitope-specific antibodies is that these antibodies may be used to clear soluble neurotoxic tau before NTFs and PHFs are formed and/or before tau is pathologically aggregated or polymerized, and/or before these neoepitopes become inaccessible or less accessible to the antibodies, and/or the neurological damage is done.

It is specifically contemplated that these antibodies may be used for (i) inhibition, reduction, clearance and elimination of tau truncated at its C-terminus, e.g., at the glutamic acid residue Glu391 or at the aspartic acid residue Asp421, or its N-terminus (e.g., at aspartic acid residue Asp421), (ii) inhibition, reduction, clearance and elimination of abnormal phosphorylated truncated tau (e.g., tau phosphorylated at Ser396 and/or Ser404), and/or (iii) prevention of NTFs and/or PHFs formation and/or increased clearance of NTFs and PHFs, all without affecting the biological functions of the normal tau protein (e.g., htau40).

Two neoepitope-specific antibodies specifically contemplated by the present invention for the uses described above are: an antibody that is specific for free C-terminus end of tau truncated at Asp421 (i.e., ΔTau), and shows no binding and/or reactivity with the normal tau (e.g., htau40); and an antibody that is specific for free C-terminus end of tau14-421, and shows no binding and/or reactivity with the normal tau protein. In the preferred embodiments, these antibodies do not inhibit caspase cleavage of htau40 at Asp421.

It is believed that, as of the effective filing date of the present application, there is no reports in the literature of using antibodies specific or selective for soluble pre-tangle truncated tau, e.g., at Asp421, Glu391 and or Asp13 and showing no specific binding or reactivity to full length tau protein (or antibodies having three-dimensional structures similar to the antibodies specific for soluble pre-tangle truncated tau at Asp421, Glu391 and or Asp13) in the treatment or prevention of AD and other tauopathies. The use of these neoepitope-specific antibodies for treating AD or another tauopathy is not obvious, e.g., because the literature does not report where the soluble truncated forms of tau exist in the cell and if such forms and locations are accessible to antibodies. This approach also does not depend on producing conformational antibodies to preformed tau tangles that are already causing damage, and is intended to address the problem before the pathological NTFs and/or PHFs are formed and tau is pathologically aggregated.

The present invention also encompasses a method of treating or preventing Alzheimer's disease or other tauopathies in a subject. This method includes administering antibodies to truncated tau proteins selectively recognizing these truncated tau proteins, or portions of the truncated tau proteins, to a patient under conditions and in the amounts effective to treat or prevent Alzheimer's Disease or other tauopathies. The antibodies may be administered, e.g., intravenously, subcutaneously, nasally, buccally, transdermally, etc., as described in more detail below. In certain preferred embodiments, the antibodies selectively recognize soluble pre-tangle truncated tau, and show no binding and/or reactivity with normal tau. The antibodies should therefore facilitate clearance of the truncated tau and should not affect the biological functions of the normal tau. In certain embodiments, the administered antibodies block aggregation of ΔTau directly (e.g., by attaching to the C-terminus of ΔTau and, thereby, directly interfering with the ability of the C-terminus of ΔTau to interact with outer proteins and peptides). The antibodies blocking tau aggregation directly will, preferably, have a low off rate.

In one aspect, the present invention includes a method of promoting clearance of tau aggregates from the brain of a subject. This method includes administering antibodies with a specificity to abnormal (truncated) forms of tau protein (or portions of the abnormal (truncated) forms of tau protein) which may or may not be conformationally different from normal tau, the antibodies being non-specific for a normal tau protein (show no affinity, binding or reactivity with normal tau), to a mammal (e.g., a human patient). In certain preferred embodiments, the antibodies have specificity to a tau truncated at its C-terminus at the glutamic acid residue Glu391 or at the aspartic acid residue Asp421. In other preferred embodiments, the antibodies have specificity to a tau truncated at its N-terminus, e.g., at amino acid Asp13. In additional preferred embodiments, the antibodies have specificity to ΔTau (tau1-421) and/or tau14-421. The aggregates to be cleared include, e.g., neurofibrillary tangles or their pathological tau precursors. Neurofibrillary tangles are often associated with neurodegenerative diseases including, for example, Alzheimer's disease, hereditary frontotemporal dementia and parkinsonism linked to chromosome 17 (FTDP-17), Pick's disease, sporadic corticobasal degeneration, and progressive supranuclear palsy. The antibodies may be administered, e.g., intravenously, subcutaneously, nasally, buccally, transdermally, etc., as described in more detail below.

Another aspect of the present invention includes a method of slowing the progression of or reversing a tangle-related behavioral phenotype in a subject. This method includes administering a truncated tau or a portion of the truncated tau (e.g., as a vaccine), or antibodies specifically recognizing a truncated tau or a portion of a truncated tau, under conditions and in the amounts effective to slow or reverse a tangle-related behavioral phenotype in a subject. The truncated tau, a portion of truncated tau, or antibodies may be administered, e.g., intravenously, subcutaneously, nasally, buccally, transdermally, etc., as described in more detail below.

In certain preferred embodiments, the invention is directed to administering antibodies with a specificity to abnormal (truncated) forms of tau protein (or portions of the abnormal (truncated) forms of tau protein) which may or may not be conformationally different from normal tau, said antibody being non-specific for a normal tau protein (show no binding or reactivity with normal tau), e.g., to a human patient. Preferably, these antibodies recognize either linear or conformational free-end epitopes of truncated tau. In certain preferred embodiments, these free end-specific antibodies inhibit tau polymerization. The antibodies may be administered, e.g., intravenously, subcutaneously, nasally, buccally, transdermally, etc., as described in more detail below.

As stated by Kovacech et al., "Tau Truncation is a Productive Posttranslational Modification of Neurofibrillary Degeneration in Alzheimer's Disease", Current Alzheimer Research Vol. 7 pp. 708-716 (2010), taking into account that a range of C-terminal tau truncations can promote tau assembly into paired helical filaments (PHF's), various N- and C-terminally truncated tau proteins exert abnormal microtubule assembly, and both Glu391 and Asp421 truncated tau molecules induced similar levels of apoptotic cells, many of the proteins present in the truncated tau proteome of the diseased brain can serve as inducers of tau neurofibrillary degeneration. Tau mutations are known to alter the conformation of the protein and lead to its higher and faster phosphorylation in vitro. Truncation of tau can even induce its hyperphosphorylation. While the temporal role of phosphorylation in the development of tau pathology has not been determined, Kovacech et al. report that the in vivo model of tauopathy based on the truncated tau protein clearly shows that truncation is a "productive" modification that can initiate tau neurofibrillary degeneration. Kovacech et al. further state that immunohistochemical mapping of the distribution of Asp421 and Glu391 truncated tau in AD brains indicated that these epitopes appear in a specific temporal order of the tangle development, and propose that the neurofibrillary tangles (NFTs) pass through several stages during which tau changes conformation several times and becomes progressively truncated at both N- and C-termini; initially, full length tau molecules being assembled in pre-tangle neurons exhibiting the conformational epitope Alz50, and truncation events proposed to ensue soon after the tangle formation, tau being first truncated at the Asp421 cleavage point (e.g., by caspase-3) and later cleaved further at Glu391.

Asuni et al. 2007 reported clearance of tau from the brain using immunotherapy. The result was surprising and counterintuitive because the target was thought to be mainly intracellular and mainly in the cytoplasm and therefore generally inaccessible to antibodies generated or delivered outside the cell. Various mechanisms have been postulated but none definitively demonstrated to explain how immunotherapy works in this case. One suggestion was that the tau protein that was cleared from the brain of transgenic mice, was in fact extracellular. Another suggestion was that the tau-antibody complex formed in a vacuolar compartment that is linked to the secretory-endosomal pathway. A third idea was that antibodies get inside degenerating nerve cells (See review by Sigurdsson, Current Alzheimer's Research 2009, 6, 446-450).

Truncated Tau

The abnormal forms of tau proteins which are the subject of the present invention typically are truncated tau proteins (e.g. caspase-cleaved tau proteins), most preferably tau truncated at its C-terminus at the glutamic acid residue Glu391 or at the aspartic acid residue Asp421, or a tau truncated at its N-terminus, e.g., at the aspartic acid residue Asp13 (e.g., tau1-13, tau14-441, tau14-391, tau391-414, tau1-391, tau1-421, tau14-421, tau14-410, tau391-410, tau14-412, tau391-412, tau 14-383, tau14-381, or tau14-355, or a fragment of any of the foregoing). In certain embodiments, the truncated tau protein is tau1-421 (ΔTau), or a C-terminal fragment thereof. These abnormal tau proteins may be conformationally different from normal tau and are sometimes referred to as "tauons" (see, e.g., U.S. Patent Publication No. U.S. 2004/0082763, hereby incorporated by reference in its entirety). Different conformations compared to normal human tau may be attributed pathologically to abnormal truncation at the N-terminus or at the C-terminus or at both termini of the tau molecule.

These abnormal or truncated tau proteins or fragments thereof may be used as immunogens or mimotopes to generate antibodies specific for the truncated tau protein (e.g., neoepitopes created by cleavage of tau at, e.g., Asp421) and non-specific for untruncated tau, in-situ and ex-situ of a subject's brain, and/or administered to a subject to induce formation of the neoepitope-specific antibodies in the subject. For example, the above-mentioned truncated tau proteins may be administered to a mammal (e.g., a human patient) who may be susceptible to the formation of neurofibrillary tangles in order to raise antibodies against such truncated tau proteins if and when they form in vivo. In certain embodiments, the truncated tau protein comprises an amino acid sequence of amino acids 1-30, or a fragment thereof, of tau; an amino acid sequence of amino acids 380-405, or a fragment thereof, of tau; or an amino acid sequence of amino acids 410-436, or a fragment thereof, of tau. In certain embodiments, the truncated tau protein is tau1-421 (ΔTau), or a C-terminal fragment thereof (e.g., tau411-421, tau412-421, tau413-421, tau414-421, tau 415-421, tau416-421, tau417-421, or tau418-421). In some of these embodiments, the truncated tau protein is phosphorylated at Ser412 and/or Ser413.

In certain embodiments, the truncated tau comprises or consists of tau1-13, tau14-441, tau14-391, tau391-414, tau1-391, tau1-421, tau 14-421, tau14-410, tau391-410, tau14-

412, tau391-412, tau14-383, tau14-381, tau 14-355, or a fragment of any of the foregoing, of any one of the six isoforms of the human tau protein. The truncated tau, in certain embodiments, may be phosphorylated at one or more of the following: Ser199, Ser202, Ser214, Ser235, Ser396, Ser404, Thr205, Thr231, and Thr212, if present.

The truncated tau protein described above can be derived from any one of the six isoforms of the human tau protein or a segment thereof. Tau protein has 0, 1, or 2 N-terminal inserts resulting from the splicing of exons two and three, and either 3 or 4 microtubule-binding domains resulting from the splicing of exon ten. In certain embodiments, the truncated tau protein is derived from the longest isoform of tau (i.e., htau40). The amino acid sequences corresponding to the isoforms of the human tau protein of the present invention are given in SEQ ID NOs: 1-6.

SEQ ID NO: 1, the longest tau isoform, htau40, containing two N-terminal inserts and four microtubule binding (2N4R) domains, is as follows:

```
MAEPRQEFEV MEDHAGTYGL GDRKDQGGYT MHQDQEGDTD AGLKESPLQT PTEDGSEEPG    60

SETSDAKSTP TAEDVTAPLV DEGAPGKQAA AQPHTEIPEG TTAEEAGIGD TPSLEDEAAG   120

HVTQARMVSK SKDGTGSDDK KAKGADGKTK IATPRGAAPP GQKGQANATR IPAKTPPAPK   180

TPPSSGEPPK SGDRSGYSSP GSPGTPGSRS RTPSLPTPPT REPKKVAVVR TPPKSPSSAK   240

SRLQTAPVPM PDLKNVKSKI GSTENLKHQP GGGKVQIINK KLDLSNVQSK CGSKDNIKHV   300

PGGGSVQIVY KPVDLSKVTS KCGSLGNIHH KPGGGQVEVK SEKLDFKDRV QSKIGSLDNI   360

THVPGGGNKK IETHKLTFRE NAKAKTDHGA EIVYKSPVVS GDTSPRHLSN VSSTGSIDMV   420

DSPQLATLAD EVSASLAKQG L                                            441
```

SEQ ID NO: 2 contains two N-terminal inserts and three microtubule-binding domains (2N3R) as follows:

```
MAEPRQEFEV MEDHAGTYGL GDRKDQGGYT MHQDQEGDTD AGLKESPLQT PTEDGSEEPG    60

SETSDAKSTP TAEDVTAPLV DEGAPGKQAA AQPHTEIPEG TTAEEAGIGD TPSLEDEAAG   120

HVTQARMVSK SLDGTGSDDK KAKGADGKTK IATPRGAAPP GQKGQANATR IPAKTPPAPK   180

TPPSSGEPPK SGDRSGYSSP GSPGTPGSRS RTPSLPTPPT REPKKVAVVR TPPKSPSSAK   240

SRLQTAPVPM PDLKNVKSKI GSTENLKHQP GGGKVQIVYK PVDLSKVTSK CGSLGNIHHK   300

PGGGQVEVKS EKLDFKDRVQ SKIGSLDNIT HVPGGGNKKI ETHKLTFREN AKAKTDHGAE   360

IVYKSPVVSG DTSPAHLSNV SSTGSIDMVD SPQLATLADE VSASLAKQGL             410
```

SEQ ID NO:3 contains one N-terminal insert and four microtubule-binding domains (1N4R) as follows:

```
MAEPRQEFEV MEDHAGTYGL GDRKDQGGYT MHQDQEGDTD AGLKESPLQT PTGDGSEEPG    60

SETSDAKSTP TAEAEEAGIG DTPSLEDEAA GHVTQARMVS KSLDGTGSDD KKAKGADGKT   120

LIATPRGAAP PGQKGQANAT RIPAKTPPAP KTPPSSGEPP KSGDRSGYSS PGSPGTPGSR   180

SRTPSLPTPP TREPKKVAVV RTPPKSPSSA KSRLQTAPVP MPDLKNVKSK IGSTENLKHQ   240

PGGGKVQIIN KKLDLSNVQS KCGSLDNILH VPGGGSVQIV YKPVDLSKVT SKCGSLGNIH   300

HKPGGGQVEV KSEKLDFKDR VQSKIGSLDN ITHVPGGGNK KIETHKLTFR ENAKAKTDHG   360

AEIVYKSPVV SGDTSPRHLS NVSSTGSIDM VDSPQLATLA DEVSASLAKQ GL           412
```

SEQ ID NO: 4 contains zero N-terminal inserts and four microtubule-binding domains (0N4R) as follows:

```
MAEPRQEFEV MEDHAGTYGL GDRLDQGGYT MHQDQEGDTD AGLKAEEAGI GDTPSLEDEA    60
AGHVTQARMV SKSKDGTGSD DKKAKGADGK TKIATPRGAA PPGQKGQANA TRIPAKTPPA   120
PKTPPSSGEP PKSGDRSGYS SPGSPGTPGS RSRTPSLPTP PTREPKKVAV VATPPKSPSS   180
AKSRLQTAPV PMPDLKNVKS LIGSTENLKH QPGGGKVQII NKKLDLSNVQ SKCGSKDNIK   240
HVPGGGSVQI VYKPVDLSKV TSKCGSLGNI HHKPGGGQVE VKSEKLDFKD RVQSKIGSLD   300
NITHVPGGGN KKIETHKLTF RENAKALTDH GAEIVYKSPV VSGDTSPRHL SNVSSTGSID   360
MVDSPQLATL ADEVSASLAK QGL                                          383
```

SEQ ID NO: 5 contains one N-terminal insert and three microtubule-binding domains (1N3R) as follows:

```
MAEPRQEFEV MEDHAGTYGL GDRKDQGGYT MHQDQEGDTD AGLKESPLQT PTEDGSEEPG    60
SETSDAKSTP TAEAEEAGIG DTPSLEDEAA GHVTQARMVS KSKDGTGSDD KKAKGADGKT   120
KIATPRGAAP PGQKGQANAT RIPAKTPPAP KTPPSSGEPP KSGDRSGYSS PGSPGTPGSR   180
SRTPSLPTPP TREPKKVAVV RTPPKSPSSA KSRLQTAPVP MPDLKNVKSK IGSTENLKHQ   240
PGGGKVQIVY KPVDLSKVTS KCGSLGNIHH KPGGGQVEVK SEKLDFKDRV QSKIGSLDNI   300
THVPGGGNKK IETHKLTFRE NAKAKTDHGA EIVYKSPVVS GDTSPRHLSN VSSTGSIDMV   360
DSPQLATLAD EVSASLAKQG L                                            381
```

SEQ ID NO: 6 contains zero N-terminal inserts and three microtubule-binding domains (0N3R) as follows:

```
MAEPRQEFEV MEDHAGTYGL GDRKDQGGYT MHQDQEGDTD AGLKAEEAGI GDTPSLEDEA    60
AGHVTQARMV SKSKDGTGSD DKKAKGADGK TKIATPRGAA PPGQKGQANA TRIPAKTPPA   120
PKTPPSSGEP PKSGDRSGYS SPGSPGTPGS RSRTPSLPTP PTREPKKVAV VRTPPKSPSS   180
AKSRLQTAPV PMPDLKNVKS KIGSTENLKH QPGGGKVQIV YKPVDLSKVT SKCGSLGNIH   240
HKPGGGQVEV KSEKLDFKDR VQSKIGSLDN ITHVPGGGNK KIGTHKLTFR ENAKAKTDHG   300
AEIVYKSPVV SGDTSPRHLS NVSSTGSIDM VDSPQLATLA DEVSASLAKQ GL           352
```

The truncated tau protein of the present invention can be phosphorylated at one or more amino acid residues. In one embodiment, the truncated tau protein is fully phosphorylated Amino acid residues in the full length tau protein, SEQ ID NO:1, that are or can be phosphorylated include tyrosines at amino acid positions 18, 29, 97, 310, and 394; serines at amino acid positions 184, 185, 198, 199, 202, 208, 214, 235, 237, 238, 262, 293, 324, 356, 396, 400, 404, 409, 412, 413, and 422; and threonines at amino acids positions 175, 181, 205, 212, 217, 231, and 403. Amino acid residues which are or can be phosphorylated in SEQ ID NO:2 include tyrosines at positions 18, 29, 197, 279, and 363; serines at positions 184, 185, 198, 199, 202, 208, 214, 235, 237, 238, 262, 293, 325, 365, 369, 373, 378, 381, 382, 391; and threonine at positions 175, 181, 205, 212, 217, 231, 372 Amino acid residues which are or can be phosphorylated in SEQ ID NO:3 include tyrosines at positions 18, 29, 168, 281, and 365; serines at positions 155, 156, 169, 170, 173, 179, 185, 206, 208, 209, 233, 264, 295, 327, 367, 371, 375, 380, 383, 384, 393; and threonines at positions 146, 152, 176, 183, 188, 202, and 374 Amino acid residues which are or can be phosphorylated in SEQ ID NO:4 include tyrosines at positions 18, 29, 139, 252, 336; serines at positions 126, 127, 140, 141, 144, 150, 156, 177, 179, 180, 204, 235, 266, 298, 338, 342, 346, 351, 354, 355, 364, and threonines at positions 117, 123, 147, 154, 159, 173, and 345 Amino acid residues which are or can be phosphorylated residues in SEQ ID NO: 5 include tyrosines at positions 18, 29, 168, 250, 334; serines at positions 155, 156, 169, 170, 173, 179, 185, 206, 208, 209, 233, 264, 296, 336, 340, 344, 349, 352, 353, 362; and threonines at positions 146, 152, 1376, 183, 188, 202, 343 Amino acid residues which are or can be phosphorylated in SEQ ID NO: 6 include tyrosines at positions 18, 29, 139, 221, and 305; serines at positions 126, 127, 140, 141, 144, 150, 156, 177, 179, 180, 204, 235, 267, 307, 311, 315, 320, 323, 324, 333; and threonine at positions 117, 123, 147, 154, 159, 173, and 314. Additional tyrosine, serine or threonine amino acids within the tau sequences may also be phosphorylated.

Thus, a further aspect of the invention relates to a phosphorylated truncated tau protein or a portion thereof and a pharmaceutical composition containing the phosphorylated truncated tau protein or a portion thereof. In certain embodiments, the truncated tau protein is tau1-421 (ΔTau), or a C-terminal fragment thereof (e.g., tau411-421, tau412-421, tau413-421, tau414-421, tau 415-421, tau416-421, tau417-421, tau418-421, or tau419-421), which is phosphorylated at one or more of the following $Tyr^{18}$, $Tyr^{29'}$, $Ser^{184}$, $Ser^{185}$, $Ser^{198}$, $Ser^{199}$, $Ser^{202}$, $Ser^{208}$, $Ser^{214}$, $Ser^{235}$, $Ser^{237}$, $Ser^{238}$, $Ser^{262}$, $Ser^{293}$, $Thr^{175}$, $Thr^{181}$, $Thr^{205}$, $Thr^{212}$, $Thr^{217}$, $Ser^{411}$, $Ser^{412}$, $Ser^{416}$, $Thr^{414}$. In some of these embodiments, the truncated tau protein is a C-terminal fragment of ΔTau which is phosphorylated at one or more of the following $Ser^{411}$, $Ser^{412}$, $Ser^{416}$, and Thr414. The phosphorylated truncated tau protein can be an isoform, fragment, or a recombinant form of the protein. Likewise the phosphorylated truncated tau protein can also contain one or more amino acid mutations. In addition to the phosphorylated truncated tau protein, the pharmaceutical composition may also contain a pharmaceutical carrier and/or a suitable adjuvant as described below. In certain embodiments, vaccination of a subject with a phosphorylated truncated tau protein, or a fragment thereof, leads to generation of antibodies that can cross the blood brain barrier and/or get produced in the brain, and subsequently selectively bind and react with abnormal tau and, e.g., reduce the extent of aggregated tau in the brain and slow the progression of Alzheimer's disease or other tauopathies. In certain embodiments, the truncated tau is phosphorylated at 1, 2, 3, 4, 5, or 6 of the following positions: $Tyr^{18}$, $Tyr^{29}$, $Ser^{184}$, $Ser^{185}$, $Ser^{198}$, $Ser^{199}$, $Ser^{202}$, $Ser^{208}$, $Ser^{214}$, $Ser^{235}$, $Ser^{237}$, $Ser^{238}$, $Ser^{262}$, $Ser^{293}$, $Thr^{175}$, $Thr^{181}$, $Thr^{205}$, $Thr^{212}$, $Thr^{217}$, $Thr^{231}$, $Ser^{411}$, $Ser^{416}$, and $Thr^{414}$.

In certain embodiments, the truncated tau is phosphorylated at one or more of the following amino acids: $Ser^{199}$, $Ser^{202}$, $Ser^{214}$, $Ser^{235}$, $Ser^{396}$, $Ser^{404}$, $Thr^{205}$, $Thr^{231}$, and $Thr^{212}$, $Ser^{411}$, $Ser^{412}$, $Ser^{416}$, and $Thr^{414}$.

Unless otherwise indicated, reference to tau includes the natural human amino acid sequences (SEQ ID NO: 1-6), and specifically refers to the longest isoform of tau (SEQ ID NO: 1), also known as htau40. Variants of such segments, analogs, and mimetics of the natural tau peptide that induce and/or crossreact with antibodies to the abnormal tau proteins can also be used. Analogs, including allelic, species, and induced variants, typically differ from naturally occurring peptides at one, two, or a few positions, often by virtue of conservative substitutions. Analogs typically exhibit at least 80 or 90% sequence identity with natural peptides. Some analogs also include unnatural amino acids or modifications of N or C terminal amino acids at one, two, or a few positions.

In addition to wildtype or natural tau proteins, the use of truncated tau proteins containing one or more amino acid substitutions is also contemplated. In one embodiment of the present invention, the truncated tau protein contains a proline to leucine mutation at amino acid position 301 (P301L) of SEQ ID NO: 1. Other amino acid mutations of the tan protein are also contemplated. These mutations include a lysine to threonine mutation at amino acid residue 257 (K257T) in SEQ ID NO: 1; an isoleucine to valine mutation at amino acid position 260 (1260V) of SEQ ID NO:1; a glycine to valine mutation at amino acid position 272 (G272V) of SEQ ID NO:1; an asparagine to lysine mutation at amino acid position 279 (N279K) of SEQ ID NO:1; an asparagine to histidine mutation at amino acid position 296 (N296H) of SEQ ID NO:1; a proline to serine mutation at amino acid position 301 (P301S) of SEQ ID NO:1; a glycine to valine mutation at amino acid position 303 (G303V) of SEQ ID NO:1; a serine to asparagine mutation at position 305 (5305N) of SEQ ID NO:1; a glycine to serine mutation at amino acid position 335 (G335S) of SEQ ID NO:1; a valine to methionine mutation at position 337 (V337M) of SEQ ID NO:1; a glutamic acid to valine mutation at position 342 (E342V) of SEQ ID NO:1; a lysine to isoleucine mutation at amino acid position 369 (K3691) of SEQ ID NO:1; a glycine to arginine mutation at amino acid position 389 (G389R) of SEQ ID NO:1; and an arginine to tryptophan mutation at amino acid position 406 (R406W) of SEQ ID NO:1. In one embodiment of the present invention, the truncated tau mutant protein or peptide fragment is phosphorylated.

Immunogenic fragments of the truncated tau protein useful for the present invention can be identified based on sequence antigenicity, hydrophilicity, and accessibility. In a preferred embodiment, the truncated tau protein or its immunogenic epitopes may or may not be phosphorylated at one or more amino acids. While peptides of longer lengths have in some instances been used to successfully generate end-specific antibodies, Saido and co-workers (1993; 1994) established that there is a length of five amino acids for any given peptide which ensures that the specific free amino group at the N-terminus constitutes an essential part of the epitope recognized by the new antibody. Thus, in a preferred embodiment, the immunogenic fragment of the truncated tau comprises a linear sequence of at least five amino acids of the tau protein which ensures that the specific free amino group at the N-terminus constitutes an essential part of the epitope recognized by the new linear epitope free-end specific antibody. In other embodiments, fragments of truncated tau have at least the last 20, 30 or 45 amino acids of the truncated tau, and linear epitope free-end specific or conformation-specific antibodies are generated. In additional embodiments, a fragment of a truncated tau comprises or consists of a linear sequence of four amino acids of the truncated tau.

In certain embodiments, the immunogenic fragment of the truncated tau comprises or consists of the following sequences, or fragments thereof, or a homologous sequence:

```
EPRQEFEVMED;           SEQ ID NO: 7

PRQEFEVMED;            SEQ ID NO: 8

QEFEVMED;              SEQ ID NO: 9

EFEVMED;               SEQ ID NO: 10

FEVMED;                SEQ ID NO: 11

EVMED;                 SEQ ID NO: 12

VMED;                  SEQ ID NO: 13

MED;                   SEQ ID NO: 14

HAGTYGLGDRKD;          SEQ ID NO: 15

HAGTYGLGDRK;           SEQ ID NO: 16

HAGTYGLGDR;            SEQ ID NO: 17

HAGTYGLGD;             SEQ ID NO: 18

HAGTYGLG;              SEQ ID NO: 19

HAGTYGL;               SEQ ID NO: 20

HAGTYG;                SEQ ID NO: 21

HAGTY;                 SEQ ID NO: 22
```

-continued

HAGT; SEQ ID NO: 23

IVYKSPVVSGD; SEQ ID NO: 24

IVYKSPVVSG; SEQ ID NO: 25

IVYKSPVVS; SEQ ID NO: 26

IVYKSPVV; SEQ ID NO: 27

IVYKSPV; SEQ ID NO: 28

IVYKSP; SEQ ID NO: 29

IVYKS; SEQ ID NO: 30

IVYK; SEQ ID NO: 31

IVY; SEQ ID NO: 32

PQLATLADEVS SEQ ID NO: 33

PQLATLADEV; SEQ ID NO: 34

PQLATLADE; SEQ ID NO: 35

PQLATLAD; SEQ ID NO: 36

PQLATLA; SEQ ID NO: 37

PQLATL; SEQ ID NO: 38

PQLAT; SEQ ID NO: 39

PQLA; SEQ ID NO: 40

PQL; SEQ ID NO: 41

SPQLATLADE; SEQ ID NO: 42

SPQLATLAD; SEQ ID NO: 43

SPQLATLA; SEQ ID NO: 44

SPQLATL; SEQ ID NO: 45

SPQLAT; SEQ ID NO: 46

SPQLA; SEQ ID NO: 47

SPQL; SEQ ID NO: 48

SPQ; SEQ ID NO: 49

-continued

DSPQLATL; SEQ ID NO: 50

NAKAKTDHGAE; SEQ ID NO: 51

AKAKTDHGAE; SEQ ID NO: 52

KAKTDHGAE; SEQ ID NO: 53

AKTDHGAE; SEQ ID NO: 54

KTDHGAE; SEQ ID NO: 55

TDHGAE; SEQ ID NO: 56

DHGAE; SEQ ID NO: 57

HGAE; SEQ ID NO: 58

GAE; SEQ ID NO: 59

SSTGSIDMVDS; SEQ ID NO: 60

STGSIDMVDS; SEQ ID NO: 61

TGSIDMVDS; SEQ ID NO: 62

GSIDMVDS; SEQ ID NO: 63

SIDMVDS; SEQ ID NO: 64

IDMVDS; SEQ ID NO: 65

DMVDS; SEQ ID NO: 66

MVDS; SEQ ID NO: 67

VDS; SEQ ID NO: 68

NVSSTGSIDMV; SEQ ID NO: 69

VSSTGSIDMV; SEQ ID NO: 70

SSTGSIDMV; SEQ ID NO: 71

STGSIDMV; SEQ ID NO: 72

TGSIDMV; SEQ ID NO: 73

GSIDMV; SEQ ID NO: 74

SIDMV; SEQ ID NO: 75

IDMV; SEQ ID NO: 76

-continued

| | |
|---|---|
| DMV; | SEQ ID NO: 77 |
| NVSTGSIDMVD; | SEQ ID NO: 78 |
| VSTGSIDMVD; | SEQ ID NO: 79 |
| STGSIDMVD; | SEQ ID NO: 80 |
| TGSIDMVD; | SEQ ID NO: 81 |
| GSIDMVD; | SEQ ID NO: 82 |
| SIDMVD; | SEQ ID NO: 83 |
| IDMVD; | SEQ ID NO: 84 |
| DMVD; | SEQ ID NO: 85 |
| SSTGSIDMVD; | SEQ ID NO: 86 |
| SPQLATLADE; | SEQ ID NO: 87 |
| SPQLATLAD; | SEQ ID NO: 88 |
| SPQLATLA; | SEQ ID NO: 89 |
| SPQLATL; | SEQ ID NO: 90 |
| SPQLAT; | SEQ ID NO: 91 |
| SPQLA; | SEQ ID NO: 92 |
| SPQL; | SEQ ID NO: 93 |
| SPQ; and | SEQ ID NO: 94 |
| | SEQ ID NO: 116. |

In some of these embodiments, the immunogenic fragment of the truncated tau comprises or consists of a sequence of SEQ ID NOS: 78-86 or 116, and, preferably, SEQ ID NO: 83-86 or 116.

The free end (N-terminus or C-terminus) of the truncated peptide is part of the immunogenic fragment and is necessary for the generation of the neoepitope-specific antibodies of the present invention (i.e., the free N-terminus or C-terminus is an essential part of the antibody's epitope). In certain embodiments, at least one of the serines and threonines in these sequences is phosphorylated, and the phosphorylated serine(s) and/or threonine(s) is also an essential part of the antibody's epitope.

In certain embodiments, truncated tau comprises or consists of phosphorylated or non-phosphorylated tau391-421, tau395-421 (e.g., phosphorylated or non-phosphorylated at one or more of the following Ser396, Ser400, Ser404, Ser409, Ser412, Ser413, Tyr394, Thr205, and/or Thr212), tau408-421 (e.g., phosphorylated non-phosphorylated at one or more of the following Ser409, Ser412, and/or Ser413), tau414-421 (e.g., phosphorylated or non-phosphorylated at one or more of the following Ser396, Ser400, Ser404, Ser409, Ser412, Ser413, Tyr394, Thr205, and/or Thr212), tau415-421, tau416-421, tau417-421, tau418-421, or tau419-421, tau361-391, tau386-391, tau385-391, tau384-391.

In an embodiment of the present invention, the truncated tau peptides of the present invention can contain one or more D-amino acid residues. The amino acids being in U-form would have the effect of enhancing the stability of the peptide. These D-amino acids can be in the same order as the L-form of the peptide or assembled in a reverse order from the L-form sequence to maintain the overall topology of the native sequence (Ben-Yedidia et al., "A Retro-Inverso Peptide Analogue of Influenza Virus Hemagglutinin B-cell Epitope 91-108 Induces a Strong Mucosal and Systemic Immune Response and Confers Protection in Mice after Intranasal Immunization," Mol Immunol 39:323 (2002); Guichard, et al., "Antigenic Mimicry of Natural L-peptides with Retro-Inverso-Peptidomimetics," PNAS 91:9765-9769 (1994); Benkirane, et al., "Antigenicity and Immunogenicity of Modified Synthetic Peptides Containing D-Amino Acid Residues," J. Bio. Chem. 268(35):26279-26285 (1993), which are hereby incorporated by reference in their entirety).

Therapeutic agents can be longer polypeptides that include, for example, an active fragment (e.g., immunogenic portion) of tau peptide (e.g, ΔTau), together with other amino acids. For example, in certain embodiments the therapeutic agents include fusion proteins comprising a segment of tau linked, with or without a spacer, to a promiscuous T-helper cell epitope which promotes a B-cell response against the segment of tau.

Another aspect of the present invention relates to a pharmaceutical composition containing (one or more of) the immunogenic epitopes of the truncated tau protein. In certain embodiments, immunogenic epitope of truncated tau comprises tau391-421 (e.g., phosphorylated or non-phosphorylated at one or more of the following Ser396, Ser400, Ser404, Ser409, Ser412, Ser413, Tyr394, Thr205, and/or Thr212), tau395-421 (e.g., phosphorylated or non-phosphorylated at one or more of the following Ser396, Ser400, Ser404, Ser409, Ser412, Ser413, Tyr394, Thr205, and/or Thr212), tau408-421 (e.g., phosphorylated non-phosphorylated at one or more of the following Ser409, Ser412, and/or Ser413), tau361-391 (e.g., phosphorylated non-phosphorylated at Ser396), tau411-421, tau416-421, tau 417-421, tau 418-421, tau 419-421, or a fragment of any of the foregoing. In certain embodiments, the immunogenic epitope sequence comprises or consists of any one of SEQ ID NO: 7-94, or 116, or a fragment thereof.

Other portions or fragments of the tau protein which are suitable for practicing the present invention may include recombinant forms of abnormal tau protein (e.g., truncated tau) created by cleavage and/or phosphorylation of normal tau protein.

Abnormally truncated forms of human tau proteins—tauons—can be prepared by using any of numerous well known synthetic recombinant techniques. Briefly, most of the techniques which are used to transform cells, construct vectors, extract messenger RNA, prepare cDNA libraries, and the like are widely practiced in the art, and most practitioners are familiar with the standard resource materials which describe specific conditions and procedures widely practiced in the art. Abnormal tau proteins such as truncated tau can be synthesized by solid phase peptide synthesis or recombinant expression, or can be obtained from natural sources. Automatic peptide synthesizers are commercially available from numerous suppliers, such as Applied Biosystems (Foster City, Calif.). Recombinant expression systems can include bacteria, such as E. coli, yeast, insect cells, or mammalian cells. Procedures for recombinant expression are described by Sambrook et al., Molecular Cloning: A Laboratory Manual (C.S.H.P. Press, NY 2d ed., 1989), which is hereby incorporated by reference in its entirety.

The most commonly used prokaryote system for the production of recombinant proteins remains E. coli, however, other microbial strains may also be used, such as Bacilli, for example Bacillus subtilis, various species of Pseudomonas, or other bacterial strains. In such prokaryotic systems, plasmid vectors which contain replication sites and control sequences derived from a species compatible with the host are used. Commonly used prokaryotic control sequences include promoters for transcription initiation, optionally with an operator, along with ribosome binding site sequences.

A wide variety of eukaryotic hosts are also now available for production of recombinant foreign proteins. As in bacteria, eukaryotic hosts may be transformed with expression systems which produce the desired protein directly, but more commonly, signal sequences are provided to effect the secretion of the protein. Eukaryotic systems have the additional advantage that they are able to process introns which may occur in the genomic sequences encoding proteins of higher organisms. Eucaryotic systems also provide a variety of processing mechanisms which result in, for example, glycosylation, oxidation or derivatization of certain amino acid residues, conformational control, and so forth.

Commonly used eukaryotic systems include yeast, insect cells, mammalian cells, avian cells, and cells of higher plants. The list is not exhaustive. Suitable promoters are available which are compatible and operable for use in each of these host types as well are termination sequences and enhancers, as e.g., the baculovirus polyhedron promoter. As above, promoters can be either constitutive or inducible. For example, in mammalian system, the MTII promoter can be induced by the addition of heavy metal ions.

The particulars for the construction of expression systems suitable for desired host are known to those in the art. For recombinant production of the protein, the DNA encoding it is suitable ligated into the expression system of choice, and the system is then transformed into the compatible host cell which is then cultured and maintained under conditions wherein expression of the foreign gene takes place. The tauons of this invention produced this way, are recovered from the culture, either by lysing the cells or from the culture medium as appropriate and known to those in the art.

Correct ligations for plasmid construction can be confirmed by first transforming a suitable host with the ligation mixture. Successful transformants are selected by ampicillin, tetracycline or other antibiotic resistance or using other markers depending on the mode of plasmid construction, as is understood in the art.

In a variation of the present invention, an immunogenic peptide, such as a truncated tau, can be expressed/presented by a virus or bacteria as part of an immunogenic composition. A nucleic acid encoding the immunogenic peptide is incorporated into a genome or episome of the virus or bacteria.

Optionally, the nucleic acid is incorporated in such a manner that the immunogenic peptide is expressed as a secreted protein or as a fusion protein with an outer surface protein of a virus or a transmembrane protein of bacteria so that the peptide is displayed. Viruses or bacteria used in such methods should be nonpathogenic or attenuated. Suitable viruses include adenovirus, HSV, Venezuelan equine encephalitis virus and other alpha viruses, vesicular stomatitis virus, and other rhabdo viruses, vaccinia and fowl pox. Suitable bacteria include Salmonella and Shigella. Fusion of an immunogenic peptide to HBsAg of HBV is particularly suitable.

Immune responses against neurofibrillary tangles can also be induced by administration of nucleic acids encoding segments of an abnormal tau peptide or a truncated tau, and fragments thereof, other peptide immunogens, or antibodies and their component chains used for passive immunization. Such nucleic acids can be DNA or RNA. A nucleic acid segment encoding an immunogen is typically linked to regulatory elements, such as a promoter and enhancer, which allow expression of the DNA segment in the intended target cells of a patient. For expression in blood cells, as is desirable for induction of an immune response, promoter and enhancer elements from light or heavy chain immunoglobulin genes or the CMV major intermediate early promoter and enhancer are suitable to direct expression. The linked regulatory elements and coding sequences are often cloned into a vector. For administration of double-chain antibodies, the two chains can be cloned in the same or separate vectors.

A number of viral vector systems are available including retroviral systems (see, e.g., Lawrie et al., Cur. Opin. Genet. Develop. 3:102-109 (1993), which is hereby incorporated by reference in its entirety); adenoviral vectors (Bett et al., J. Virol. 67:5911 (1993), which is hereby incorporated by reference in its entirety); adeno-associated virus vectors (Zhou et al., J. Exp. Med. 179:1867 (1994), which is hereby incorporated by reference in its entirety), viral vectors from the pox family including vaccinia virus and the avian pox viruses, viral vectors from the alpha virus genus, such as those derived from Sindbis and Semliki Forest Viruses (Dubensky et al., J. Virol 70:508-519 (1996), which is hereby incorporated by reference in its entirety), Venezuelan equine encephalitis virus (see U.S. Pat. No. 5,643,576 to Johnston et al., which is hereby incorporated by reference in its entirety) and rhabdoviruses, such as vesicular stomatitis virus (see WO 96/34625 to Rose, which is hereby incorporated by reference in its entirety) and papillomaviruses (Ohe, et al., Human Gene Therapy 6:325-333 (1995); WO 94/12629 to Woo et al.; and Xiao & Brandsma, Nucleic Acids. Res. 24:2630-2622 (1996), which are hereby incorporated by reference in their entirety.

DNA encoding an immunogen, or a vector containing the same, can be packaged into liposomes. Suitable lipids and related analogs are described by U.S. Pat. No. 5,208,036 to Eppstein et al., U.S. Pat. No. 5,264,618 to Feigner et al., U.S. Pat. No. 5,279,833 to Rose, and U.S. Pat. No. 5,283,185 to Epand et al., which are hereby incorporated by reference in their entirety. Vectors and DNA encoding an immunogen can also be adsorbed to or associated with particulate carriers, examples of which include polymethyl methacrylate polymers and polylactides and poly(lactide-co-glycolides).

Gene therapy vectors or naked DNA can be delivered in vivo by administration to an individual patient, typically by systemic administration (e.g., intravenous, intraperitoneal, nasal, gastric, intradermal, intramuscular, subdermal, or intracranial infusion) or topical application (see e.g., U.S. Pat. No. 5,399,346 to Anderson et al., which is hereby incorporated by reference in its entirety). Such vectors can further include facilitating agents (U.S. Pat. No. 5,593,970 to Attardo et al., which is hereby incorporated by reference in its entirety). DNA can also be administered using a gene gun (Xiao & Brandsma, Nucleic Acids. Res. 24:2630-2622 (1996), which is hereby incorporated by reference in its entirety). The DNA encoding an immunogen is precipitated onto the surface of microscopic metal beads. The microprojectiles are accelerated with a shock wave or expanding helium gas, and penetrate tissues to a depth of several cell layers. For example, the Accel™ Gene Delivery Device manufactured by Agacetus, Inc. Middleton Wis. is suitable. Alternatively, naked DNA can pass through skin into the blood stream simply by spotting the DNA onto skin with chemical or mechanical irritation (see WO 95/05853 to Carson et al., which is hereby incorporated by reference in its entirety).

In a further variation, vectors encoding immunogens can be delivered to cells ex vivo, such as cells explanted from an individual patient (e.g., lymphocytes, bone marrow aspirates, tissue biopsy) or universal donor hematopoietic stem cells, followed by reimplantation of the cells into a patient, usually after selection for cells which have incorporated the vector.

A further aspect of the invention relates to a phosphorylated truncated tau protein and a pharmaceutical composition containing the phosphorylated truncated tau protein. The phosphorylated truncated tau protein can be an isoform, fragment, or a recombinant form of the protein. Likewise the phosphorylated truncated tau protein can also contain one or more amino acid mutations. In addition to the phosphorylated truncated tau protein, the pharmaceutical composition also contains a pharmaceutical carrier and/or a suitable adjuvant as described below.

Tau-peptides can also be produced by chemical synthesis of the amino acid sequence of a tau-protein (Goedert et al., 1988, Proc. Natl. Acad. Sci. USA, 85:4051-4055), as predicted from the cloning and sequencing of a cDNA coding for a tau-protein. This tau-protein sequence information may be utilized to predict the appropriate amino and carboxy terminal tau-peptides to be chemically synthesized using standard peptide synthesis methods known in the art. These methods include a solid-phase method devised by R. Bruce Merrifield, (Erickson and Merrifield, "Solid-Phase Peptide Synthesis", in The Proteins, Volume 2, H. Neurath & R. Hill (eds.) Academic Press, Inc., New York pp. 255-257; Merrifield, 1986, "Solid phase synthesis", Science, 242:341-347). In the solid-phase method, amino acids are added stepwise to a growing peptide chain that is linked to an insoluble matrix, such as polystyrene beads. A major advantage of this method is that the desired product at each stage is bound to beads that can be rapidly filtered and washed and thus the need to purify intermediates is obviated. All of the reactions are carried out in a single vessel, which eliminates losses due to repeated transfers of products. This solid phase method of chemical peptide synthesis can readily be automated making it feasible to routinely synthesize peptides containing about 50 residues in good yield and purity (Stewart and Young, 1984, Solid Phase Peptide Synthesis, 2nd ed., Pierce Chemical Co.; Tam et al., 1983, J. Am. Chem. Soc., 105:6442). For example, tau-peptides corresponding to amino acid residues 1 to 30 and 331 to 352 could be synthesized.

The production of tau-peptides can further be achieved by recombinant DNA technology. For example, appropriate tau nucleotide coding sequences may be synthesized, cloned and expressed in appropriate host cells. Since the DNA sequence encoding for a tau-protein is known (Goeddert et al., 1988, Proc. Natl. Acad. Sci., USA 85:4051-4055), DNA probes may be synthesized by standard methods known in the art to screen cDNA libraries prepared from brain tissue of Alzheimer's disease patients for the specific tau-protein cDNA's. These DNA probes can further be used to isolate the entire family of tau-protein genes from these cDNA libraries using methods which are well known to those skilled in the art. See, for example, the techniques described in Maniatis et al., 1982, Molecular Cloning A Laboratory Manual, Cold Spring Harbor Laboratory, N.Y., Chapter 7.

The polymerase chain reaction (PCR) technique can be utilized to amplify the individual members of the tau family for subsequent cloning and expression of tau-protein cDNAs (e.g., see U.S. Pat. Nos. 4,683,202; 4,683,195; 4,889,818; Gyllensten et al., 1988, Proc. Nat'l Acad. Sci. USA, 85:7652-7656; Ochman et al., 1988, Genetics, 120:621-623; Triglia et al., 1988, Nucl. Acids. Res., 16:8156; Frohman et al., 1988, Proc. Nat'l Acad. Sci. USA, 85:8998-9002; Loh et al., 1989, Science, 243:217-220).

Methods which are well known to those skilled in the art can be used to construct expression vectors containing tau-proteins or fragments thereof coding sequences and appropriate transcriptional/translational control signals. These methods include in vitro recombinant DNA techniques, synthetic techniques and in vivo recombination/genetic recombination. See, for example, the techniques described in Maniatis et al., 1982, Molecular Cloning A Laboratory Manual, Cold Spring Harbor Laboratory, N.Y., Chapter 12.

A variety of host-expression vector systems may be utilized to express tau-proteins or fragments thereof. These include but are not limited to microorganisms such as bacteria transformed with recombinant bacteriophage DNA, plasmid DNA or cosmid DNA expression vectors containing a coding sequence for a tau-protein or fragment thereof; yeast transformed with recombinant yeast expression vectors containing a coding sequence for a tau-protein or fragment thereof; insect cell systems infected with recombinant virus expression vectors (e.g., baculovirus) containing a coding sequence for a tau-protein or fragment thereof; or animal cell systems infected with recombinant virus expression vectors (e.g., adenovirus, vaccinia virus) containing a coding sequence for a tau-protein or fragment thereof.

The expression elements of these vectors vary in their strength and specificities. Depending on the host/vector system utilized, any of a number of suitable transcription and translation elements, including constitutive and inducible promoters, may be used in the expression vector. For example, when cloning in bacterial systems, inducible promoters such as pL of bacteriophage lambda, plac, ptrp, ptac (ptrp-lac hybrid promoter) and the like may be used; when cloning in insect cell systems, promoters such as the baculovirus polyhedrin promoter may be used; when cloning in mammalian cell systems, promoters such as the adenovirus late promoter or the vaccinia virus 7.5K promoter may be used. Promoters produced by recombinant DNA or synthetic techniques may also be used to provide for transcription of the inserted coding sequence for a tau-protein or fragment thereof.

In yeast, a number of vectors containing constitutive or inducible promoters may be used. For a review see, Current Protocols in Molecular Biology, Vol. 2, 1988, Ed. Ausubel et al., Greene Publish. Assoc. & Wiley Interscience Ch. 13; Grant et al., 1987, Expression and Secretion Vectors for Yeast, in Methods in Enzymology, Eds. Wu & Grossman, 1987, Acad. Press, N.Y., Vol. 153, pp. 516-544; Glover, 1986, DNA Cloning, Vol. II, IRL Press, Wash., D.C. Ch. 3; and Bitter, 1987, Heterologous Gene Expression in Yeast, Methods in Enzymology, Eds. Berger & Kimmel, Acad. Press, N.Y., Vol. 152, pp. 673-684; and The Molecular Biology of the Yeast *Saccharomyces,* 1982, Eds. Strathern et al., Cold Spring Harbor Press, Vols. I and II. For complementation assays in yeast, cDNAs for tau-proteins or fragments thereof may be cloned into yeast episomal plasmids (YEp) which replicate autonomously in yeast due to the presence of the yeast 2μ circle. The tau-protein or fragment thereof sequence may be cloned behind either a constitutive yeast promoter such as ADH or LEU2 or an inducible promoter such as GAL (Cloning in Yeast, Chpt. 3, R. Rothstein In; DNA Cloning Vol. 11, A Practical Approach, Ed. DM Glover, 1986, IRL Press, Wash., D.C.). Constructs may contain the 5' and 3' non-translated regions of a cognate tau-protein mRNA or those corresponding to a yeast gene. YEp plasmids transform at high efficiency and the plasmids are extremely stable. Alternatively, vectors may be used which promote integration of foreign DNA sequences into the yeast chromosome.

In certain embodiments, an insect system could be used to express tau-proteins or fragments thereof. In one such system, *Autographa californica* nuclear polyhedrosis virus (AcNPV) is used as a vector to express foreign genes. The virus grows in *Spodoptera frugiperda* cells. The tau-protein or fragment thereof coding sequence may be cloned into non-essential regions (for example the polyhedrin gene) of the virus and placed under control of an AcNPV promoter (for example the polyhedrin promoter). Successful insertion of the polyhedrin gene results in production of non-occluded recombinant virus (i.e., virus lacking the proteinaceous coat coded for by the polyhedrin gene). These recombinant viruses are then used to infect *Spodoptera frugiperda* cells in which the inserted gene is expressed. (e.g., see Smith et al., 1983, J. Biol., 46:586; Smith, U.S. Pat. No. 4,215,051).

In cases where an adenovirus is used as an expression vector, the tau-protein or fragment thereof coding sequence may be ligated to an adenovirus transcription/translation control complex, e.g., the late promoter and tripartite leader sequence. This chimeric gene may then be inserted in the adenovirus genome by in vivo or in vitro recombination. Insertion in a non-essential region of the viral genome (e.g., region E1 or E3) will result in a recombinant virus that is viable and capable of expressing the tau-protein of fragment thereof in infected hosts. (e.g., See Logan & Shenk, 1984, Proc. Natl. Acad. Sci., (USA) 81:3655-3659). Alternatively, the vaccinia 7.5K promoter may be used. (e.g., see Mackett et al., 1982, Proc. Natl. Acad. Sci., (USA) 79:7415-7419; Mackett et al., 1984, J. Virol., 49:857-864; Panicali et al., 1982, Proc. Natl. Acad. Sci., 79: 4927-4931).

Specific initiation signals may also be required for efficient translation of the inserted tau-protein or fragment thereof coding sequences. These signals include the ATG initiation codon and adjacent sequences. In cases where the entire tau-protein genome, including its own initiation codon and adjacent sequences, are inserted into the appropriate expression vectors, no additional translational control signals may be needed. However, in cases where only a portion of the tau-protein coding sequence is inserted, exogenous translational control signals, including the ATG initiation codon, must be provided. Furthermore, the initiation codon must be in phase with the reading frame of the tau-protein or fragment thereof coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see Bitter et al., 1987, Methods in Enzymol., 153:516-544).

In addition, a host cell strain may be chosen which modulates the expression of the inserted sequences, or modifies and processes the gene product in the specific fashion desired. Expression driven by certain promoters can be elevated in the presence of certain inducers, (e.g., zinc and cadmium ions for metallothionein promoters). Therefore, expression of the genetically engineered tau-protein or fragment thereof may be controlled. This is important if the protein product of the cloned foreign gene is lethal to host cells. Furthermore, modifications (e.g., glycosylation) and processing (e.g., cleavage) of protein products may be important for the function of the protein. Different host cells have characteristic and specific mechanisms for the post-translational processing and modification of proteins. Appropriate cell lines or host systems can be chosen to ensure the correct modification and processing of the foreign protein expressed.

The host cells which contain the tau-protein or fragment thereof coding sequence and which express the biologically active tau-protein or fragment thereof gene product may be identified by at least four general approaches: (a) DNA-DNA hybridization; (b) the presence or absence of "marker" gene functions; (c) assessing the level of transcription as measured by expression of tau-protein mRNA transcripts in host cells; and (d) detection of tau-protein gene products as measured by immunoassays or by its biological activity. See U.S. Pat. No. 5,492,812, hereby incorporated by reference.

Once a recombinant that expresses a tau-protein or fragment thereof is identified, the gene product should be analyzed. This can be achieved by assays based on the physical, immunological or functional properties of the product.

A tau-protein or fragment thereof should be immunoreactive whether it results from the expression of the entire gene sequence, a portion of the gene sequence or from two or more gene sequences which are ligated to direct the production of chimeric proteins. This reactivity may be demonstrated by standard immunological techniques, such as radioimmunoprecipitation, radioimmune competition, or immunoblots.

1. Antibodies to Truncated Tau

Antibodies that specifically bind to and/or recognize any of the six isoforms of truncated tau protein or hyperphosphorylated version thereof and do not recognize, bind or show reactivity to untruncated tau may be therapeutically effective in the context of the present invention, e.g., to treat and/or prevent AD and/or another tauopathy.

The antibodies of the invention preferably specifically recognize the neoepitope created by cleavage of tau (i.e., the amino acid sequences of the free N-terminus or the free C-terminus of the peptide created by cleavage of tau), but do not recognize the same sequence of amino acids present internally in the normal tau protein. The antibodies of the invention, preferably, do not inhibit caspase cleavage of tau at Asp421. In certain embodiments, the antibodies specifically recognize a sequence out of SEQ ID No. 7-94 or 116, or any fragment thereof, in the truncated tau, and do not recognize the same sequence of amino acid when present in the normal tau protein. In certain embodiments, the antibodies specifically recognize a sequence out of SEQ ID Nos: 78-86 or 116, and do not recognize the same sequence of amino acid when present in the normal tau protein. The antibodies of the invention, in the preferred embodiments, are capable of crossing the blood-brain barrier (BBB) and are capable of clearing the peptides or truncated tau created by cleavage of tau and minimizing or preventing the neurofiblary tangles formation. At the same time, these antibodies are not expected to affect biological functions of the normal tau protein, because these sequences in the normal tau protein are internal and do not contain a free N- or C-terminus which is necessary for the antibodies' recognition of their epitope. These antibodies may therefore be used in the treatment and/or prevention of Alzheimer's disease and other tauopathies and in the preparation of pharmaceutical compositions (e.g., vaccines) for the treatment and prevention of these disorders.

In certain embodiments, the antibodies of the invention specifically recognize the neoepitope created by cleavage of tau (i.e., the amino acid sequences of the free N-terminus or the free C-terminus of the peptide created by cleavage of tau), but do not specifically recognize the same sequence of amino acids present in the normal tau protein or do not bind sufficiently to clear normal tau or affect its function. In some of these embodiments, the antibodies specifically recognize the neoepitope created by cleavage of tau at Asp421 (i.e., the free C-terminus of ΔTau), but do not specifically recognize the same sequence of amino acids present in the normal tau protein or do not bind sufficiently to clear normal tau or affect its function.

In certain embodiments, the antibodies recognize, bind or show reactivity with ΔTau, and do not recognize, bind or show reactivity with the longest isoform of tau (i.e., htau40).

In certain embodiments, where the aim is to directly block polymerization of ΔTau, the antibody has a low off rate.

In certain embodiments, the antibody recognizes both a cleavage site (e.g., Asp421) and phosphorylated amino acid within ten, six, five or four amino acids from the cleavage site.

In the preferred embodiments of the invention, the antibodies of the invention (i) inhibit, reduce, clear and/or eliminate tau truncated at its C-terminus, e.g., at the glutamic acid residue Glu391 or at the aspartic acid residue Asp421, or its N-terminus (e.g., at the aspartic acid residue Asp13), (ii) inhibit, reduce, clear and/or eliminate abnormal phosphorylated truncated tau (e.g., tau phosphorylated at Ser396 and/or Ser404), and/or (iii) prevent the neurofiblary tangles formation and/or increase clearance of the neurofiblary tangles, all without affecting the biological functions of the normal tau protein.

In certain embodiments, the antibody used in the methods of the invention is conformational antibody MN423, TauC3, Tau12, 5A6, DC11, anti-cleaved-Tau (ASP421), clone C3 or structurally similar antibodies. In some of these embodiments, the antibody is TauC3, or a structurally and/or functionally similar antibody.

It has been postulated that truncation of tau at Glu391 leads to Alzheimer's disease-specific conformational changes that are recognized by the conformational antibody MN423 [Kovacech, et al. 2010; Novak, et al. 1989; Novak, et al. 1993; Csokava, et al. 2006; Skrabana, et al. 2006; Skrabana, et al. 2007]. Another anti-tau antibody, DC11, recognizes abnormal tau proteins present in AD brains.

Further, it has been reported that antibody TauC3 specifically recognizes tau truncated at Asp421, whereas wild type tau containing three microtubule-binding repeats (produced by alternative splicing, designated 3R), or tau proteins truncated at amino acid residues Glu391 or Ala429 were not recognized by TauC3. (Gamblin, et al., supra).

Also, anti-cleaved-tau (ASP421), clone C3 is commercially available from Millipore, and may be used in the methods of the present invention. Anti-cleaved-tau (ASP421) is selective for a synthetic peptide corresponding to amino acids 412-421 (CSSTGSIDMVD) of human tau with a Cys at the N-terminal end.

It is believed that up until the present invention however, there was no teaching or suggestion in the literature of using TauC3, DC11, MN423, and anti-cleaved-Tau (ASP421), clone C3 or related antibodies to treat or prevent AD or another tauopathy.

It is further believed that TauC3, DC11, MN423, and anti-cleaved-Tau (ASP421), clone C3 or an antibody having a three-dimensional shape/structure as TauC3, MN423, and anti-cleaved-Tau (ASP421) may be used in the methods of the present invention to treat and/or prevent AD or another tauopathy.

The phospho-independent antibody 5A6 is the first of three N-terminal antibodies to label early diffuse tangles. (Horowitz, 2004). Horowitz, et al. report that the Tau-12 epitope becomes unmasked as lesions assume a fibrillar morphology, and subsequently the extreme N-terminal epitopes of tau are lost from tangles of human AD brains, a process that correlates temporally with the appearance of the C-terminal caspase truncation-specific epitope at D421. Further, Horowitz, et al. report that caspase-6 cleaves tau in vitro at aspartic acid residue Asp421, causing loss of immunoreactivity with both Tau-12 and 5A6 antibodies.

It is believed that the blood-brain barrier ("BBB") is compromised in various neurodegenerative diseases such as AD, and immunologists are aware of the fact that anti-secreting cells can enter the brain and secret antibodies locally. In healthy subjects, the BBB would be relatively impermeable to tau antibodies. As tau pathology begins, associated inflammatory changes and cellular stress may facilitate uptake of antibodies selective for truncated tau, and showing no binding and/or reactivity with normal tau, into the brain and subsequently into neurons, thereby allowing for the removal of pathological tau before and/or as it forms, which would in turn delay onset, treat or prevent the disease. The antibodies of the preferred embodiments of the invention are capable of crossing BBB in a mammal suffering from or at risk of developing a neurodegenerative disease (e.g., AD).

Truncated tau antibodies according to the invention may target pathological truncated tau extracellularly, intracellularly, or both. In extracellular targeting, the antibodies binding to their targets may directly promote their disassembly and may signal microglia to clear the antibody-protein complexes, thereby preventing or reducing potential direct or indirect toxic effect of extracellular tau aggregates. Intracellular tau may be cleared via antibody uptake, or by the antibody-mediated clearance of extracellular tau promoting secretion of intracellular tau through a shift in equilibrium.

In certain embodiments, the antibody is specific and selectively recognizes and reacts with Tau391-421, or a fragment thereof, (e.g., phosphorylated or non-phosphorylated at one or more of the following Ser396, Ser400, Ser404, Ser409, Ser412, Ser413, Tyr394, Thr205, and/or Thr212), Tau395-421 (e.g., phosphorylated or non-phosphorylated at one or more of the following Ser396, Ser400, Ser404, Ser409, Ser412, Ser413, Tyr394, Thr205, and/or Thr212), Tau408-421, or a fragment thereof, (e.g., phosphorylated non-phosphorylated at one or more of the following Ser409, Ser412, and/or Ser413), or Tau361-391, or a fragment thereof, (e.g., phosphorylated non-phosphorylated at Ser396), and do not recognize and show no reactivity to normal tau (e.g., untruncated tau) or the before mentioned peptides coupled/conjugated to a carrier protein. In additional embodiments, the antibody is specific to early N-terminal cleavage sites of tau, for example, the Asp13 truncation site.

In the preferred embodiments, the antibody recognizes a sequence out of SEQ ID No. 7-94 or 116, or any fragment thereof, in the truncated tau, and do not recognize the same sequence of amino acid when present internally in the normal tau protein. In some of these embodiments, the antibodies recognize a sequence out of SEQ ID Nos. 78-86 or 116, and do not recognize the same sequence of amino acid when present in the normal tau protein (e.g., the longest isoform of tau protein (htau40)).

Thus, a preferred embodiment of the invention is directed to immunotherapy (passive and/or active) against the free end epitopes of truncated tau or the neoepitopes created by cleavage of tau (e.g., at Asp421). It is believed that immunotherapy against the free end epitopes of truncated tau clears soluble truncated tau from the brain and minimizes or prevents formation of the neurofibrillary tangles, paired helical filaments and/or pathological aggregation of tau. In certain embodiments, immunotherapy against the free end epitopes of truncated tau blocks polymerization of tau directly. The immunotherapy may prevent or delay memory loss and mental deterioration associated with tauopathies (e.g., AD), and in the preferred embodiments may improve cognitive or mental function in patient suffering from or at risk of developing a tauopathy (e.g., AD). This is not taught or suggested by the literature to date. The literature also does not report where the soluble truncated forms exist in the cell and if such forms and locations are accessible to antibodies. This approach may be useful to clear soluble neurotoxic tau before it forms pathological tangles, microfibriles and/or aggregates, and does not depend on producing conformational antibodies to preformed tau tangles that are already causing damage. It is believed that antibodies raised against linear sequences that recognize free ends of soluble tau proteins (e.g., protein/peptides created by cleavage of tau) can directly inhibit polymerization of tau.

Various procedures known in the art may be used for the production of antibodies specific to the neoepitopes created by cleavage of the tau-protein (e.g., antibodies which recognize a sequence out of SEQ ID No. 7-94 or 116, or any fragment thereof, in the truncated tau, and do not recognize the same sequence of amino acid when present in the normal tau protein). Such antibodies include but are not limited to polyclonal, monoclonal, chimeric, humanized, single chain, Fab fragments and a Fab expression library. For the production of antibodies, various host animals may be immunized by injection with a particular truncated tau-protein, or a synthetic tau-peptide, or immunogenic portions thereof, which may or may not be conjugated (e.g., to bovine serum albumin), including but not limited to rabbits, mice, rats, etc. using standard immunization protocol (Taggert and Samloff, 1983). Following the completion of immunization, a fusion procedure may be performed using, e.g., splenocytes from the hyperimmunized mice and an appropriate myeloma cell-line SP2/0 Ag14 (ATCC CRL 1581, NS-1 (ATCC TIB18), or equivalent, by using, e.g., polyethylene glycol, and successful fusion products may be selected by means of HAT media and viable hybridoma colonies may then be grown out in well plates. The wells containing successful fusion products may then be screened using, e.g., using ELISA (e.g., specificity and binding affinities) and antibodies selective for free end specific truncated tau proteins or immunogenic portions thereof, and showing no binding and/or no reactivity to a normal tau may be isolated.

Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanin, dinitrophenol, and potentially useful human adjuvants such as BCG (bacille Calmette-Guerin) and *corynebacterium parvum*. In certain embodiments, the adjuvant is alum.

In one preferred embodiment, methods for generating antibodies that are free end specific for internal cleavage sites of tau are the same as the methods described in U.S. Pat. No. 7,901,689 and corresponding EP Patent No. 2203433 (Intellect "Recall-Vax"), except that the free N- or C-terminal end-specific epitope from a truncated tau, instead of an end-specific N- or C-terminal B-cell epitope of a naturally-occurring internal peptide cleavage product of a precursor or mature protein described in U.S. Pat. No. 7,901,689, is used. These patent filings, hereby incorporated by reference, provide methods for generating antibodies that are free end specific for internal cleavage sites of certain proteins. In certain embodiments of the present invention, a chimeric peptide or a mixture of chimeric peptides in which the free N- or C-terminal end-specific epitope from a truncated tau (instead of an end-specific N- or C-terminal B-cell epitope of a naturally-occurring internal peptide cleavage product of a precursor or mature protein described in U.S. Pat. No. 7,901,689) is fused with or without spacer amino acid residue(s) to a T helper cell epitope from a different source. The chimeric peptide or peptides are then used in an immunizing composition for immunizing a mammal against the free N-terminus or free C-terminus of an internal peptide cleavage product which is a self-molecule of the immunized mammal (i.e., a truncated tau). More specifically as a preferred embodiment of the present invention, the chimeric peptide(s) have an N- or C-terminal end-specific truncated tau epitope, which is the first two to ten or the first two to five amino acid residues of the N-terminus or the last two to ten or the last two to five amino acid residues of the C-terminus of a truncated tau peptide fused to a T helper cell epitope. When such chimeric peptide(s) are administered to a human individual as part of an immunizing composition, that individual will be immunized against the truncated tau peptide or peptides from which the end-specific epitope is derived.

It is well-known that antibody responses produced by B cells to a defined region of a protein or peptide require that T helper cells of the immune system recognize another part of that antigen simultaneously. This is commonly referred to as B/T cell collaboration. According to one aspect of the present invention, this phenomenon can be mimicked by making a synthetic chimeric peptide which contains both B and T cell epitopes in a contiguous linear sequence. Such chimeric peptides have been used very successfully to drive antibody production in mice, human/mice chimeras and primates (Sharma et al., 1993; Ifversen et al., 1995; O'Hern et al., 1997). In some of these embodiments, the epitope containing the first two to twenty, two to ten or two to five amino acid residues of the free N-terminus or the last two to five, two to ten, five to thirty, ten to twenty five, or fifteen to twenty five amino acid residues of the free C-terminus of a truncated tau (e.g., ΔTau) is fused, with or without spacer amino acid residues, to a known strong T helper cell epitope to form a chimeric peptide. A non-limiting example of such a known strong T cell epitope is the well-studied tetanus toxoid promiscuous epitope of SEQ ID NO:95. Immunization with the chimeric peptides(s) containing a truncated tau end-specific epitope fused with the promiscuous T helper cell epitope of tetanus toxoid, as a preferred embodiment, should give rise to antibodies specific to that truncated tau.

The desired anti-N-terminal or anti-C-terminal end-specific truncated tau antibodies raised by the method for immunization according to the present invention are able to discriminate between a truncated tau (e.g., caspase-cleaved tau (e.g., ΔTau)) and the tau from which it is proteolytically derived (untruncated tau (e.g., the longest isoform of tau). These end-specific truncated tau antibodies bind specifically to the terminus/end of a truncated tau to slow down, reduce or prevent the accumulation, aggregation and/or polymerization of the truncated tau (either in soluble form, or conformationally different form than tau).

Single-chain antibodies as free end-specific molecules for the N- or C-terminus of truncated tau (e.g., ΔTau) can also be produced according to the present invention. These single chain antibodies can be single chain composite polypeptides having free end-specific truncated tau binding capability and comprising a pair of amino acid sequences homologous or analogous to the variable regions of an immunoglobulin light and heavy chain (linked $V_H$-$V_L$, or single chain Fv). Both $V_H$ and $V_L$ may copy natural antibody sequences, or one or both of the chains may comprise a CDR construct of the type described in U.S. Pat. No. 5,091,513. The separate polypeptides analogous to the variable regions of the light and heavy chains are held together by a peptide linker. Methods of production of such single chain antibodies, e.g., single Fv (scFv), particularly where the DNA encoding the polypeptide structures of the $V_H$ and $V_L$ chains are characterized or can be readily ascertained by sequence analysis, may be accomplished in accordance with the methods described, for example, in U.S. Pat. No. 4,946,778, U.S. Pat. No. 5,091,513, U.S. Pat. No. 5,096,815, Biocca et al., 1993, Duan et al., 1994, Mhashilkar et al., 1995, Marasco et al., 1993, and Richardson et al., 1995. FIGS. 3A-3D (from Biocca et al., 1995) schematically show an intact antibody (FIG. 3A), a Fab fragment (FIG. 3B), a Fv fragment consisting of a non-covalently linked variable region complex (V, –V, (FIG. 3C) and a single chain Fv antibody (FIG. 3D).

Theo and co-workers (1993; 1994) established that there is a length of five amino acids for any given peptide which ensures that the specific free group at the N-terminus constitutes an essential part of the epitope recognized by the new antibody. Thus, an antibody generated against an immunogenic peptide may be or is evaluated for the selectivity of the antibody in its recognition of a free N- or C-terminus of a truncated tau protein. A competitive inhibition assay, using Enzyme-Linked Immunosorbant Assay (ELISA) or immunoprecipitation with peptides corresponding to different regions of the truncated tau protein, and the region immediately preceding caspase cleavage site in the extracellular domain of tau protein, can determine the selectivity of the antibody.

Those of skill in the art will appreciate that a cysteine residue can be added to the end of the above immunogenic peptides opposite from the end corresponding to the free N-terminus or the free C-terminus of truncated tau protein to facilitate coupling to a carrier protein. For example, a cysteine residue may be added to peptides of any one of SEQ ID NOS: 7-94, or 116 (e.g., SEQ ID NO: 14, SEQ ID NO: 32, SEQ ID NO: 41, SEQ ID NO: 49, SEQ ID NO: 59, SEQ ID NO: 68, SEQ ID NO: 77, or SEQ ID NO: 94). Keyhole limpet hemocyanin (KLH), ovalbumin and bovine serum albumin (BSA) are non-limiting examples of proteins that can be used as carriers for immunogens. The presence of an N-terminal or C-terminal cysteine residue on the synthetic immunogen peptides provides a free sulfhydryl group for covalent coupling to a maleimide-activated protein. A heterobifunctional reagent, such as an N-madeimido-6-aminocaproyl ester or a m-maleimidobeczoyl-N-hydroxysuccinimide ester (MBS), is used to covalently couple the synthetic immunogenic peptide to the carrier protein (see for example, Hartlow, E. et al., Antibodies A Laboratory Manual, Cold Spring Harbor Laboratory Press, Cold Spring Harbor, N.Y. 1988). Commercial kits are also readily available for use in coupling peptide antigens to maleimide-activated large carrier proteins.

The invention further provides a hybridoma cell producing monoclonal antibody, a polyclonal antibody or a single chain antibody that is free end-specific for the free N-terminus or the C-terminus of a truncated tau protein (e.g., tau1-13, tau14-441, tau14-391, tau391-414, tau1-391, tau1-421, tau14-421, tau14-410, tau391-410, tau14-412, tau391-412, tau 14-383, tau14-381, or tau 14-355) or a fragment thereof and discriminates between a truncated tau protein and the tau protein precursor from which it is proteolytically derived. In certain embodiments, the hybridoma produces antibodies which are specific to the neoepitopes formed by the truncation of tau, the neoepitopes comprising a sequence selected from SEQ ID No 7-94 or 116, or fragment thereof. In certain embodiments, the hybridoma produces antibodies specific for ΔTau. The hybridomas producing the monoclonal antibodies of the present invention are produced following the general procedures described by Kohler and Milstein, Nature, 256, p. 495 (1975). In that procedure, hybridomas are prepared by fusing antibody-producing cells (typically spleen cells of mice previously immunized with an amyloid beta as antigen source) to cells from an immortal tumor cell line using somatic cell hybridization procedures.

For the production of antibodies, various hosts including goats, rabbits, rats, mice, humanized mice, humans, and others may be immunized by injection with the relevant epitope or with any fragment or oligopeptide thereof, which has immunogenic properties. Depending on the host species, various adjuvants may be used to increase immunological response. Such adjuvants include, but are not limited to, Freund's, mineral gels such as aluminum hydroxide, and surface-active substances such as lysolecithin, pluronic polyols, polyanions, peptides, oil emulsions, KLH, and dinitrophenol. In certain embodiments, the adjuvant is alum.

Immunostimulatory agents or adjuvants have been used for many years to improve the host immune responses, e.g. to vaccines. Intrinsic adjuvants, such as lipopolysaccharides, normally are the components of the killed or attenuated bacteria used as vaccines. Extrinsic adjuvants are immunomodulators which are typically non-covalently linked to antigens and are formulated to enhance the host immune responses. Thus, adjuvants have been identified that enhance the immune response to antigens delivered parenterally. Some of these adjuvants are toxic, however, and can cause undesirable side-effects, making them unsuitable for use in humans and many animals. Indeed, only aluminum hydroxide and aluminum phosphate (collectively commonly referred to as alum) are routinely used as adjuvants in human and veterinary vaccines. The efficacy of alum in increasing antibody responses to diptheria and tetanus toxoids is well established and a HBsAg vaccine has been adjuvanted with alum as well.

The hybridomas resulting from the fusion process are allowed to grow. Thereafter, the resulting supernatants are screened using immunoassay procedures to detect antibodies present in the supernatants capable of binding to the specific antigens.

In another embodiment, combinatorial antibody library technology, i.e., antigen based selection from antibody libraries expressed on the surface of M13 filamentous phage, can be used for the generation of monoclonal antibodies and possesses a number of advantages relative to hybridoma methodologies (Huse, et al, 1989. Barbas, et al. 1991; Clackson, et at, 1991: Burton and Barbas, 1994). The antibody of the invention may be generated from phage antibody libraries. The general methodologies involved in creating large combinatorial libraries using phage display technology is described and disclosed in U.S. Pat. No. 5,223,409 issued Jun. 29, 1993.

Once monoclonal antibodies are generated, the selectivity and binding affinity (Kd) can be evaluated by ELISA, Biacore or other method. For example, in vitro bioassays can be performed on the antibodies to test for the efficacy of the truncated tau-specific antibodies in blocking tau-induced cytotoxicity. In vitro bioassays can also be performed on the antibodies to test for the lack of interference with function of the normal tau. The antibodies selective for the truncated tau, and showing no binding and/or reactivity to normal tau may then be isolated, and, further evaluated in in vivo experiments, e.g., in transgenic AD models. The in vivo experiments, if conducted, will assess safety and efficacy of the isolated antibodies, using a variety of methods to measure safety and efficacy, including, e.g., biochemical, neuropathological, imaging and cognitive tools.

Preferred antibodies may bind specifically to the aggregated form of truncated tau without binding to the dissociated form. Alternatively, an antibody may bind specifically to the dissociated form without binding to the aggregated form. An antibody may recognize other forms of tau that accumulates in AD brain and related disorders. These forms differ from the normal tau in terms of post-translational modification, glycation, proteolytic truncation, and racemization. Antibodies used in therapeutic methods usually have an intact constant region or at least a sufficient portion of the constant region to interact with an Fc receptor. Human isotype IgG1 is preferred because of it having the highest affinity of human isotypes for the FcR1 receptor on phagocytic cells. Bispecific Fab fragments can also be used, in which one arm of the antibody has specificity for tau, and the other for an Fc receptor. Some antibodies bind to tau with a binding affinity greater than or equal to about $10^6$, $10^7$, $10^8$, $10^9$, or $10^{10}$ $M^{-1}$.

Antibodies useful in accordance with the present invention (e.g., those cable of crossing the blood brain barrier) may be administered to a human patient who may be susceptible to or who is suffering from the formation of neurofibrillary tangles in order to selectively bind and treat, reduce or eliminate the neurotoxicity caused by, e.g., the target truncated tau proteins to which they selectively bind, if and when such truncated tau proteins form in vivo.

Alternatively, the antibodies may be expressed in the brain of a mammal (e.g., human patient), e.g., by administering an isolated immunogenic peptide comprising or consisting of a sequence selected from SEQ ID Nos: 7-94 or 116, or a fragment thereof, or a gene or a DNA molecule encoding for the antibody.

The antibodies used in accordance with the invention may be monoclonal antibodies and derivatives thereof either native or recombinant, immobilized, free in solution or displayed on the surface of various molecules or bacteria, viruses, or other surfaces. The antibodies may also be humanized.

Polyclonal sera typically contain mixed populations of antibodies binding to several epitopes along the length of tau. However, polyclonal sera can be specific to a particular segment of tau, such as tau379-408. Monoclonal antibodies bind to a specific epitope within the truncated tau that can be a conformational or nonconformational epitope.

In some methods, multiple monoclonal antibodies having binding specificities to different epitopes are used. Such antibodies can be administered sequentially or simultaneously.

In another embodiment, the antibodies will be produced in vivo, in the subject in need, by administering an antigen such as truncated tau peptide or fragments thereof. In certain embodiments, the antigen comprises or consists of a sequence selected from SEQ ID Nos: 7-94 or 116, or a fragment thereof. The titer of the antibodies will be determined by techniques which are known to one skilled in the art and additional antigen will be administered if required.

In another embodiment there is provided a pharmaceutical composition comprised of the antibodies described above and a method of using the composition for the inhibition of the formation of neurofibrillary tangles. The diminished presence of neurofibrillary tangles will delay the progression of the Alzheimer's disease or other diseases characterized by tau aggregation/formation of neurofibrillary tangles, in a subject in need.

In one embodiment, the composition includes an antibody in a therapeutically or prophylactically effective amount sufficient to inhibit the neurotoxicity of truncated tau, and a pharmaceutically acceptable carrier.

In preferred embodiments, the antibodies according to the present invention inhibit the activity of the desired abnormal or truncated tau protein intraneuronally and therefore can be used as intracellular drugs. These antibodies preferably recognize the tauon-specific conformation of the target (e.g., truncated) tau protein without recognizing normal human soluble tau. In other words, in preferred embodiments, the antibodies of the present invention bind to and have reactivity with the target abnormal or truncated tau protein and do not bind and show no reactivity with normal tau. The antibodies according to the certain embodiments of the present invention may be said to be "specifically reactive" to the target abnormal tau protein if it is capable of binding with that abnormal tau protein to thereby couple the molecule to the antibody. Specificity may be tested by any standard test available for detecting antibody specificity, e.g., ELISA tests, radioimmuo-assays, atomic force microscopy with cantilever-bound binding partners, etc.

In a further aspect of the invention, the antibodies according to the present invention may be used for the preparation of drug or a pharmaceutical composition for the treatment of tauopathies such as AD by biotechnological modification into single chain molecules equipped with targeting sequence able to deliver them into the neuroblastoma cells expressing tauons, where they bind the tauons and interfere with their pathological effects and increase the degradation of the abnormally truncated tau proteins.

In yet another embodiment of the invention, the antibodies of the present invention may be conjugated to a cytoptrotective agent or an agent which will facilitate and/or improve antibody's ability to cross the BBB. The cytoprotective agent may be an antioxidant (e.g, melatonin); and the agent which facilitates or improves antibody's ability to cross the BBB is a hydrophobic substance which is capable of crossing the BBB, and is generally recognized as sage (GRAS) by the United States Food and Drug Administration ("FDA"). The cytoprotective agent or the agent which facilitates or improves antibody's ability to cross the BBB may be conjugated to the antibody directly or through a linker. The linker may be selected from the group comprising or consisting of a hydrazine linker, a disulfite linker, a thioether linker, a peptide linker. In certain embodiments, the antibody is specific for ΔTau, and the cytoptrotective agent is melatonin.

2. Immunogenic Peptide

An isolated immunogenic peptide of the present invention comprises or consists of from about 2 to about 427 amino acids. In certain embodiments, the isolated immunogenic peptide comprises or consists of tau1-13, tau14-441, tau14-391, tau391-414, tau1-391, tau1-421, tau14-421, tau114-410, tau391-410, tau14-412, tau391-412, tau14-383, tau14-381, tau143-355, or a fragment of any of the foregoing.

In the preferred embodiments, the immunogenic portion of the isolated peptide comprises or consists of an amino acid sequence which is identical to or homologous with the amino acid sequence of the neoepitope created by cleavage of tau, e.g., at the glutamic acid residue Glu391, at the aspartic acid residue Asp421, or at aspartic acid residue Asp421, or a fragment of such peptide (e.g., tau1-13, tau 14-441, tau14-391, tau391-414, tau1-391, tau1-421, tau13-421, tau14-410, tau391-410, tau14-412, tau391-412, tau 14-383, tau14-381, tau 14-355, or a fragment of any of the foregoing). The immunogenic portion of the isolated peptide generally comprises from two to ten, from two to nine, from two to eight, from two to seven, from two to six, from two to five, or from two to four amino acids in a sequence identical or homologues to the sequence of these amino acids in a neoepitope created by cleavage of tau, e.g., at the glutamic acid residue Glu391, at the aspartic acid residue Asp421, or at the aspartic acid residue Asp13. In the preferred embodiments, the immunogenic sequence is selected from SEQ ID Nos. 7-94 or 116, or a fragment thereof. In some of these preferred embodiments, the isolated immunogenic peptide comprises or consists of tau1-421 (ΔTau), or a fragment thereof, wherein the immunogenic portion of the peptide comprises or consists of SEQ ID NOs: 78-86 or 116, or a fragment thereof. In certain embodiments, the immunogenic portion of the isolated peptide comprises or consists of a sequence of the last six, five, four, three or two amino acids of ΔTau. As stated above, the free end (N-terminus or C-terminus) of the isolated immunogenic peptide is part of the immunogenic fragment and is necessary for the generation of the neoepitope-specific antibodies of the present invention; and that any of the Serines and/or Threonines in the above-listed sequences may or may not be phosphorylated.

In certain embodiments, the isolated immunogenic peptide is a mimotope comprising two peptides fused together with or without spacer residues, the first peptide mimicking the structure of the neoepitope created by cleavage of tau (i.e., the amino acid sequences bound to the free N- or C-terminus portions of a peptide created by cleavage of tau) in a mammal, and the second peptide mimicking the structure of a T cell epitope derived from a different source (e.g., tetanus toxoid), which mimotope may be used for inducing an immune response in a mammal, and, in the preferred embodiments, is for use in the treatment and/or prevention of Alzheimer's disease and other tauopathies and/or in the preparation of a pharmaceutical composition for the treatment of these disorders. In the preferred embodiments, the first peptide comprises or consists of a sequence selected from SEQ ID Nos: 7-94 or 116, or a fragment thereof. In some of these embodiments, the isolated immunogenic peptide comprises or consists of tau1-421 (ΔTau), or a fragment thereof, wherein the immunogenic portion of the peptide comprises or consists of SEQ ID NOs: 78-86 or 116, or a fragment thereof.

In certain embodiments, the isolated immunogenic peptide is a chimeric peptide(s) comprising a 2-10 or 2-5 amino acid residues sequence from the B cell neoepitope created by cleavage of tau (e.g., SEQ ID Nos: 78-86 or 116), the neoepitope fused to, with or without a spacer amino acid residue(s), to a promiscuous T helper cell epitope from a different source than the B cell neoepitope in a contiguous linear sequence, resulting in a synthetic chimeric peptide. Chimeric peptides containing both B and T cell epitopes in a contiguous linear sequence have been used very successfully to drive antibody production in mice, human/mice chimeras and primates (Sharma et al., 1993; Ifversen et al., 1995; O'Hern et al., 1997), herein incorporated by reference.

The isolated immunogenic peptide of the invention (e.g., a mimotope, a chimeric peptides, etc.) can be derived from natural sources and isolated from a mammal, such as, for example, a human, a primate, a cat, a dog, a horse, a mouse, or a rat using standard protein purification techniques.

The isolated immunogenic peptide (e.g., a mimotope, a chimeric peptides, etc.) may also be synthesized chemically or produced using recombinant DNA techniques. For example, the immunogenic peptide (e.g. a truncated tau) can be synthesized by solid phase procedures well known in the art. Suitable syntheses may be performed by utilizing "T-boc" or "F-moc" procedures. Cyclic peptides can be synthesized by solid phase methods employing the well-known "F-moc" procedure and polyamide resin in a fully automated apparatus. Alternatively, those skilled in the art will know the necessary laboratory procedures to perform the process manually. Techniques and procedures for solid phase synthesis are described in Solid Phase Peptide Synthesis: A Practical Approach by E. Atherton and R. C. Sheppard, published by IRL at Oxford University Press (1989) and Methods in Molecular Biology, Vol. 35: Peptide Synthesis Protocols (ed. M. W. Pennington and B. M. Dunn), chapter 7, pp. 91-171 by D. Andreau et al., herein incorporated by reference.

In certain embodiments, the isolated chimeric peptides of the present invention can be made by synthetic chemical methods which are well known to the ordinarily skilled artisan. For example, the chimeric peptides can be synthesized using the automated Merrifield techniques of solid phase synthesis with either t-Boc or F-moc chemistry on Peptide Synthesizers such as an Applied Biosystems Peptide Synthesizer. After complete assembly of the desired chimeric peptide, the resin is treated according to standard procedures to cleave the peptide from the resin and deblock the protecting groups on the amino acid side chains. The free peptide is purified by HPLC and characterized biochemically, for example, by amino acid analysis or by sequencing. Purification and characterization methods for peptides are well-known to one of ordinary skill in the art. Alternatively, the longer linear chimeric peptides can be synthesized by well-known recombinant DNA techniques. Any standard manual on DNA technology provides detailed protocols to produce the chimeric peptides of the invention. To construct a gene encoding a chimeric peptide of the present invention, the amino acid sequence is reverse transcribed into a nucleic acid sequence, and preferably using optimized codon usage for the organism in which the gene will be expressed. Next, a synthetic gene is made, typically by synthesizing overlapping oligonucleotides which encode the peptide and any regulatory elements, if necessary. The synthetic gene is inserted in a suitable cloning vector and recombinant clones are obtained and characterized. The chimeric peptide is then expressed under suitable conditions appropriate for the selected expression system and host, and the chimeric peptide is purified and characterized by standard methods.

Alternatively, the amino acid sequence of the isolated immunogenic peptide (e.g., a mimotope, a chimeric peptides, etc.) can be introduced into an expression vector that can be expressed in a suitable expression system using techniques well known in the art, followed by isolation or purification of the expressed polypeptide of interest. A variety of bacterial, yeast, plant, mammalian, and insect expression systems are available in the art and any such expression system can be used. Optionally, a polynucleotide encoding the immunogenic peptide can be translated in a cell-free translation system.

The isolated immunogenic peptide (e.g., a mimotope, chimeric peptides, etc.) can also comprise a peptide that arise as a result of the existence of multiple genes, alternative transcription events, alternative RNA splicing events, and alternative translational and posttranslational events. The peptide can be expressed in systems, e.g., cultured cells, which result in substantially the same posttranslational modifications present as when peptide is expressed in a native cell, or in systems that result in the alteration or omission of posttranslational modifications, e.g., glycosylation or cleavage, present when expressed in a native cell.

The isolated immunogenic peptide of the invention, in certain embodiments, can be produced as a fusion protein that contains other non-tau or non-tau-derived amino acid sequences, such as amino acid linkers or signal sequences or immunogenic carriers, as well as ligands useful in protein purification, such as glutathione-S-transferase, histidine tag, and staphylococcal protein A. More than one immunogenic peptide of the invention can be present in a fusion protein. The heterologous polypeptide can be fused, for example, to the N-terminus or C-terminus of the immunogenic peptide of the invention. A polypeptide of the disclosure can also be produced as a fusion polypeptide comprising homologous amino acid sequences, i.e., other tau or tau-derived sequences.

In certain embodiments, the isolated immunogenic peptide may be linked to an immunogenic carrier molecule to form immunogens for vaccination protocols. Immunogenic carrier may comprise a material which has the property of independently eliciting an immunogenic response in a mammal and which can be linked (e.g. covalently coupled) to the immunogenic peptide or a portion thereof either directly via formation of peptide or ester bonds between free carboxyl, amino or hydroxyl groups in the peptide, and corresponding groups on the immunogenic carrier material, or alternatively by bonding through a conventional bifunctional linking group, or as a fusion protein.

The types of carriers which may be used in the immunogenic peptides of the invention will be readily known to those skilled in the art. In certain embodiments, the carrier is selected from the group comprising or consisting of virus-like particles (VLP); serum albumins (e.g., bovine serum albumin (BSA)); globulins; thyroglobulins; hemoglobins; hemocyanins (particularly Keyhole Limpet Hemocyanin (KLH)); proteins extracted from *ascaris*, inactivated bacterial toxins or toxoids such as tetanus or diptheria toxins (TT and DT) or CRM197, the purified protein derivative of tuberculin (PPD); or Protein D from *Haemophilus influenzae* (PCT Publication No. WO 91/18926) or recombinant fragments thereof (for example, Domain 1 of Fragment C of TT, or the translocation domain of DT or Protein D ⅓rd comprising the N-terminal 100 to 110 amino acids of *Haemophilus influenzae* protein D (GB 9717953. 5); polylysin; polyglutamic acid; lysine-glutamic acid copolymers; copolymers containing lysine or ornithine; liposome carriers, or the like. In certain embodiments, the immunogenic carrier is KLH. In another embodiment, the immunogenic carrier is a virus-like particle (VLP), preferably a recombinant virus-like particle.

In certain embodiments, the carrier particle is tetanus toxoid promiscuous epitope of SEQ ID NO:95. In other embodiments, the carrier particle is a peptide of any one of SEQ ID NOS: 96-115.

In certain embodiments, the immunogenic peptide may be coupled to immunogenic carriers via chemical conjugation or by expression of genetically engineered fusion partners. The coupling does not necessarily need to be direct, but can occur through linker sequences. More generally, in the case where antigenic peptides are fused, conjugated or otherwise attached to an immunogenic carrier, spacer or linker sequences are typically added at one or both ends of the antigenic peptides. Such linker sequences generally comprise sequences recognized by the proteasome, proteases of the endosomes or other vesicular compartment of the cell.

In one embodiment, the immunogenic peptide is expressed as a fusion protein with the immunogenic carrier. Fusion of the peptide can be effected by insertion into the immunogenic carrier primary sequence, or by fusion to either the N- or C-terminus of the immunogenic carrier. Hereinafter, when referring to fusion proteins of a peptide to an immunogenic carrier, the fusion to either ends of the subunit sequence or internal insertion of the peptide within the carrier sequence are encompassed. Fusion, as referred to hereinafter, may be carried out by insertion of the immunogenic peptide into the sequence of the carrier, by substitution of part of the sequence of the carrier with the immunogenic peptide, or by a combination of deletion, substitution or insertions.

One skilled in the art will easily find guidance on how to construct fusion proteins using classical molecular biology techniques. Vectors and plasmids encoding HBcAg and HBcAg fusion proteins and useful for the expression of a HBcAg and HBcAg fusion proteins have been described (Pumpens et al., Intervirology 44:98-114 (2001), Neyrinck, S. et al., Nature Med. 5:1157-1163 (1999)) and can be used in the practice of this disclosure.

Flanking amino acid residues may be added to either end of the sequence of the isolated immunogenic peptide to be fused to either end of the sequence of the subunit of a VLP, or for internal insertion of such peptidic sequence into the sequence of the subunit of a VLP. Glycine and serine residues are particularly favored amino acids to be used in the flanking sequences added to the peptide to be fused. Glycine residues confer additional flexibility, which may diminish the potentially destabilizing effect of fusing a foreign sequence into the sequence of a VLP subunit.

In certain embodiments, the isolated immunogenic peptide is chemically coupled to an immunogenic carrier, using techniques well known in the art. Conjugation can occur to allow free movement of peptides via single point conjugation (e.g. either N-terminal or C-terminal point) or as locked down structure where both ends of peptides are conjugated to either an immunogenic carrier protein or to a scaffold structure such as, e.g., a VLP. Such conjugation can be carried out via conjugation chemistry known to those skilled in the art such as via cysteine residues, lysine residues or other carboxy moieties commonly known as conjugation points such as glutamic acid or aspartic acid. Thus, for example, for direct covalent coupling it is possible to utilize a carbodiimide, glutaraldehyde or (N-[y-malcimidobutyryloxy]succinimide ester, utilizing common commercially available heterobifunctional linkers such as CDAP and SPDP (using manufacturer's instructions). Examples of conjugation of peptides, particularly cyclized peptides, to a protein carrier via acylhydrazine peptide derivatives are described in PCT Publication No. WO 03/092714. After the coupling reaction, the immunogen can easily be isolated and purified by means of a dialysis method, a gel filtration method, a fractionation method etc. Peptides terminating with a cysteine residue (preferably with a linker outside the cyclized region) may be conveniently conjugated to a carrier protein via maleimide chemistry.

3. Vaccines

A vaccine in accordance with the present invention may comprise one or more neoepitope-specific antibodies described above or the isolated immunogenic peptide described above, or a fragment thereof. The vaccine is used for inducing an immunogenic response in a mammal. In the preferred embodiments, the immunogenic response is an immunogenic reaction to pathogenic truncated tau created by cleavage and, in certain embodiments, phosphorylation of normal tau, and/or in-vivo production of the neoepitope-specific antibodies described above. In certain embodiments, the response also includes an immunogenic reaction to pathogenic Aβ peptide(s) (e.g., immunogenic reaction to the pathogenic Aβ peptide(s) and/or generation of the antibodies which are free-end specific for pathogenic Aβ peptide(s) and do not recognize, react or bind APP), in addition to the immunogenic reaction to pathogenic truncated tau created by cleavage and, in certain embodiments, phosphorylation of normal tau, and/ or in-vivo production of the neoepitope-specific antibodies described above.

In certain embodiments, the vaccine comprises the one or more neoepitope-specific antibodies described above. The presence of anti-neoepitope-specific antibodies for the truncated tau in the blood and in the extracellular space, interstitial fluid and cerebrospinal fluid of the brain, where the truncated tau is present (phosphorylated or not-phosphorylated), in certain embodiments, promotes the formation of soluble truncated tau complexes. These soluble truncated complexes may be cleared from the central nervous system by drainage of the extracellular space, interstitial fluid and cerebrospinal fluid into the general blood circulation through, e.g., the arachnoid villi of the superior sagittal sinus. In this manner, the truncated tau is prevented from aggregation into the neurofibrillary tangles. Thus, in the preferred embodiments of the invention, the anti-neoepitope-specific antibodies for the truncated tau: (i) inhibit, reduce, clear and/or eliminate tau truncated at its C-terminus, e.g., at the glutamic acid residue Glu391 or at the aspartic acid residue Asp421, or its N-terminus (e.g., at the aspartic acid residue Asp13), (ii) inhibit, reduce, clear and/or eliminate abnormal phosphorylated truncated tau (e.g., tau phosphorylated at Ser396 and/or Ser404), and/or (iii) prevent the neurofiblary tangles formation and/or increase clearance of the neurofiblary tangles, all without affecting the biological functions of the normal tau protein. In additional embodiments, the anti-neoepitope-specific antibodies may directly block polymerization of ΔTau. In the preferred embodiments, the vaccine is for use in the treatment and/or prevention of Alzheimer's disease and/or another tauopathy.

In other embodiments, the vaccine comprises the isolated immunogenic peptide described above, or a fragment thereof (a peptide of SEQ ID NO: 7-94 or 116). The immunogenic response provided by the administration of the vaccine comprising the immunogenic peptide, or a fragment thereof, in the preferred embodiments, is production of the neoepitope-specific antibodies described above.

The antibodies administered or produced in the body in response to the administration of the isolated immunogenic peptide recognize the neoepitope created by cleavage of tau (i.e., the amino acid sequences of the free N-terminus or the free C-terminus of the peptide created by cleavage of tau), but do not recognize the same sequence of amino acids present in the normal tau protein. In certain embodiments, the antibodies specifically recognize a sequence out of SEQ ID No. 7-94 or 116, or any fragment thereof, in the truncated tau, and do not recognize the same sequence of amino acid when present in the normal tau protein. In some of these embodiments, the antibodies recognize the neoepitope created by cleavage of tau at Asp421 (e.g., the neoepitope comprising or consisting of a sequence selected from SEQ ID NOs: 78-86 or 116, which may or may not be phosphorylated). In the preferred embodiments of the invention, the antibodies administered and/or produced in response to the administration of the vaccine (i) inhibit, reduce, clear and/or eliminate tau truncated at its C-terminus, e.g., at the glutamic acid residue Glu391 or at the aspartic acid residue Asp421, or its N-terminus (e.g., at the aspartic acid residue Asp13), (ii) inhibit, reduce, clear and/or eliminate abnormal phosphorylated truncated tau (e.g., tau phosphorylated at Ser396 and/or Ser404), and/or (iii) prevent the neurofiblary tangles formation and/or increase clearance of the neurofiblary tangles, all without affecting the biological functions of the normal tau protein. In the preferred embodiments, the vaccine is for use in the treatment and/or prevention of Alzheimer's disease and other tauopathies.

In certain embodiments, the vaccine comprises an isolated immunogenic peptide comprising or consisting of an amino acid sequence which is identical to or homologous with the amino acid sequence of the neoepitope created by cleavage of tau, e.g., at the glutamic acid residue Glu391, at the aspartic acid residue Asp421, or at the aspartic acid residue Asp13, or a fragment of such peptide (e.g., tau1-13, tau 14-441, tau14-391, tau391-414, tau1-391, tau1-421, tau13-410, tau391-410, tau14-412, tau391-412, tau 13-383, tau13-381, tau 13-355, or a fragment of any of the foregoing). The immunogenic portion of the peptide generally comprises from two to ten, from two to nine, from two to eight, from two to seven, from two to six, from two to five, or from two to four amino acids in a sequence identical to or homologues with the sequence of these amino acids in a neoepitope created by cleavage of tau, e.g., at the glutamic acid residue Glu391, at the aspartic acid residue Asp421, or at the aspartic acid residue Asp13. In the preferred embodiments, the immunogenic sequence is selected from SEQ ID Nos. 7-94 or 116, or a fragment thereof. In some of these embodiments, the isolated immunogenic peptide comprises or consists of tau1-421 (ΔTau), or a fragment thereof, and the immunogenic portion of the peptide comprises or consists of SEQ ID NOs: 78-86 or 116, or a fragment thereof.

In certain embodiments, the truncated tau is selected from the group consisting of tau truncated at its C-terminus at the glutamic acid residue Glu391 or at the aspartic acid residue Asp421, or a tau truncated at its N-terminus, e.g., at the aspartic acid residue Asp13. The chimeric peptide, in certain embodiments, comprises or consists of a sequence selected from SEQ ID Nos: 7-94 or 116, or a fragment thereof. In certain preferred embodiments, the truncated tau is selected from the group consisting of tau1-13, tau14-441, tau14-391, tau391-414, tau1-391, tau1-421, tau 13-421, tau14-410, tau391-410, tau14-412, tau391-412, tau 14-383, tau14-381, tau14-355, or a fragment of any of the foregoing, of any one of the six isoforms of the human tau protein. The truncated tau, in certain embodiments, may be phosphorylated at one or more of the following: Ser199, Ser202, Ser214, Ser235, Ser396, Ser404, Thr205, Thr231, and Thr212, if present. In certain embodiments, the amino acid residue comprises or consists of a sequence of any one of SEQ ID Nos: 7-94 or 116, or a fragment thereof.

In certain preferred embodiments, the truncated tau portion of the chimeric peptide is derived from B cells. It is well-known that antibody responses produced by B cells to a defined region of a protein or peptide require that T helper cells of the immune system recognize another part of that antigen simultaneously. This is commonly referred to as B/T cell collaboration. According to the present invention, this phenomenon can be mimicked by making a synthetic chimeric peptide which contains both B and T cell epitopes in a contiguous linear sequence.

In certain embodiments, the vaccine comprises a composition (e.g., a mimotope) comprising a chimeric peptide(s) comprising a 2-10 or 2-5 amino acid residue from the B cell neoepitope created by cleavage of tau, the neoepitope fused to with or without a spacer amino acid residue(s) to a promiscuous T helper cell epitope from a different source than the B cell neoepitope in a contiguous linear sequence, resulting in a synthetic chimeric peptide. Chimeric peptides containing both B and T cell epitopes in a contiguous linear sequence have been used very successfully to drive antibody production in mice, human/mice chimeras and primates (Sharma et al., 1993; Ifversen et al., 1995; O'Hern et al., 1997), herein incorporated by reference. The promiscuous T helper cell epitope ($T_h$) is generally derived from a natural source different from the source of the B neoepitope. In other words, the $T_h$ epitope is not recognized as part of a self-molecule in the mammal subject immunized according to the method of the present invention. Since truncated tau are self-molecules, they do not possess any recognizable $T_h$ epitopes, and B cell epitopes of 2 to 10 or 2-5 amino acid residues would lack any T cell epitopes altogether. Such epitopes can be provided, in certain embodiments, by specific sequences derived from potent immunogens including, e.g., tetanus toxin, pertussis toxin, the measles virus F protein and the hepatitis B virus surface antigen (HBsAg). The $T_h$ epitopes selected are preferably capable of eliciting T helper cell responses in large numbers of individuals expressing diverse MHC haplotypes. These epitopes function in many different individuals of a heterogeneous population and are considered to be promiscuous $T_h$ epitopes. Promiscuous $T_h$ epitopes provide an advantage of eliciting potent antibody responses in most members of genetically diverse population groups.

In certain embodiments, compositions in accordance with the present invention comprise a chimeric peptide(s) comprising a 2-5 amino acid residue from the free N or C terminus of a truncated tau (e.g., ΔTau) fused with or without a spacer amino acid residue(s) to a promiscuous T helper cell epitope. The promiscuous T helper cell epitope ($T_h$) is generally derived from a source different than the source of the chimeric peptide. The truncated tau is selected, e.g, from the group consisting of tau truncated at its C-terminus at the glutamic acid residue Glu391 or at the aspartic acid residue Asp421, or a tau truncated at its N-terminus, e.g., at the aspartic acid residue Asp13. In certain embodiments, the truncated tau is ΔTau. A non-limiting example of such a known strong T cell epitope is the well-studied tetanus toxoid promiscuous epitope of SEQ ID NO:95.

In certain embodiments, the vaccine is for the treatment of Alzheimer's disease, and comprises a mimotope fused with a bacterial peptide, the mimotope mimicking the structure of the neoepitope created by cleavage of tau (i.e., the amino acid sequences bound to the free N- or C-terminus portions of a peptide created by cleavage of tau) in a mammal, and the bacterial peptide comprising or consisting of a natural bacterial tetanus toxoid or equivalent. The use of the mimotope, in the preferred embodiments, prevents a possibility of an autoimmune response which does not apply to a bacterial peptide.

In certain embodiments, the vaccine comprises a mimotope mimicking the structure of the neoepitope created by cleavage of tau in a mammal, the mimotope fused, with or without spacer residues, to a bacterial peptide comprising or consisting of a natural bacterial tetanus toxoid or equivalent, wherein the neoepitope comprises or consists of an amino acid sequence of amino acids 1-30, or a fragment thereof, of tau; a peptide comprising or consisting of an amino acid sequence of amino acids 380-405, or a fragment thereof, of tau; and/or a peptide comprising or consisting of an amino acid sequence of amino acids 410-436, or a fragment thereof, of tau; and the mimitope is suitable for inducing an immunogenic response in a mammal. In some of these embodiments, the neoepitope comprises or consists of amino acids 16-421, 17-421, 18-421, or 19-421 of ΔTau. In the preferred embodiments, the vaccine is for use in a pharmaceutical composition for the treatment and/or prevention of Alzheimer's disease and other tauopathies.

In certain preferred embodiments, the composition providing immunization against truncated tau protein also comprises the composition providing immunization against Aβ. The composition providing immunization against Aβ are, in certain embodiments, is prepared from a chimeric peptide or mixture of chimeric peptides with an end-specific B cell epitope from a naturally-occurring internal peptide cleavage product of a precursor or mature protein, as free N-terminus or C-terminus, fused with or without spacer amino acid residue(s) to a T helper cell epitope derived from a source different than that of the internal peptide cleavage product. The composition providing immunization against Aβ are explained in detail, e.g., in the assignee's U.S. Pat. No. 7,901,689, hereby incorporated by reference in its entirety. More particularly, in such embodiments, the chimeric peptide of the present invention is represented by formula (I): N—(S)$_m$-(T$_h$)$_n$ (I); or formula (II): (T$_h$)$_n$-(S)$_m$—C (II), where:

N is the first 2, 3, 4, 5, 6, 7, 8, 9, or 10 amino acid residues from the free N-terminus of a naturally-occurring internal peptide cleavage product of any one of the six isoforms of normal tau protein, such as, e.g., tau1-13, tau 14-441, tau14-391, tau391-414, tau1-391, tau1-421, tau13-410, tau391-410, tau14-412, tau391-412, tau 13-383, tau13-381, tau 13-355, or a fragment of any of the foregoing;

C is the last 2, 3, 4, 5, 6, 7, 8, 9, or 10 amino acid residues from the free C-terminus of the naturally-occurring internal peptide cleavage product (e.g., ΔTau) of any one of the six isoforms of normal tau protein;

$T_h$ is a T helper cell epitope derived from a natural source (i.e., species of living organism) different from that of the naturally-occurring internal peptide cleavage product;

S is a spacer amino acid residue(s);

m is 0, 1, 2, 3, 4, or 5; and n is 1, 2, 3, or 4.

The embodiments, the chimeric peptide of the '689 patent is represented by formula (I): N—(S)$_m$-(T$_h$)$_n$ (I); or formula (II): (T$_h$)$_n$-(S)$_m$—C (II), where:

N is the first 2, 3, 4 or 5 amino acid residues from the free N-terminus of a naturally-occurring internal peptide cleavage product, such as an Aβ peptide, which, when naturally-occurring in a mammal, is derived from a precursor protein or a mature protein;

C is the last 2, 3, 4 or 5 amino acid residues from the free C-terminus of the naturally occurring internal peptide cleavage product;

$T_h$ is a T helper cell epitope derived from a natural source (i.e., species of living organism) different from that of the naturally-occurring internal peptide cleavage product;

S is a spacer amino acid residue(s);

m is 0, 1, 2, 3, 4, or 5; and n is 1, 2, 3, or 4.

In certain embodiments, the vaccine comprises (i) a mimotope mimicking the structure of the neoepitope created by cleavage of tau in a mammal (e.g., at Asp421), the mimotope fused, with or without spacer residues, to a bacterial peptide comprising or consisting a structure of a T cell epitope derived from a different source (e.g., tetanus toxoid); and (ii) a mimotope mimicking the structure of the neoepitope created by cleavage of Aβ in a mammal, fused, with or without spacer residues, to a bacterial peptide comprising or consisting the structure of a T cell epitope derived from a different source (e.g., tetanus toxoid). The T cell epitope in the first mimotope and the second mimotope may be the same or different. In certain embodiments, the T cell epitope in the first mimotope and in the second mimotope comprise the same structure as a well-studied tetanus toxoid promiscuous epitope of SEQ ID No: 95.

The promiscuous T helper cell epitope is, generally, a T cell epitope from tetanus toxin, pertussis toxin, diphtheria toxin, measles virus F protein, hepatitis B virus surface antigen, *Chlamydia* trachomitis major outer membrane protein, *Plasmodium falciparum circumsporozoite*, *Schistosoma mansoni* triose phosphate isomerase, or *Escherichia coli* TraT. In certain embodiments, the promiscuous T helper cell epitope is a known strong T cell epitope is the tetanus toxoid promiscuous epitope of SEQ ID NO:. 95.

In certain embodiments, the T helper cell epitopes in the chimeric peptide of the present invention are selected not only for a capacity to cause immune responses in most members of a given population, but also for a capacity to cause memory/recall responses. When the mammal is human, the vast majority of human subjects/patients receiving immunotherapy with the chimeric peptide of the present invention will already have been immunized with the pediatric vaccines (i.e., MMR and diphtheria+pertussis+tetanus vaccines) and, possibly, the hepatitis B virus vaccine. These patients have therefore been previously exposed to at least one of the $T_h$ epitopes present in chimeric pediatric vaccines. Prior exposure to a $T_h$ epitope through immunization with the standard vaccines should establish $T_h$ cell clones which can immediately proliferate upon administration of the chimeric peptide (i.e., a recall response), thereby stimulating rapid B cell responses to the chimeric peptide. In addition, the $T_h$ epitopes avoid any pathogen-specific B cell and/or suppressor T cell epitopes which could lead to carrier-induced immune suppression, a problem encountered when toxin molecules are used to elicit T helper cell responses.

The $T_h$ epitopes in the chimeric peptide of the invention are promiscuous but not universal. This characteristic means that the $T_h$ epitopes are reactive in a large segment of an outbred population expressing different MHC antigens (reactive in 50 to 90% of the population), but not in all members of that population. To provide a comprehensive, approaching universal, immune reactivity for an internal peptide cleavage product, a combination of chimeric peptides with different $T_h$ epitopes can be prepared. For example, a combination of four chimeric peptides with promiscuous $T_h$ epitopes from tetanus and pertussis toxins, measles virus F protein and HBsAg may be more effective.

Promiscuous $T_h$ epitopes often share common structural features. For example, promiscuous $T_h$ epitopes range in size from about 15 to about 30 residues. Amphipathic helices are a common feature of the $T_h$ epitopes. An amphipathic helix is defined by an α-helical structure with hydrophobic amino acid residues dominating the surrounding faces. $T_h$ epitopes frequently contain additional primary amino acid patterns such as a Gly or a charged reside followed by two to three hydrophobic residues followed in turn by a charged or polar residue. This pattern defines Rothbard sequences. $T_h$ epitopes often obey the 1, 4, 5, 8 rule, where a positively charged residue is followed by hydrophobic residues at the fourth, fifth and eighth positions after the charged residue. Since all of these structures are composed of common hydrophobic, charged and polar amino acids, each structure can exist simultaneously within a single $T_h$ epitope.

$T_h$ is therefore a sequence of amino acids (natural or non-natural) that contain a $T_h$ epitope. The $T_h$ epitope can be a continuous or discontinuous epitope. Hence, not every amino acid of $T_h$ is necessarily part of the epitope. Accordingly, $T_h$ epitopes, including analogs and segments of $T_h$ epitopes, are capable of enhancing or stimulating an immune response to the internal peptide cleavage product. Immunodominant $T_h$ epitopes are broadly reactive in animal and human populations with widely divergent MHC types (Celis et al., 1988; Demotz et al., 1989; and Chong et al., 1992). The $T_h$ domain of the chimeric peptides of the present invention has from about 10 to about 50 amino acids residues and preferably from about 10 to about 30 amino acids residues. When multiple $T_h$ epitopes are present, then each $T_h$ epitope is independently the same or different.

$T_h$ epitope analogs include substitutions, deletions and insertions of one to about five amino acid residues in the $T_h$ epitope. $T_h$ segments are contiguous portions of a $T_h$ epitope that are sufficient to enhance or stimulate an immune response to the internal peptide cleavage product. An example of $T_h$ segments is a series of overlapping peptides that are derived from a single longer peptide.

The $T_h$ epitopes of the present invention include, e.g., hepatitis B surface antigen T helper cell epitopes ($HB_s\ T_h$); pertussis toxin T helper cell epitopes (PT $T_h$); tetanus toxin T helper cell epitopes (TT $T_h$); measles virus F protein T helper cell epitope ($MV_E\ T_h$); *Chlamydia* trachomitis major outer membrane protein T helper cell epitopes (CT $T_h$); diphtheria toxin T helper cell epitopes (DT $T_h$); *Plasmodium falciparum* circumsporozoite T helper cell epitopes (PF $T_h$); *Schistosoma mansoni* triose phosphate isomerase T helper cell epitopes (SM $T_h$); *Escherichia coli* TraT T helper cell epitopes (TraT $T_h$), and immune-enhancing analogs or any of the foregoing. The epitopes of these T helper cells are as provided in Table 1:

TABLE 1

| T helper cell | Epitope |
| --- | --- |
| $TT_O\ T_H$ | SEQ ID NO: 96 |
| $HB_3\ T_H$ | SEQ ID NO: 97 |
| $TT_1\ T_H$ | SEQ ID NO: 98 |
| $TT_1\ T_H$ | SEQ ID NO: 99 |
| $TT_2\ T_H$ | SEQ ID NO: 100 |
| $PT_{14}\ T_H$ | SEQ ID NO: 101 |
| $TT_3\ T_H$ | SEQ ID NO: 102 |
| $PT_2\ T_H$ | SEQ ID NO: 103 |
| $MV_{F1}\ T_H$ | SEQ ID NO: 104 |
| $MV_{F2}\ T_H$ | SEQ ID NO: 105 |
| $TT_4\ T_H$ | SEQ ID NO: 106 |
| $TT_5\ T_H$ | SEQ ID NO: 107 |
| $CT_1\ T_H$ | SEQ ID NO: 108 |
| $DT_1\ T_H$ | SEQ ID NO: 109 |
| $DT_2\ T_H$ | SEQ ID NO: 110 |
| $PF\ T_H$ | SEQ ID NO: 111 |
| $SM\ T_H$ | SEQ ID NO: 112 |
| $TraT_1\ T_H$ | SEQ ID NO: 113 |
| $TraT2\ T_H$ | SEQ ID NO: 114 |
| $TraT3\ T_H$ | SEQ ID NO: 115 |

In certain embodiments, the vaccine comprises a chimeric peptides(s) comprising a 2-10 or 2-5 amino acid residue from the B cell neoepitope created by cleavage of tau, the neoepitope fused to, with or without a spacer amino acid residue(s), to tetanus toxoid promiscuous epitope of SEQ ID NO:95 in a contiguous linear sequence. Immunization with the chimeric peptides(s) comprising a 2-10 or 2-5 amino acid residue from the B cell neoepitope created by cleavage of tau, the neoepitope fused to with or without a spacer amino acid residue(s) to tetanus toxoid promiscuous epitope of SEQ ID NO:95 in a contiguous linear sequence, should give rise to the following antibodies:

(1) anti-tetanus antibody, which would be irrelevant in humans as most individuals are already sera-positive for tetanus toxoid (i.e., from previous tetanus immunizations), or which would serve as a booster for the previous tetanus immunization;

(2) anti junction antibodies, which recognize novel epitopes created by the junction joining the end-specific B-cell neoepitope created by cleavage of tau and the T helper cell epitope of tetanus toxoid, but would not recognize anything other than the immunogen itself, and therefore are not expected to produce any response in a human; and (3) anti-neoepitope-specific antibodies for the truncated tau, which are the desired antibodies sought to be raised by the method according to the present invention for inhibiting, reducing, or even perhaps reversing neurofibrillary tangles and/or clearing truncated tau from the brain of a mammal. These anti-neoepitope-specific antibodies for the truncated tau recognize the neoepitope created by cleavage of tau (i.e., the amino acid sequences of the free N-terminus or the free C-terminus of the peptide created by cleavage of tau), but do not recognize the same sequence of amino acids present in the normal tau protein. In certain embodiments, the antibodies recognize a sequence out of SEQ ID No. 7-94 or 116, or any fragment thereof, in the truncated tau, and do not recognize the same sequence of amino acid when present in the normal tau protein. In certain embodiments, these antibodies recognize (i.e., bind and show reactivity) ΔTau, and do not recognize (i.e., bind and show reactivity) htau40. The advantages of this method of immunization include, e.g.,: (1) a cheap peptide immunogen, that is readily and easily produced and controlled for quality assurance, is used in active immunization; (2) inclusion of only two to three, and perhaps up to four or five, amino acid residues from the N- or C-terminus of an internal peptide cleavage product of tau should minimize the amount of antibody produced which may react with the normal tau protein from which the truncated tau was derived (i.e., cleaved); (3) use of an independent non-self T cell epitope should break self-tolerance and allow production of antibodies to a self-antigen (Schofield et al., 1991); (4) the absence in the chimeric peptide(s) of a T cell epitope from the internal peptide cleavage product (truncated tau) should avoid any significant problems of autoimmunity, since anti-self T cell immunity underlies progression of all known autoimmune diseases; and (5) the immunization should be self-limiting and reversible, with antibody titers gradually falling off with time, since the patient's immune system is not expected to naturally encounter the combination of the truncated tau or a fragment thereof with tetanus toxin as an immunogen.

In certain embodiments, the immunogenicity can be improved through the addition of spacer residue(s) (e.g., Gly-Gly) between the promiscuous $T_h$ epitope and the B cell epitope of the chimeric peptide according to the present invention. In addition to physically separating the $T_h$ epitope from the B cell epitope, the glycine spacer residues can disrupt any artificial secondary structures created by the joining of the $T_h$ epitope with the B cell epitope, and thereby eliminate interference between the T and/or B cell responses. The conformational separation between the helper epitope and the antibody eliciting domain thus permits more efficient interactions between the presented immunogen and the appropriate $T_h$ and B cells. The amino acid residue(s) for the spacer residue(s) can be naturally-occurring amino acids or non-naturally-occurring amino acids, which include, but are not limited to β-alanine, ornithine, norleucine, norvaline, hydroxyproline, thyroxine, gamma-amino butyric acid, homoserine, citrulline and the like.

In certain embodiments, an immunostimulatory epitope of the invasin protein of a *Yersinia* species can be linked to the T helper cell epitope of the chimeric peptide opposite from the B cell epitope, as an optional segment to the chimeric peptide. The invasions of the pathogenic bacteria *Yersinia* spp. are outer membrane proteins which mediate entry of the bacteria into mammalian cells (Isberg et al., 1990). Invasins of cultured mammalian cells by the bacterium was demonstrated to require interaction between the *Yersinia* invasin molecule and several species of the 131 family of integrins present on the cultured cells (Tran Van Nhieu et al., 1991). Since T lymphocytes are rich in 131 integrins (especially activated immune or memory T cells) the effects of invasin on human T cell have been investigated (Brett et al., 1993). It is thought that integrins facilitate the migration of immune T cells out of the blood vessels and through connective tissues to sites of antigenic challenge through their interaction with extracellular matrix proteins including fibronectin, laminin and collagen. The carboxy-terminus of the invasin molecule was found to be co-stimulatory for naive human $CD4^+$ T in the presence of the non-specific mitogen, anti-CD3 antibody, causing marked proliferation and expression of cytokines. The specific invasin domain which interacts with the 131 integrins to cause this stimulation also was identified (Brett et al., 1993). Because of the demonstrated T cell co-stimulatory properties associated with this domain, it can be linked to the promiscuous $T_h$ epitope in the chimeric peptide of the present invention opposite from the B cell epitope.

In certain embodiments, a lipid common to bacterial membrane proteins, can be coupled to synthetic peptides representing either B cell or cytotoxic T cell epitopes. Many of the outer membrane proteins of Gram-negative bacteria are both lipid-modified and very immunogenic. Because of the apparent correlation between covalent lipid linkage and immunogenicity, tripalmitoyl-5-glycerol cysteine ($Pam_3Cys$), a lipid common to bacterial membrane proteins, can be coupled to synthetic peptides representing either B cell or cytotoxic T cell epitopes. Because significant adjuvanting responses are elicited by this lipid linkage, promiscuous $T_h$ epitope of the chimeric peptide can be lipid modified opposite its linkage to the B cell epitope. Such lipid-modified chimeric peptides are likely to be more immunogenic than the unmodified version of the same peptide. U.S. Pat. No. 5,843,446, which includes a disclosure of $T_h$ epitopes and the immunostimulatory properties of invasin epitopes and lipid moieties, is herein incorporated entirely by reference.

The vaccine may optionally or preferably also include immunostimulatory agents or adjuvants. Adjuvants have been used for many years to improve the host immune responses, e.g. to vaccines. Intrinsic adjuvants, such as lipopolysaccharides, normally are the components of the killed or attenuated bacteria used as vaccines. Extrinsic adjuvants are immunomodulators which are typically non-covalently linked to antigens and are formulated to enhance the host immune responses. Thus, adjuvants have been identified that enhance the immune response to antigens delivered parenterally. Some of these adjuvants are toxic, however, and can cause undesirable side-effects, making them unsuitable for use in humans and many animals. Indeed, only aluminum hydroxide and aluminum phosphate (collectively commonly referred to as alum) are routinely used as adjuvants in human and veterinary vaccines. The efficacy of alum in increasing antibody responses to diptheria and tetanus toxoids is well established and a HBsAg vaccine has been adjuvanted with alum as well.

A wide range of extrinsic adjuvants can provoke potent immune responses to antigens. These include saponins complexed to membrane protein antigens (immune stimulating complexes), pluronic polymers with mineral oil, killed mycobacteria in mineral oil, Freund's complete adjuvant, bacterial products, such as muramyl dipeptide (MDP) and lipopolysaccharide (LPS), as well as lipid A, and liposomes. To efficiently induce humoral immune responses (HIR) and cell-mediated immunity (CMI), immunogens are emulsified in adjuvants. Many adjuvants are toxic, inducing granulomas, acute and chronic inflammations (Freund's complete adjuvant, FCA), cytolysis (saponins and Pluronic polymers) and pyrogenicity, arthritis and anterior uveitis (LPS and MDP). Although FCA is an excellent adjuvant and widely used in research, it is not licensed for use in human or veterinary vaccines because of its toxicity. In certain embodiments, the adjuavant is alum.

U.S. Pat. No. 4,855,283 teaches glycolipid analogues including N-glycosylamides, N-glycosylureas and N-glycosylcarbamates, each of which is substituted in the sugar residue by an amino acid, as immuno-modulators or adjuvants. U.S. Pat. No. 4,258,029 teaches that octadecyl tyrosine hydrochloride (OTH) functions as an adjuvant when complexed with tetanus toxoid and formalin inactived type I, II and III poliomyelitis virus vaccine. Also, Nixon-George et al., 1990, reported that octadecyl esters of aromatic amino acids complexed with a recombinant hepatitis B surface antigen enhanced the host immune responses against hepatitis B virus.

The addition of exogenous adjuvant/emulsion formulations which maximize immune responses to the internal peptide cleavage product are preferred. The adjuvants and carriers that are suitable are those: (1) which have been successfully used in Phase I human trials; (2) based upon their lack of reactogenicity in preclinical safety studies, have potential for approval for use in humans; or (3) have been approved for use in food and companion animals.

Immunotherapy regimens which produce maximal immune responses following the administration of the fewest number of doses, ideally only one dose, are highly desirable. This result can be approached through entrapment of immunogen in microparticles. For example, the absorbable suture material poly(lactide-co-glycolide) co-polymer can be fashioned into microparticles containing immunogen. Following oral or parenteral administration, microparticle hydrolysis in vivo produces the non-toxic byproducts, lactic and glycolic acids, and releases immunogen largely unaltered by the entrapment process. The rate of microparticle degradation and the release of entrapped immunogen can be controlled by several parameters, which include (1) the ratio of polymers used in particle formation (particles with higher co-glycolide concentrations degrade more rapidly); (2) particle size, (smaller particles degrade more rapidly than larger ones); and, (3) entrapment efficiency, (particles with higher concentrations of entrapped antigen degrade more rapidly than particle with lower loads). Microparticle formulations can also provide primary and subsequent booster immunizations in a single administration by mixing immunogen entrapped microparticles with different release rates. Single dose formulations capable of releasing antigen ranging from less than one week to greater than six months can be readily achieved. Moreover, delivery of the chimeric peptide according to the present invention entrapped in microparticles can also provide improved efficacy when the microparticulate immunogen is mixed with an exogenous adjuvant/emulsion formulations.

The efficacy of the chimeric peptides can be established and analyzed by injecting an animal, e.g., mice or rats, with the chimeric peptide formulated in alum and then following the immune response to the internal peptide cleavage product.

In certain embodiments, the vaccine contains a mixture of two or more of the chimeric peptides of the present invention, e.g., to enhance immunoefficacy in a broader population and thus provide a better immune response against the truncated tau. Other immunostimulatory synthetic chimeric peptide immunogens are arrived at through modification into lipopeptides so as to provide built-in adjuvanticity for potent vaccines. The immune response to synthetic chimeric peptide immunogens of the present invention can be improved by delivery through entrapment in or on biodegradable microparticles of the type described by O'Hagan et al (1991). The immunogens can be encapsulated with or without adjuvant, including covalently attached lipid moiety such as $Pam_3Cys$, and such microparticles can be administered with an immunostimulatory adjuvant such as Freund's Incomplete Adjuvant or alum. The microparticles function to potentiate immune responses to an immunogen and to provide time-controlled release for sustained or periodic responses for oral administration, and for topical administration (O'Hagan et al., 1991).

The composition comprising an immunizing effective amount of the chimeric peptide or peptides and a pharmaceutically acceptable carrier, adjuvant, excipient, diluent, or auxiliary agent may be administered to a mammal (e.g., human) for which the truncated tau peptide is a self-molecule of the mammal.

In certain embodiments, the vaccine composition further includes a chimeric peptide or mixture of chimeric peptides with an end-specific B cell epitope from a naturally-occurring internal peptide cleavage product of a precursor or mature protein (e.g., APP), as free N-terminus or C-terminus, fused with or without spacer amino acid residue(s) to a T helper cell epitope derived from a source different than that of the internal peptide cleavage product. Such compositions are explained in detail, e.g., in the assignee's U.S. Pat. No. 7,901,689, hereby incorporated by reference in its entirety.

In certain preferred embodiments, the vaccine will comprise one or more of the chimeric peptides of the invention and a pharmaceutically acceptable carrier, excipient, diluent, or auxiliary agent, including adjuvants. The vaccine can be administered by any convenient route including subcutaneous, oral, intramuscular, or other parenteral or internal route. Similarly the vaccines can be administered as a single dose or divided into multiple doses for administration. Immunization schedules are readily determined by the ordinary skilled artisan. For example, the adjuvants or emulsifiers that can be used in this invention include alum, incomplete Freund's adjuvant, liposyn, saponin, squalene, L121, emulsigen and ISA720. In preferred embodiments, the adjuvants/emulsifiers are alum, incomplete Freund's adjuvant, a combination of liposyn and saponin, a combination of squalene and L121 or a combination of emulsigned and saponin.

In certain embodiments, the vaccine contains a mixture of two or more of the neoepitope-specific antibodies described above, e.g., to enhance immunoefficacy in a broader population and thus provide a better immune response against the truncated tau, and one or more of agent(s) selected from the group comprising or consisting of pharmaceutically acceptable carriers, adjuvants, excipients, diluents, or auxiliary agents. In some of these embodiments, the vaccine also comprises one or more antibodies specific the free N or C terminus of a truncated APP (e.g., $A\beta_{1-40}$, $A\beta_{1-42}$, $A\beta_{1-43}$, etc.).

4. Administration

Administration of the truncated tau protein, its immunogenic epitope, or an antibody specifically recognizing the protein or epitope, and/or a vaccine described above can be used as a therapy to treat or prevent Alzheimer's disease, or other tauopathy associated with the development of neurofibrillary tangles. Additionally, the administration of the truncated tau protein, its immunogenic epitope and/or antibody specifically recognizing the protein or epitope and/or the vaccine can also be used as a prophylactic treatment to prevent the onset of Alzheimer's disease, or other tauopathy associated with the neurofibrillary tangle.

Patients amenable to treatment include individuals at risk of disease but not showing symptoms, as well as patients presently showing symptoms. In the case of Alzheimer's disease, virtually anyone is at risk of suffering from Alzheimer's disease. Therefore, the present methods can be administered prophylactically to the general population without the need for any assessment of the risk of the subject patient. Such prophylactic administration can begin at, e.g., age 50 or greater. The present methods are especially useful for individuals who do have a known genetic risk of Alzheimer's disease. Such individuals include those having relatives who have experienced this disease and those whose risk is determined by analysis of genetic or biochemical markers. Genetic markers of risk toward Alzheimer's disease include mutations in the APP gene, particularly mutations, at position 717 and positions 670 and 671 referred to as the Hardy and Swedish mutations respectively. Other markers of risk are mutations in the presenilin genes, PS1 and PS2, and ApoE4, family history of AD, hypercholesterolemia or atherosclerosis. Individuals presently suffering from Alzheimer's disease can be recognized from characteristic dementia by the presence of risk factors described above. In addition, a number of diagnostic tests are available for identifying individuals who have AD. These include imaging, and/or measurement of CSF tau and Aβ42 levels. Elevated tau and decreased Aβ42 levels signify the presence of AD. Individuals suffering from Alzheimer's disease can also be diagnosed by Alzheimer's Disease and Related Disorders Association criteria.

In asymptomatic patients, treatment can begin at any age (e.g., 10, 20, 30, 40, 50, or 60). Usually, however, it is not necessary to begin treatment until a patient reaches 40, 50, 60, 70, 75 or 80. Treatment typically entails multiple dosages over a period of time. Treatment can be monitored by assaying antibody, or activated T-cell or B-cell responses to the therapeutic agent over time. If the response falls, a booster dosage is indicated. In the case of potential Down's syndrome patients, treatment can begin antenatally by administering therapeutic agent to the mother or shortly after birth.

In prophylactic applications, pharmaceutical compositions or medicaments are administered to a patient susceptible to, or otherwise at risk of, Alzheimer's disease in an amount sufficient to eliminate or reduce the risk, lessen the severity, or delay the outset of the disease, including biochemical, histologic and/or behavioral symptoms of the disease, its complications and intermediate pathological phenotypes presented during development of the disease. In therapeutic applications, compositions or medicaments are administered to a patient suspected of, or already suffering from, such a disease in an amount sufficient to cure, or at least partially arrest, the symptoms of the disease biochemical, histologic and/or behavioral), including its complications and intermediate pathological phenotypes in development of the disease. In some methods, administration of agent reduces or eliminates mild cognitive impairment in patients that have not yet developed characteristic Alzheimer's pathology. An amount adequate to accomplish therapeutic or prophylactic treatment is defined as a therapeutically- or prophylactically-effective dose. In both prophylactic and therapeutic regimes, agents are usually administered in several dosages until a sufficient immune response has been achieved. Typically, the immune response is monitored and repeated dosages are given if the immune response starts to wane.

Effective doses of the compositions of the present invention, for the treatment of the above described conditions vary depending upon many different factors, including means of administration, target site, physiological state of the patient, other medications administered, and whether treatment is prophylactic or therapeutic. Treatment dosages need to be titrated to optimize safety and efficacy. The amount of immunogen depends on whether adjuvant is also administered, with higher dosages being required in the absence of adjuvant. An additional advantage of the free end specific antibodies of the present invention in certain embodiments may be that, for equal mass dosages, dosages of antibodies that specifically bind to neoepitopes of truncated tau (e.g., ΔTau) contain a higher molar dosage of the antibodies effective in clearing and/or "inactivating," than a composition comprising a mixture of the neopitope-specific antibodies and non-specific antibodies. The amount of an immunogen for administration sometimes varies from 1-500 μg per patient and more usually from 5-500 μg per injection for human administration. Occasionally, a higher dose of 1-2 mg per injection is used. Typically about 10, 20, 50, or 100 μg is used for each human injection. The mass of immunogen also depends on the mass ratio of immunogenic epitope within the immunogen to the mass of immunogen as a whole. Typically, $10^{-3}$ to $10^{-5}$ micromoles of immunogenic epitope are used for each microgram of immunogen. The timing of injections can vary significantly from once a day, to once a year, to once a decade. On any given day that a dosage of immunogen is given, the dosage is greater than 1 μg/patient and usually greater than 10 μg patient if adjuvant is also administered, and greater than 10 μg/patient and usually greater than 100 μg/patient in the absence of adjuvant. A typical regimen consists of an immunization followed by booster injections at time intervals, such as 6 week intervals. Another regimen consists of an immunization followed by booster injections 1, 2, and 12 months later. Another regimen entails an injection every two months for life. Alternatively, booster injections can be on an irregular basis as indicated by monitoring of immune response.

For passive immunization with an antibody, the dosage ranges from about 0.0001 to 100 mg/kg, and more usually 0.01 to 5 mg/kg, of the host body weight. For example dosages can be 1 mg/kg body weight or 10 mg/kg body weight or within the range of 1-10 mg/kg. An exemplary treatment regime entails administration once per every two weeks or once a month or once every 3 to 6 months. In some methods, two or more antibodies (e.g., recombinant, monoclonal, chimeric and/or humanized) with the same or different binding specificities are administered simultaneously, in which case the dosage of each antibody administered falls within the ranges indicated. In such circumstances, the two or more antibodies may both be directed at, e.g., truncated tau. Alternatively, one or more of the antibodies may be directed at, e.g., truncated tau, and one or more additional antibodies may be directed at amyloid-β (Aβ) peptides associated with Alzheimer's disease. Antibodies are usually administered on multiple occasions. Intervals between single dosages can be hourly, daily, weekly, monthly, or yearly. In some methods, dosage is adjusted to achieve a plasma antibody concentration of 1-1000 μg/ml and in some methods 25-300 μg ml. Alternatively, antibody can be administered as a sustained release formulation, in which case less frequent administration is required. Dosage and frequency vary depending on the half-life of the antibody in the patient. In general, human antibodies show the longest half-life, followed by humanized antibodies, chimeric antibodies, and nonhuman antibodies. The dosage and frequency of administration can vary depending on whether the treatment is prophylactic or therapeutic. In prophylactic applications, a relatively low dosage is administered at relatively infrequent intervals over a long period of time. Some patients continue to receive treatment for the rest of their lives. In therapeutic applications, a relatively high dosage at relatively short intervals is sometimes required until progression of the disease is reduced or terminated, and preferably until the patient shows partial or complete amelioration of symptoms of disease. Thereafter, the patent can be administered a prophylactic regime.

Doses for nucleic acids encoding immunogens range from about 10 ng to 1 g, 100 ng to 100 mg, 1 μg to 10 mg, or 30-300 μg DNA per patient. Doses for infectious viral vectors vary from 10-100, or more, virions per dose.

The efficacy of the administration/treatment may be accessed by measuring levels of pathogenic tau in plasma and/or CSF. Based on this assessment, the dose and/or frequency of administration may be adjusted accordingly. In addition or in alternative, the efficacy of administration/treatment is accessed by monitoring the ratio of the concentration of ΔTau to htau40, or vice versa.

In addition or in alternative, the efficacy of the administration/treatment may also be accessed by amyloid plaques imaging by PET. An increase in brain's metabolism would indicate that the administration/treatment is effective. The efficacy may further be accessed by a degree of brain atrophy, as determined by MRI.

In addition or in alternative, the efficacy of the administration/treatment may be accessed by measuring the levels of IgG and IgM against ΔTau.

The safety of the administration/treatment may be accessed by monitoring for microhemorrhages and/vasogenic edema, e.g., by MRI. Based on this assessment, the dose and/or frequency of administration may be adjusted accordingly.

Antibodies and immunogens may be administered intranasally, by a subcutaneous injection, intramuscular injection, IV infusion, transcutaneously, buccally, etc., or as described in more detail below.

5. Pharmaceutical Formulations

Pharmaceutical formulations in accordance with the present invention may comprise (i) an active agent comprising or consisting of one or more neoepitope-specific antibody [ies] described above, one or more immunogenic peptide[s] described above, one or more fragment[s] of the immunogenic peptides described above, and/or one or more mimotopes described above and (ii) one or more pharmaceutically acceptable excipients. The active agent will generally comprise from about 0.01% to about 90% of the formulation, and the one or more excipients will generally comprise from about 10% to about 99.99% of the formulation. In the preferred embodiments, the formulations are used for introduction of the active agent into a body of a living mammal (e.g., a human) and are accompanied with instructions (e.g., a package insert) which recite directions for administration of the active agent into the body of the living mammal. In some of these embodiments, the formulations are used for treatment or prevention of AD and/or another tauopathy and are accompanied by the instructions which recited directions for treatment and/or prevention of AD and/or another tauopathy.

In certain embodiments, the pharmaceutical formulation comprises a plurality of antibodies which recognize and bind ΔTau and do not recognize and do not bind htau1-40, and one or more pharmaceutically acceptable excipients. The antibodies will generally comprise from about 0.01% to about 90% of the formulation, and the one or more excipients will generally comprise from about 10% to about 99.99% of the formulation. In the preferred embodiments, the pharmaceutical formulation is accompanied by instructions which recite directions for administration of the active agent into the body of the living mammal and/or directions for treatment and/or prevention of AD and/or another tauopathy.

In certain embodiments, the pharmaceutical formulation comprises an immunogen comprising or consisting of any one of SEQ ID Nos: 7-94 or 116, and one or more pharmaceutically acceptable excipients. The immunogen will generally comprise from about 0.01% to about 90% of the formulation, and the one or more excipients will generally comprise from about 10% to about 99.99% of the formulation. In the preferred embodiments, the pharmaceutical formulation is accompanied by instructions which recite directions for administration of the active agent into the body of the living mammal and/or directions for treatment and/or prevention of AD and/or another tauopathy.

Formulations administered in accordance with the present invention, e.g., truncated tau proteins, portions of truncated tau proteins, immunogenic peptides, fragments of immunogenic peptides, or the neoepitope-specific antibodies described above, can be administered by parenteral, topical, intranasal, intravenous, oral, subcutaneous, intraarterial, intracranial, intraperitoneal, intranasal, or intramuscular means for prophylactic and/or therapeutic treatment. The most typical route of administration of an immunogenic agent is subcutaneous although other routes can be equally effective. The next most common route is intramuscular injection. This type of injection is most typically performed in the arm or leg muscles. In some methods, agents are injected directly into a particular tissue where deposits have accumulated, for example intracranial injection. Intramuscular injection on intravenous infusion are preferred for administration of antibody. In some methods, particular therapeutic antibodies are injected directly into the cranium. In some methods, antibodies are administered as a sustained release composition or device, such as a Medipad™ device (Elan Pharm. Technologies, Dublin, Ireland). In certain embodiments, the adjuvant is ilum.

The pharmaceutical formulations in accordance with the present invention may also contain one or more pharmaceutical carriers and/or suitable adjuvants.

A therapeutically effective amount of the antibody of the invention may vary according to factors such as the disease state, age, sex, and weight of the individual, and the ability of the modulator to elicit a desired response in the individual. Dosage regimens may be adjusted to provide the optimum therapeutic response. A therapeutically effective amount is also one in which any toxic or detrimental effects of the modulator are outweighed by the therapeutically beneficial effects.

A "prophylactically effective amount" (e.g., of a truncated tau, a portion of truncated tau, an immunogenic peptide, a fragment of the immunogenic peptide, or an antibody specific to any of the foregoing) refers to an amount effective, at dosages and for periods of time necessary, to achieve the desired prophylactic result, such as preventing or inhibiting the rate of tau deposition, aggregation, polymerization and/or neurotoxicity in a subject predisposed to the formation of neurofibrillary tangles. A prophylactically effective amount can be determined as described above for the therapeutically effective amount. Typically, since a prophylactic dose is used in subjects prior to or at an earlier stage of disease, the prophylactically effective amount will be less than the therapeutically effective amount. A "therapeutically effective amount" refers to an amount effective, at dosages and for periods of time necessary, to achieve the desired therapeutic rest, such as slowed progression of Alzheimer's disease, delayed onset, reduction or reversal of aggregate formation and/or neurofibrillary tangles, and/or reduction or reversal of neurotoxicity. A therapeutically effective amount of the antibody of the invention may vary according to factors such as the disease state, age, sex, and weight of the individual, and the ability of the modulator to elicit a desired response in the individual. Dosage regimens may be adjusted to provide the optimum therapeutic response. A therapeutically effective amount is also one in which any toxic or detrimental effects of the modulator are outweighed by the therapeutically beneficial effects.

One factor that may be considered when determining a therapeutically or prophylactically effective amount of an antibody to truncated tau is the concentration of natural tau in a biological compartment of a subject, such as in the cerebrospinal fluid (CSF) or the plasma of the subject. It is to be noted that dosage values may vary with the severity of the condition to be alleviated. It is to be further understood that for any particular subject, specific dosage regimens could be adjusted over time according to the individual need and the professional judgment of the person administering or supervising the administration of the compositions. For example, a single bolus may be administered, several divided doses may be administered over time or the dose may be proportionally reduced or increased as indicated by the exigencies of the therapeutic situation.

The pharmaceutical composition can be administered subcutaneously, intravenously, intradermally, intramuscularly, intraperitoneally, intracerebrally, intranasally, orally, transdermally, buccally, intra-arterially, intracranially, or intracephalically. It is especially advantageous to formulate parenteral compositions in dosage unit form for ease administration and uniformity of dosage. Dosage unit form as used herein refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic effect to be achieved, and (b) the limitations inherent in the art of compounding such an active compound for the treatment of sensitivity in individuals. As used herein "pharmaceutically acceptable carrier" includes any and all solvents, dispersion media, coatings, antibacterial and antifungal agents, isotonic and absorption delaying agents, and the like that are physiologically compatible. In one embodiment, the carrier is suitable for parenteral administration. Preferably, the carrier can be suitable for intravenous, intraperitoneal or intramuscular administration. Alternatively, the carrier is suitable for administration into the central nervous system (e.g., intraspinally or intracerebrally). In another embodiment, the carrier is suitable for oral administration. Pharmaceutically acceptable carriers include sterile aqueous solutions or dispersions and sterile powders for the extemporaneous preparation of sterile injectable solutions or dispersion. The use of such media and agents for pharmaceutically active substances is well known in the art. Except insofar as any conventional media or agent is incompatible with the active compound, use thereof in the pharmaceutical compositions of the invention is contemplated. Supplementary active compounds can also be incorporated into the compositions.

Formulations prepared in accordance with the present invention typically must be sterile and stable under the conditions of manufacture and storage. The composition can be formulated as a solution, microemulsion, liposome, or other ordered structure suitable to high drug concentration. The carrier can be a solvent or dispersion medium containing, for example, water, ethol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, or sodium chloride in the composition. Prolonged absorption of the injectable compositions can be brought about by including in the composition an agent which delays absorption, for example, monostearate salts and gelatin. Moreover, the antibody can be administered in a time-release formulation, for example in a composition which includes a slow release polymer. The active compounds can be prepared with carriers that will protect the compound against rapid release, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, polylactic acid and polylactic, polyglycolic copolymers (PLG). Many methods for the preparation of such formulations are patented or generally known to those skilled in the art.

Sterile injectable solutions can be prepared by incorporating the active compound (e.g., antibody to a truncated tau in the required amount) in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Topical application can result from intransdermal or intradermal application. Topical administration can be facilitated by coadministration of the agent with cholera toxin or detoxified derivatives or subunits thereof. Alternatively, transdermal delivery can be achieved using skin patch or using transfersomes.

Other delivery systems can include time-release, delayed release or sustained release delivery systems. Such systems can avoid repeated administrations of the active compounds of the invention, increasing convenience to the subject and the physician. Many types of release delivery systems are available and known to those of ordinary skill in the art. They include polymer based systems such as polylactic and polyglycolic acids polyanhydrides and polycaprolactone; nonpolymer systems that are lipids including sterols such as cholesterol, cholesterol esters and fatty acids or neutral fats such as mono-, di and triglycerides; hydrogel release systems; silastic systems; peptide based systems; wax coatings, compressed tablets using conventional binders and excipients, partially fused implants and the like. In addition, a pump-based hardware delivery system can be used, some of which are adapted for implantation.

A long-term sustained release implant also may be used. "Long-term" release, as used herein, means that the implant is constructed and arranged to deliver therapeutic levels of the active ingredient for at least 30 days, and preferably 60 days. Long-term sustained release implants are well known to those of ordinary skill in the art and include some of the release systems described above. Such implants can be particularly useful in treating conditions characterized by aggregates of amyloid beta peptides by placing the implant near portions of the brain affected by such aggregates, thereby effecting localized, high doses of the compounds of the invention.

Immunogenic agents of the present invention, such as peptides, are sometimes administered in combination with an adjuvant. A variety of adjuvants can be used in combination with a peptide, such as tau, to elicit an immune response. Preferred adjuvants augment the intrinsic response to an immunogen without causing conformational changes in the immunogen that affect the qualitative form of the response.

A preferred class of adjuvants is aluminum salts (alum), such as aluminum hydroxide, aluminum phosphate, and aluminum sulfate. Such adjuvants can be used with or without other specific immunostimulating agents, such as 3 De-O-acylated monophosphoryl lipid A (MPL) or 3-DMP, polymeric or monomeric amino acids, such as polyglutamic acid or polylysine. Such adjuvants can be used with or without other specific immunostimulating agents, such as muramyl peptides (e.g., N-acetylmuramyl-L-threonyl-D-isoglutamine (thr-MDP), N-acetyl-normuramyl-L-alanyl-D-isoglutamine (nor-MDP), N-acetylmuramyl-L-alanyl-D-isoglutaminyl-L-alanine-2-(1'-2' dipalmitoyl-sn-1-glycero-3-hydroxyphosphoryloxy)-ethylamine (MTP-PE), N-acetylglucsaminyl-N-acetylmuramyl-L-Al-D-isoglu-L-Ala-dipalmitoxy propylamide (DTP-DPP) Theramide™), or other bacterial cell wall components. Oil-in-water emulsions include (a) MF59 (WO 90/14837 to Van Nest et al., which is hereby incorporated by reference in its entirety), containing 5% Squalene, 0.5% Tween 80, and 0.5% Span 85 (optionally containing various amounts of MTP-PE) formulated into submicron particles using a microfluidizer such as Model 110Y microfluidizer (Microfluidics, Newton Mass.), (b) SAF, containing 10% Squalene, 0.4% Tween 80, 5% pluronic-blocked polymer L121, and thr-MDP, either microfluidized into a submicron emulsion or vortexed to generate a larger particle size emulsion, and (e) Ribi™ adjuvant system (RAS), (Ribi ImmunoChem, Hamilton, Mont.) containing 2% squalene, 0.2% Tween 80, and one or more bacterial c ell wall components from the group consisting of monophosphoryllipid A (MPL), trehalose dimycolate (TDM), and cell wall skeleton (CWS), preferably MPL+CWS (Detox™). Other adjuvants include Complete Freund's Adjuvant (CFA) and Incomplete Freund's Adjuvant (IFA). Other adjuvants include cytokines, such as interleukins (IL-1, IL-2, and IL-12), macrophage colony stimulating factor (M-CSF), and tumor necrosis factor (TNF). In certain embodiments, the adjuvant is ilum.

An adjuvant can be administered with an immunogen as a single composition, or can be administered before, concurrent with, or after administration of the immunogen. Immunogen and adjuvant can be packaged and supplied in the same vial or can be packaged in separate vials and mixed before use. Immunogen and adjuvant are typically packaged with a label, indicating the intended therapeutic application. If immunogen and adjuvant are packaged separately, the packaging typically includes instructions for mixing before use. The choice of an adjuvant and/or carrier depends on the stability of the immunogenic formulation containing the adjuvant, the route of administration, the dosing schedule, the efficacy of the adjuvant for the species being vaccinated, and, in humans, a pharmaceutically acceptable adjuvant is one that has been approved or is approvable for human administration by pertinent regulatory bodies. For example, Complete Freund's adjuvant is not suitable for human administration. However, alum, MPL or Incomplete Freund's adjuvant (Chang et al., Advanced Drug Delivery Reviews 32:173-186 (1998), which is hereby incorporated by reference in its entirety) alone or optionally all combinations thereof are suitable for human administration.

Agents of the present invention are often administered as pharmaceutical compositions comprising an active therapeutic agent and a variety of other pharmaceutically acceptable components. See Remington's Pharmaceutical Science (15th ed., Mack Publishing Company, Easton, Pa., 1980), which is hereby incorporated by reference in its entirety. The preferred form depends on the intended mode of administration and therapeutic application. The compositions can also include, depending on the formulation desired, pharmaceutically-acceptable, non-toxic carriers or diluents, which are defined as vehicles commonly used to formulate pharmaceutical compositions for animal or human administration. The diluent is selected so as not to affect the biological activity of the combination. Examples of such diluents are distilled water, physiological phosphate-buffered saline, Ringer's solutions, dextrose solution, and Hank's solution. In addition, the pharmaceutical composition or formulation may also include other carriers, adjuvants, or nontoxic, nontherapeutic, nonimmunogenic stabilizers and the like.

Pharmaceutical compositions can also include large, slowly metabolized macromolecules, such as proteins, polysaccharides like chitosan, polylactic acids, polyglycolic acids and copolymers (e.g., latex functionalized sepharose, agarose, cellulose, and the like), polymeric amino acids, amino acid copolymers, and lipid aggregates (e.g., oil droplets or liposomes). Additionally, these carriers can function as immunostimulating agents (i.e., adjuvants).

For parenteral administration, agents of the present invention can be administered as injectable dosages of a solution or suspension of the substance in a physiologically acceptable diluent with a pharmaceutical carrier that can be a sterile liquid such as water, oil, saline, glycerol, or ethanol. Additionally, auxiliary substances, such as wetting or emulsifying agents, surfactants, pH buffering substances and the like can be present in compositions. Other components of pharmaceutical compositions are those of petroleum, animal, vegetable, or synthetic origin. Peanut oil, soybean oil, and mineral oil are all examples of useful materials. In general, glycols, such as propylene glycol or polyethylene glycol, are preferred liquid carriers, particularly for injectable solutions. Agents of the invention, particularly, antibodies, can be administered in the form of a depot injection or implant preparation which can be formulated in such a manner as to permit a sustained release of the active ingredient. An exemplary composition comprises monoclonal antibody at 5 mg/mL, formulated in aqueous buffer consisting of 50 mM L-histidine, 150 mM NaCl, adjusted to pH 6.0 with HCl.

Typically, compositions are prepared as injectables, either as liquid solutions or suspensions; solid forms suitable for solution in, or suspension in, liquid vehicles prior to injection can also be prepared. The preparation also can be emulsified or encapsulated in liposomes or micro particles, such as polylactide, polyglycolide, or copolymer, for enhanced adjuvant effect (Langer, et al., Science 249:1527 (1990); Hanes, et al., Advanced Drug Delivery Reviews 28:97-119 (1997), which are hereby incorporated by reference in their entirety).

Additional formulations suitable for other modes of administration include oral, intranasal, and pulmonary formulations, suppositories, and transdermal applications.

For suppositories, binders and carriers include, for example, polyalkylene glycols or triglycerides; such suppositories can be formed from mixtures containing the active ingredient in the range of 0.5% to 10%, preferably 1%-2%. Oral formulations include excipients, such as pharmaceutical grades of mannitol, lactose, starch, magnesium stearate, sodium saccharine, cellulose, and magnesium carbonate. These compositions take the form of solutions, suspensions, tablets, pills, capsules, sustained release formulations or powders and contain 10%-95% of active ingredient, preferably 25%-70%.

Topical application can result in transdermal or intradermal delivery. Topical administration can be facilitated by co-administration of the agent with cholera toxin or detoxified derivatives or subunits thereof or other similar bacterial toxins (See Glenn et al., Nature 391:851 (1998), which is hereby incorporated by reference in its entirety). Co-administration can be achieved by using the components as a mixture or as linked molecules obtained by chemical crosslinking or expression as a fusion protein. Alternatively, transdermal delivery can be achieved using a skin path or using transferosomes (Paul et al., Eur. J. Immunol. 25:3521-24 (1995); Cevc et al., Biochem. Biophys. Acta 1368:201-15 (1998), which are hereby incorporated by reference in their entirety).

6. Combination Therapy

Another aspect of the present invention is a combination therapy wherein peptide immunogens of both truncated tau and Aβ ("mimotopes") are employed as a combination therapy to a mammal (e.g., human) in need thereof. Thus, in certain embodiments, a truncated tau protein, its immunogenic epitope, or antibodies specific for the truncated tau protein or immunogenic epitope is (are) administered in combination with each other and/or other agents that are effective for treatment of related neurodegenerative diseases.

In the case of amyloidogenic diseases such as Alzheimer's disease and Down's syndrome, immune modulation to clear amyloid-beta (Aβ) deposits is an emerging therapy Immunotherapies targeting Aβ have consistently resulted in cognitive improvements. It is likely that tau and Aβ pathologies are synergistic. Therefore, a combination therapy targeting the clearance of both pathologies at the same time may be more effective than targeting each individually. In the case of Parkinson's Disease and related neurodegenerative diseases, immune modulation to clear aggregated forms of the α-synuclein protein is also an emerging therapy. A combination therapy which targets the clearance of both tau and -synuclein proteins simultaneously may be more effective than targeting each individually.

In certain preferred embodiments, the therapy of the present invention is combined with the therapies disclosed in applicant's previous filing U.S. Patent Publication No. 2003/0073655 (U.S. Ser. No. 10/084,380), hereby incorporated by reference in its entirety. That invention relates to the use of antibodies to amyloid β peptides as a method to selectively inhibit accumulation and/or neutralize the cytotoxicity associated with amyloid B species, and in certain preferred embodiments specifically Aβ1-40 (which forms the bulk of circulating amyloid B peptide human CSF, plasma, and urine), or the more toxic but less abundant Aβ1-42 and Aβ1-43 species that can seed amyloid deposition. In certain further preferred embodiments, the invention is directed to a vaccine which is a combination of a composition providing immunization against truncated tau protein and a composition providing immunization against Aβ.

In certain preferred embodiments, the composition providing immunization against truncated tau protein and the composition providing immunization against Aβ are administered to a mammal in the same or different formulations. In certain preferred embodiments, the composition providing immunization against truncated tau protein and/or the composition providing immunization against Aβ are prepared from a chimeric peptide or mixture of chimeric peptides with an end-specific B cell epitope from a naturally-occurring internal peptide cleavage product of a precursor or mature protein, as free N-terminus or C-terminus, fused with or without spacer amino acid residue(s) to a T helper cell epitope derived from a source different than that of the internal peptide cleavage product. More particularly, in such embodiments, the composition providing immunization against truncated tau protein is represented by

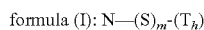formula (I): N—(S)$_m$-(T$_h$)  (I); or

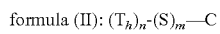formula (II): (T$_h$)$_n$-(S)$_m$—C  (II), where:

N is the first 2, 3, 4, 5, 6, 7, 8, 9, or 10 amino acid residues from the free N-terminus of a naturally-occurring internal peptide cleavage product of any one of the six isoforms of normal tau protein, such as, e.g., tau1-13, tau 14-441, tau14-391, tau391-414, tau1-391, tau1-421, tau13-410, tau391-410, tau14-412, tau391-412, tau 13-383, tau13-381, tau 13-355, or a fragment of any of the foregoing;

C is the last 2, 3, 4, 5, 6, 7, 8, 9, or 10 amino acid residues from the free C-terminus of the naturally-occurring internal peptide cleavage product of any one of the six isoforms of normal tau protein;

T$_h$ is a T helper cell epitope derived from a natural source (i.e., species of living organism) different from that of the naturally-occurring internal peptide cleavage product;

S is a spacer amino acid residue(s);

m is 0, 1, 2, 3, 4, or 5; and n is 1, 2, 3, or 4.

The composition providing immunization against Aβ is represented by

formula (I): N—(S)$_m$-(T$_h$)$_n$  (I); or

formula (II): (T$_h$)$_n$-(S)$_m$—C  (II), where:

N is the first 2, 3, 4 or 5 amino acid residues from the free N-terminus of a naturally-occurring internal peptide cleavage product, such as an Aβ peptide, which, when naturally-occurring in a mammal, is derived from a precursor protein or a mature protein;

C is the last 2, 3, 4 or 5 amino acid residues from the free C-terminus of the naturally occurring internal peptide cleavage product;

T$_h$ is a T helper cell epitope derived from a natural source (i.e., species of living organism) different from that of the naturally-occurring internal peptide cleavage product;

S is a spacer amino acid residue(s);

m is 0, 1, 2, 3, 4, or 5; and n is 1, 2, 3, or 4.

In certain embodiments, the combination therapy employs one or more antibodies specific for the neoepitope created by cleavage of tau (e.g., at Asp421), and one or more antibodies specific for the neoepitope created by cleavage of APP. The one or more antibodies specific for the neoepitope created by cleavage of tau may be any antibody described above in the section "Antibodies to Truncated Tau." The one or more antibodies specific for the neoepitope created by cleavage of APP include, e.g., antibodies which is specific for the free end(s) of Aβ peptides, conformation specific antibodies for these peptides and antibodies which bind to mid-domains of these peptides. In certain embodiments, the one or more antibodies specific for the neoepitope created by cleavage of APP is an antibody which is free end-specific for Aβ peptides (Aβ1-39, Aβ1-40, Aβ1-41, Aβ1-42, Aβ1-43, etc.) and/or internal cleavage sites at positions 11 and 17 of any of the foregoing, which may or may not have pyroglutamate modifications as a natural occurrence. In certain embodiments, the one or more antibodies specific for the neoepitope created by cleavage of APP may be selected from a group comprising or consisting of bapineuzumab, ponezumab, gantenerumab, solanezumab, MABT5102A and GSK933756.

The efficacy of the combination treatment may be accessed by measuring Aβ and pathogenic tau (e.g., ΔTau) levels in plasma and/or CSF. In addition or in alternative, IgG/IgM levels of Aβ and pathogenic tau (e.g., ΔTau) may be measured. In addition or in alternative, brain metabolism may be accessed by PET imaging. In addition or in alternative, cytokine profiles from the blood may also be taken. Based on these assessments, the dose and/or frequency of the administration may be adjusted.

The safety of the combination treatment may be accessed by monitoring for microhemorrhages and/or vasogenic edema, e.g., by MRI. Based on this assessment, the dose and/or frequency of administration may be adjusted accordingly. For example, upon occurrence of microhemorrhages and/or vasogenic edema, the combination treatment may be temporarily discontinued and/or doses may be decreased.

DETAILED DESCRIPTION OF PREFERRED EMBODIMENTS

The following example represents specific embodiments of the present invention, and is not representative of the entire scope of the invention.

Example 1

The strategy and the protocols for generating antibodies which specifically recognize the neoepitope created by cleavage of tau at Asp421 (i.e., ΔTau), but not full length tau (i.e., htau40) is described in this prophetic example.

The following peptides are prepared using an Applied Biosystems Peptide Synthesizer (430A): a peptide corresponding to tau416-421 (SEQ ID NO:83 SIDMVD); a peptide corresponding to tau417-421 (SEQ ID NO: 84 IDMVD); a peptide corresponding to tau 418-421 (SEQ ID NO:85 DMVD); and a peptide corresponding to SEQ ID NO:86, all of htau40.

The synthetic peptides are then purified by HPLC and characterized using amino acid composition.

Once purified and characterized, the peptides are conjugated to keyhole limpet hemocyanin, and four sets 10 Balb/c mice are immunized with the conjugated peptides.

Following the completion of the immunization, a fusion procedure is performed using spleenoxytes from the hyperimmunized mice and an appropriate myeloma cell-line SP2/0-Ag14 (ATCC CRL 1581), NS-1 (ATCC TIB18), or equivalent, using polyethylene glycol.

The selection of successful fusion products are achieved by means of HAT media. Viable hybridoma colonies are grown out in 96 well plates.

Screening of all wells containing successful fusion products are carried out using a set of peptides corresponding to htau40, ΔTau, and residues 416-421, 417-421, 418-421, and 419-421 of ΔTau by ELISA assays. Based on the results of the ELISA assays, subclonings are performed by limiting dilution on the selected colonies. The antibodies specific for ΔTau, residues 416-421, 417-421, 418-421, and 419-421 of ΔTau; and not specific for tau40 are selected. These antibodies only recognize, bind or show reactivity with ΔTau, or residues 416-421, 417-421, 418-421, or 419-421 of ΔTau, and do not recognize, bind or show reactivity with tau40.

To confirm that the protocol is capable of being used subsequently to generate monoclonal antibodies which specifically recognize the neoepitope created by cleavage of tau at Asp421 (i.e., ΔTau), but not full length tau (i.e., htau40), high affinity polyclonal antibodies specific for ΔTau and non-specific for htau40 are raised using the restricted peptide: H2N-SEQ ID NO:86-aminohexanoate-C-amide. The peptide is synthesized using solid phase Fmoc chemistry. The peptide is then cleaved and analyzed by mass spectroscopy and high performance liquid chromatography (HPLC). HPLC purification is achieved using a C-18 YMC column (10μ packing, 120 A pore size, 10×250 mm) in a buffer system of A: H2O/0.1% TFA and B:CH3CN/0.08% TFA. The appropriate fractions is pooled, lyophilized, and again subjected to mass spectroscopy and HPLC analysis. The peptide is coupled to KLH for immunization, BSA for ELISA detection, with the cross-linker MBS. Rabbits are immunized at 3 week intervals, and the titer assessed by ELISA using acetal-Asp-Ser-aminohexanoate-C-amide ("spanning peptide"). This peptide corresponds to a sequence of amino acid residues that spans the 0 to 1 splice site of htau40 that yields ΔTau. The same spanning peptide is coupled to a thiol coupling gel via their cysteine residue and used to preabsorb away all antibodies which do not depend upon the free carboxy-Asp being present. The antibodies are then purified and collected using the restricted peptide. Whereas the crude serum shows substantial activity towards the spanning peptide, once affinity purified, there is no reactivity of the resulting antibody with the spanning peptide, only with the restricted peptide. This confirms that the monoclonal antibodies are specific for ΔTau and non-specific for the spanning peptide. Since these antibodies are not specific for the spanning peptide, these antibodies would also be non-specific htau40, because htau40 also does not a free C-terminus of ΔTau, which is created by cleavage of htau40 at Asp421. Accordingly, these antibodies only recognize, bind or show reactivity with ΔTau, residues 416-421, 417-421, 418-421, or 419-421 of ΔTau, and do not recognize, bind or show reactivity with tau40.

To generate monoclonal antibodies specific for the C-terminus of ΔTau, mice are immunized at 3 week intervals using: H2N-SEQ ID NO:86-aminohexanoate-C-amide conjugated to BSA prepared as described for the preparation of polyclonal. The titer in each mouse is also assessed by ELISA as described above. After spleen cell fusion of the mice containing the highest titer, several clones are isolated and screened using the spanning peptide ELISA detection method. The immunogenic peptide sequences, corresponding to the C-terminus of tau40, and conjugated to a different carrier protein, such as bovine serum albumin (BSA) and ovalbumin, are used to confirm the resultant monoclonal antibodies are end-specific for the C-terminus of ΔTau and non-specific for the carrier protein and htau40.

Optionally, the specificity of the antibodies to selectively recognize htau40 cleaved at Asp421 (i.e., ΔTau), but not full length tau is assessed in vivo, using traumatic brain injury model, a model that leads to neuronal caspase activation, in mice. Analysis shows that antibodies specifically detect tau cleaved at Asp421 (i.e., ΔTau), residues 416-421, 417-421, 418-421, or 419-421 of tau40 and do not specifically detect and do not cross-react with the full length tau (i.e., tau40). In other words, these antibodies only recognize, bind or show reactivity with ΔTau, residues 416-421, 417-421, 418-421, or 419-421 of ΔTau, and do not recognize, bind or show reactivity with htau40.

Example 2

In Example 2, the therapeutic potential of a vaccine against Aβ, tau, and in combination in a triple transgenic mouse model of Alzheimer's disease (3×Tg-AD) that expresses both plaque and tangle pathology is evaluated. A first goal of Example 2 is to evaluate such vaccines as a preventative against AD neuropathology and cognitive decline. The second goal of Example 2 is to evaluate such vaccines as a therapeutic once AD neuropathology is already established. In Example 2, the assignee's RECALL-Vax vaccine technology is utilized.

The triple transgenic mouse model contains 3 mutations relevant to Alzheimer's pathology (PS1$_{M146V}$, βAPP$_{Swe}$, and tau$_{P301L}$) (Oddo et al., 2003). (Dr. Frank LaFerla, UC Irvine). The mice were generated by microinjecting two transgenes (βAPPSwe, and tauP301L) into a single cell embryo from a homozygous presenilin-1 knock-in animal. The presenilin-1 knock-in gene contains the mutation M146V which increases the amount of Aβ1-42 produced relative to Aβ1-40. Several triple transgenic lines were derived from this approach and these lines develop critical features of Alzheimer's neuropathology in an age dependent fashion. They display plaque and tangle pathology as well as synaptic dysfunction including LTP deficits (Oddo et al., 2003). Furthermore plaque formation precedes tangle formation and so mimics the development of the disease in humans, and is accompanied by extensive inflammation, and substantial cognitive decline. Therefore the 3×Tg-AD mice represent an advanced model of AD.

Design and Methods:

Aim 1: Preventative study on RECALL-VAX™ vaccines in 3×Tg-AD mice.

6-month old homozygous 3×Tg-AD mice will be treated with either adjuvant, Anti-Amyloid RECALL-VAX vaccine, Anti-ΔTau RECALL-VAX vaccine or Combination of Anti-Amyloid and Anti-ΔTau RECALL-VAX vaccine (n=20 per group). RECALL-VAX™ is a proprietary vaccine owned by Intellect Neurosciences, an example of which is described and claimed in U.S. Pat. No. 7,901,689 (incorporated by reference in its entirety).

Twelve months later, these 3×Tg-AD mice will be tested on a battery of cognitive tasks, as detailed below. Afterwards, mice will be sacrificed and their brains extracted and then cut down the midline, for pathological analyses. Blood will also be taken for analyses.

Two groups of 3×Tg-AD mice (n=20 per group) will be sent CEA-DSV-I2BM-MIRCen, France to utilize translational in vivo and ex vivo MRI and PET imaging approaches based on biomarkers that can be potentially translated to clinical trials in humans. Some of the potential biomarkers that can be used at MIRCen facility include: Brain atrophy (MRI), Amyloid plaque imaging (MRI, AV45 PET), Ab and Tau level in plasma, Brain metabolism (FDG-PET, 2DG autoradiography), Axonal transportation, neuronal health (MEMRI), Behavior (MWM), Microhemorrhages, Vasogenic edema (MRI).

This aim will use a total of 120 3×Tg-AD mice.

Aim 2: Therapeutic study on RECALL-VAX vaccines in 3×Tg-AD mice.

12-month old homozygous 3×Tg-AD mice will be treated with either adjuvant, Anti-Amyloid RECALL-VAX vaccine, Anti-ΔTau RECALL-VAX vaccine or Combination of Anti-Amyloid and Anti-ΔTau RECALL-VAX vaccine (n=15 per group). Six months later, mice will be tested on a battery of cognitive tasks, as detailed below. Afterwards, mice will be sacrificed and their brains extracted and then cut down the midline, for pathological analyses. Blood will also be taken for analyses.

This aim will use a total of 60 3×Tg-AD mice.

Behavioral Assays

Object/Place/Context Recognition

These tasks are based on the spontaneous tendency of rodents to explore a novel object more often than a familiar object (Ennaceur and Delacour, 1988) and have been found to not be dependent on the amygdala (Moses et al., 2005).

Perirhinal cortex lesions and studies of neuronal activation and responses in rats suggest that it is cortical and not hippocampal neurons that are involved in the object recognition task (Aggleton et al., 1997; Wan et al., 1999). For the novel object task, mice will be familiarized with an empty open field for a period of 10 minutes. On the following day, mice will be subjected to a 5 minute exploration session in the same context with two identical objects (Object A; e.g. two identical balls or two identical dice) placed in symmetrical locations in the open field. 90 minutes and 24 hours later, animals will be subjected to a 3 minute retention phase test where they will be exposed to one Object A and also to a novel object, Object B (for the 90 min time point) and Object C (for the 24 hour time point) placed in the same, symmetrical locations in the open field.

A different version of the novelty task requires mice to recognize that an object is placed in a new location (Save et al., 1992; Ennaceur et al., 1997). This task is primarily dependent upon hippocampus (Mumby et al., 2002). For the novel place paradigm, mice will again be placed in the open field with two identical objects (Object D), different from the objects used for the novel object task, for 5 minutes. 90 minutes later, animals will be subjected to a 3 minute retention phase test where they will be exposed to Objects D again but with one of the object having been moved from its original location.

Another version of the novelty-preference paradigm requires mice to remember an object encountered in a particular context (Dix and Aggleton, 1999). This memory task has also been shown to be hippocampus dependent (Mumby et al., 2002). The novel context task required the mice to be familiarized with a second context. Mice will be placed in a second open field in a different room for 10 minutes. Mice will be presented with two identical objects in context 1 (Object E) and then presented with two different identical objects in context 2 (Object F). For the 90 min retention phase test, animals will be placed in context 1 with on Object E and one object from context 2 (Object F).

The time spent exploring the familiar object and the novel object will be calculated where exploration equals touching the object with nose or paws, or sniffing within 1.5 cm of the object. Time spent with the novel object as compared to time spent with both objects will be used as memory index. Scoring will be conducted independently by two blind scorers in order to eliminate experimental bias.

Morris Water Maze (Adapted from (Roozendaal et al., 2003))

The Morris Water Maze (MWM) is a test for spatial memory (i.e. hippocampus dependent) and cued learning (i.e. non-hippocampal) in rodents. Many studies in the last two decades have used this test as a reliable measure of hippocampal-dependent learning (D'Hooge and De Deyn, 2001), including several transgenic models (Hsiao et al., 1996; Hsiao, 1997).

The water maze is a circular pool filled with opaque water. Mice will be pre-trained by swimming to a plexiglass platform submerged 1.5 cm beneath the surface of the water. The location of the platform will be selected randomly each individual mouse throughout training. The maze is located in a room containing several visual, extra-maze cues. For spatial training, mice will be subjected to four trials per day for three consecutive days. Before the first trial, the mouse will be placed on the platform for 30 s. On each trial, the mouse will be placed into the tank at one of four designated staring points in a random order. Mice will be allowed to find and escape onto the submerged platform. If an animal fails to find the platform within 60 s, it will be manually guided to the platform and will remain there for 15 s.

Retention of spatial training will be assessed 1.5 and 24 hours after the last training trial. Both of these probe trials will consist of a 60 s free swim in the pool with the platform removed. Mice will be monitored by a camera mounted in the ceiling directly above the pool for subsequent analysis. The parameters measured during the probe trial will include (1) time spent in the quadrant containing the platform during training and (2) initial latency to cross platform location. The escape data will be examined with a multifactor analysis of variance (ANOVA) including genotype (transgenic vs. non-transgenic), and probe trial (1.5 and 24 hours).

Passive Inhibitory Avoidance (IA)

The inhibitory avoidance task is used in mice to assess primarily amygdala-dependent learning (Blanchard and Blanchard, 1972; Phillips and LeDoux, 1992; Holahan and White, 2002). IA testing will consist of a training session followed by testing 1.5 and 24 hours post training During the training session, a mouse will be placed in a lightened chamber and when the mouse crosses to the dark compartment, it will receive a mild footshock (0.15 mA/1 s). During testing, the mouse will be placed again in the light compartment and the latency to cross over to the dark compartment will be measured. This latency measure will be used as an index of passive fear avoidance.

b. Biochemical Markers

A$\beta$ measurements: Quantitative data on the effects of compound on various species of A$\beta$ (e.g. A$\beta$40 versus A$\beta$P42; soluble versus insoluble A$\beta$) (Oddo et al, 2003). Protein extracted from brain tissue from mice treated with compound will be used to generate soluble and insoluble protein extracts and analyzed by sandwich ELISA. Western blots to measure steady state levels of the APP holoprotein, C99/C83 fragments, and sAPP$\beta$ to determine the effects of compound on these biomarkers will be performed. Enzymatic pathways which lead to production of A$\beta$, as well as enzymes known to degrade A$\beta$, will be looked at.

Tau hyperphosphorylation: Because the 3×Tg-AD mice accumulate argyrophilic and filamentous tau immunoreactive neuronal inclusions with increasing age in cortex and hippocampus (Oddo et al, 2003), we are able to evaluate the effects of compound on tau hyperphosphorylation as a functional biomarker. This will be accomplished with quantitative western blotting with antibodies (such as ATB, AT100, or PHF1) that specifically recognize hyperphosphorylated tau. Putative tau kinases and phosphatases will be looked at to see how treatment could be affecting tau phosphorylation.

c. Immunohistochemistry

To assess for total plaques and tangles and also microglial activation, 3×Tg-AD mouse brains will be paraformaldehyde-fixed and sectioned at 55 µM. Using various antibodies against various forms of A$\beta$ (1-40, 1-42 and oligomeric) and phosphorylated forms of tau, plaques and tangles can be visualized for location and severity within the brain. In addition antibodies against CD45 will stain for microglial activation to see if plaques and tangles still initiate an immune response. Changes in synaptic connections (PSD-95, synaptophysin etc.), and neuronal loss (NeuN, Fluorojade) will be also looked at.

Total animals required: 180 (with minimum 10-15 animals in each group).

Example 3

In Example 3, the safety and efficacy of an anti-$\Delta$ tau vaccine, an anti-$\Delta\beta$ vaccine and a combination anti-$\Delta$ and anti-A$\beta$ vaccine will be accessed. The anti-A tau vaccine will comprise an immunogenic peptide of SEQ ID NO. 116 (H2N-VDDALINSTKIYSYFPSVGPSLIDMVD-OH) and alum. The anti-A$\beta$ vaccine will comprise an immunogenic peptide of SEQ ID NO. 117 (H2N-DAEFGPSLVDDALINST-KIYSYFPSV-OH) and allum. The combination vaccine will comprise a mixture of the immunogenic peptides of SEQ ID NOS. 116 and 117, and alum. In these vaccines, alum will be used as adjuvant, and immunogenic peptides will be used active agents.

Each vaccine will be administered to a group of LaFerla mice (i.e., transgenic mice expressing 3 mutations relevant to Alzheimer's pathology (PS1$_{M146V}$, $\beta$APP$_{Swe}$, and tau$_{P301L}$)). There would also be a control group of mice which will not receive any vaccines containing peptides of SEQ ID NO: 116 or SEQ ID NO 117. The "vaccine" administered to the control group will comprise alum.

Behavioral studies will be conducted at 9 and 15 months, to access cognitive functions.

Blood levels of A$\beta$1-40, A$\beta$1-42, $\Delta$Tau, htau40, IgG, IgM, and cytokine profiles from the blood will be measured from 6 months to 9 months after an initial administration and, then, at 12 month, 15 months and 18 months after administration.

Imaging of amyloid plaques by AV-45-PET (Poisnel et al., AAICD, 2011) will be performed at 6 months, 12 months and 18 months, to access levels of amyloid pathology.

Brain metabolism will be accessed by FDG-PEG (analysis with input function taken from the heart of the animal) at 6 months, 12 months and 18 months, to access clinical efficacy.

MRI imaging will be performed at 6 months, 12 months and 18 months, to access degree of inflammation, anatomy, to detect development of any microhaemorrhages and/or any vasogenic edema, cerebral anrophy, and/or to follow-up on evolution of individual plaques.

Axonal transportation will be accessed at 6 and 18 months by MRI, to access the level of Tau and A$\beta$ pathology.

Plaque imaging will be performed at 6 and 18 months by MRI, using Gadolinium.

Three mice from each group, including a control group, will be sacrificed at 3 months, 9 months, 12 months, and 15 months, to access biomarkers of amyloid and tau pathologies. All mice will be sacrificies at 18 months, to access biomarkers of amyloid and tau pathology.

The generated data will be analyzed and, preferably, will confirm the efficacy and safety of the administered vaccines.

CONCLUSION

Having now fully described this invention, it will be appreciated by those skilled in the art that the same can be performed within a wide range of equivalent parameters, concentrations, and conditions without departing from the spirit and scope of the invention and without undue experimentation.

While this invention has been described in connection with specific embodiments thereof, it will be understood that it is capable of further modifications. This application is intended to cover any variations, uses, or adaptations of the inventions following, in general, the principles of the invention and including such departures from the present disclosure as come within known or customary practice within the art to which the invention pertains and as may be applied to the essential features hereinbefore set forth as follows in the scope of the appended claims. The person skilled in the art knows how to employ the methods of the present invention for a variety of different purposes which all fall within the scope of protection of the present invention.

All references cited herein, including journal articles or abstracts, published or unpublished U.S. or foreign patent applications, issued U.S. or foreign patents, or any other references, are entirely incorporated by reference herein, including all data, tables, figures, and text presented in the cited references. Additionally, the entire contents of the references cited within the references cited herein are also entirely incorporated by reference.

Reference to known method steps, conventional methods steps, known methods or conventional methods is not in any way an admission that any aspect, description or embodiment of the present invention is disclosed, taught or suggested in the relevant art.

The foregoing description of the specific embodiments will so fully reveal the general nature of the invention that others can, by applying knowledge within the skill of the art (including the contents of the references cited herein), readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one of ordinary skill in the art.

---

The invention claimed is:

1. A method of inhibiting tau polymerization in vivo, comprising administering to a human in need of therapy for Alzheimer's disease or other tauopathies an effective amount of free end-specific antibodies capable of selectively binding abnormal forms of tau proteins, said antibodies showing no reactivity and/or binding with a normal tau protein, and being administered under conditions and in an amount(s) effective to inhibit polymerization of tau in the brain of the human, wherein the abnormal forms of tau proteins are selected from the group consisting of hTau40 truncated at its C-terminus at the glutamic acid residue Glu391, hTau40 truncated at the aspartic acid residue Asp421, hTau40 truncated at its N-terminus at the aspartic acid residue Asp13, proteins homologous to hTau40 truncated at its C-terminus at the glutamic acid residue Glu391, proteins homologous to hTau40 truncated at the aspartic acid residue Asp421, and proteins homologous to hTau40 truncated at its N-terminus at the aspartic acid residue Asp13, the normal tau protein is a full length untruncated hTau40, and the antibodies specifically recognize a sequence out of SEQ ID NOs. 7-94 or 116 in a truncated hTau40 and bind the recognized sequence with equilibrium constant KD of from $1\times10^{-9}$ M to $1\times10^{-11}$ M, as measured by a surface plasmon resonance assay utilizing peptide captured on strepvidin chip, but do not recognize the same sequence of amino acids when present internally in hTau40.

2. The method of claim 1, wherein the truncated hTau40 is soluble.

3. The method of claim 2, wherein the antibodies are selective for soluble truncated tau (i) truncated at its C-terminus at the glutamic acid residue Glu391, or (ii) or at the aspartic acid residue Asp421, or (iii) truncated at its N-terminus at the aspartic acid residue Asp 13, or (iv) truncated at a combination of at positions (i)-(iii).

4. A method of inhibiting, reducing, clearing or eliminating tau truncated at the glutamic acid residue Glu391 or at the aspartic acid residue Asp421 or at the aspartic acid residue Asp13 in a living mammal comprising administering to the living mammal an antibody which is specific for the neoepitope created by truncation of tau at the glutamic acid residue Glu391 or at the aspartic acid residue Asp421 or at the aspartic acid residue Asp13, wherein the antibody specifically recognizes a sequence out of SEQ ID NOs. 7-94 or 116 in a truncated hTau40 and binds the recognized sequence with equilibrium constant KD of from $1\times10^{-9}$ M to $1\times10^{-11}$ M, but does not recognize the same sequence of amino acids when present internally in hTau40.

5. A method according to claim 4, wherein the neoepitope was created by cleavage of hTau40 at the aspartic acid residue Asp13.

6. The method of claim 4, wherein the antibody is specific for tau391-421, Tau395-421, Tau408-421, Tau361-391, or a fragment of any one of the foregoing, and shows no reactivity with htau40.

7. A method of inhibiting aggregation of tau in a mammal, the method comprising administering to the mammal an antibody which is specific for the neoepitope created by truncation of tau at the glutamic acid residue Glu391 or at the aspartic acid residue Asp421 or at the aspartic acid residue Asp13, wherein the antibody specifically recognizes a sequence out of SEQ ID NOs. 7-94 or 116 in a truncated hTau40 and binds the recognized sequence with equilibrium constant KD of from $1\times10^{-9}$ M to $1\times10^{-11}$ M, but does not recognize the same sequence of amino acids when present internally in hTau40.

8. A method of promoting clearance of aggregates from the brain of a human, comprising administering antibodies to a human in need of therapy for Alzheimer's disease or other tauopathies, the antibodies having specificity to Δ Tau, said antibodies showing no binding or reactivity with hTau40, and are administered under conditions and in an amount(s) effective to promote clearance of neurofibrillary tangles from the brain of the human, wherein the antibodies specifically recognize a sequence out of SEQ ID NOs. 78-86 or 116 or a sequence homologous to the sequence out of SEQ ID NOs. 78-86 or 116 in Δ Tau, but do not recognize the same sequence of amino acids when present internally in hTau40, provided that if the antibodies specifically recognize a sequence homologous to SEQ ID. NO. 84 or 85, the recognized sequence is not phosphorylated.

9. The method of claim 8, wherein the epitope of at least one of the antibodies comprises a sequence identical to or homologous with any one of SEQ ID NOs: 80-86 or 116.

10. The method of claim 8, wherein the epitope of the antibody consists of any one of SEQ ID NOs: 83-86 or 116.

11. The method of claim 9, wherein the epitope was created by cleavage of hTau40 at Asp421.

12. The method of claim 11, wherein the antibody binds the epitope with equilibrium constant KD of from $1\times10^{-9}$ M to $1\times10^{-11}$ M, as measured by a surface plasmon resonance assay utilizing peptide captured on strepvidin chip; and has an equilibrium constant KD with hTau40 which is from $1\times10^{-4}$ M to $1\times10^{-6}$ M, as measured by the surface plasmon resonance assay utilizing peptide captured on strepvidin chip, or shows no detectable binding with hTau40.

13. The method of claim 12, wherein the antibody shows no detectable binding with hTau40.

14. The method of claim 11, wherein at least one of the antibodies is TauC3.

15. The method of claim 11, wherein the tau protein is truncated at its N-terminus at the aspartic acid residue Asp13.

16. The method of claim 8, wherein at least one of the antibodies specifically binds to a synthetic peptide corresponding to amino acids 416-421 of Δ Tau.

17. A method of slowing progression of a tangle-related behavioral phenotype in a subject, comprising administering antibodies to a human in need of therapy for Alzheimer's disease or other tauopathies, the antibodies having specificity to abnormal forms of tau proteins and showing no binding and/or reactivity with a normal tau protein, the antibodies being administered under conditions and in an amount(s) effective to slow a tangle-related behavioral phenotype in a subject, wherein
the abnormal forms of tau proteins are selected from the group consisting of hTau40 truncated at its C-terminus at the glutamic acid residue Glu391, hTau40 truncated at the aspartic acid residue Asp421, hTau40 truncated at its N-terminus at the aspartic acid residue Asp13, proteins homologous to hTau40 truncated at its C-terminus at the glutamic acid residue Glu391, proteins homologous to hTau40 truncated at the aspartic acid residue Asp421, and proteins homologous to hTau40 truncated at its N-terminus at the aspartic acid residue Asp13,
the normal tau protein is a full length untruncated hTau40, the antibodies specifically recognize a sequence out of SEQ ID NOs. 7-94 or 116 or a sequence homologous to the a sequence out of SEQ ID NOs. 7-94 or 116 in the abnormal forms of tau proteins, but do not recognize the same sequence of amino acids when present internally in the normal tau protein.

18. The method of claim 17, wherein the antibodies bind at least one of the abnormal forms of tau proteins with equilibrium constant KD of from $1\times10^{-9}$ M to $1\times10^{-11}$ M, as measured by a surface plasmon resonance assay utilizing peptide captured on strepvidin chip.

19. The method of claim 17, wherein the abnormal forms of tau proteins are selected from the group consisting of hTau40 truncated at the aspartic acid residue Asp421 and hTau40 tau truncated at its N-terminus at the aspartic acid residue Asp13.

20. The method of claim 17, wherein the truncated hTau40 is soluble.

21. The method of claim 20, wherein at least one of the antibodies is able to recognize conformational free-end epitopes of the abnormal forms of tau proteins.

22. The method of claim 20, wherein at least one of the antibodies is able to recognize linear free-end epitopes of the abnormal forms of tau proteins.

23. The method of claim 22, wherein the antibodies are selective for a neoepitope created by cleavage of hTau40 at Asp421, the neoepitope consisting of an amino acid sequence consisting of any one of SEQ ID NOs. 75-86 or 116.

24. The method of claim 12, wherein the antibodies recognize, bind and show reactivity with Δ Tau, and do not recognize, bind or show reactivity with hTau40.

25. The method of claim 17, wherein the abnormal form of tau protein is hTau40 truncated at its C-terminus at the glutamic acid residue Glu391, and at least one of the antibodies is MN423.

26. The method of claim 19, wherein the abnormal form of tau protein is hTau40 truncated at its C-terminus at the aspartic acid residue Asp421 and at least one of the antibodies is TauC3.

27. The method of claim 19, wherein the abnormal form of tau protein is hTau40 truncated at its N-terminus at the aspartic acid residue Asp13.

28. The method of claim 19, wherein the antibodies specifically bind to the C-terminus of a synthetic peptide comprising a sequence of amino acids identical or homologous with any one of SEQ ID NOs: 78-86 or 116.

29. A method of slowing the progression or ameliorating the symptoms of Alzheimer's disease in a subject, comprising administering antibodies to a human in need of therapy for Alzheimer's disease, the antibodies having specificity to abnormal forms of tau proteins, said antibodies showing no binding and/or reactivity to a normal tau protein and being administered under conditions and in an amount(s) effective to slow the progression or ameliorate the symptoms of Alzheimer's disease, wherein
the abnormal forms of tau proteins are selected from the group consisting of hTau40 truncated at its C-terminus at the glutamic acid residue Glu391, hTau40 truncated at the aspartic acid residue Asp421, hTau40 truncated at its N-terminus at the aspartic acid residue Asp13, proteins homologous to hTau40 truncated at its C-terminus at the glutamic acid residue Glu391, proteins homologous to hTau40 truncated at the aspartic acid residue Asp421, and proteins homologous to hTau40 truncated at its N-terminus at the aspartic acid residue Asp13,
the normal tau protein is a full length untruncated hTau40, and
the antibodies specifically recognize a sequence out of SEQ ID NOs. 7-94 or 116 or a sequence homologous the sequence out of SEQ ID Nos. 7-94 or 116 in the abnormal forms of tau proteins, but do not recognize the same sequence of amino acids when present internally in the normal tau protein, provided that if the antibodies specifically recognize a sequence homologous to SEQ ID. NO. 84 or 85, the recognized sequence is not phosphorylated.

30. The method of claim 29, wherein the antibodies bind at least one of the abnormal forms of tau proteins with equilibrium constant KD of from $1 \times 10^{-9}$ M to $1 \times 10^{-11}$ M, as measured by a surface plasmon resonance assay utilizing peptide captured on strepvidin chip.

31. The method of claim 29, further comprising administering to the human one or more antibodies specific for the neoepitope created by cleavage of APP.

32. The method of claim 31, wherein the one or more antibodies specific for the neoepitope created by cleavage of APP is an antibody which is free end-specific for Aβ peptides selected from Aβ1-39, Aβ1-40, Aβ1-41, Aβ1-42, and Aβ1-43 and/or internal cleavage sites at positions 11 and 17 of any of the foregoing.

33. The method of claim 32, wherein the one or more antibodies specific for the neoepitope created by cleavage of APP is selected from a group consisting of bapineuzumab, ponezumab, gantenerumab, solaneszumab, MABT5102A and GSK933756.

34. The method of claim 29, wherein the antibodies are linear epitope free-end specific antibodies.

35. The method of claim 29, wherein the antibodies are conformation-specific antibodies.

36. The method of claim 29, wherein the antibodies only recognize, bind and show reactivity with the truncated hTau40, and do not recognize, bind or show reactivity with a the full length untruncated hTau40.

37. The method of claim 29, wherein the abnormal form of tau protein is hTau40 truncated at its N-terminus at the aspartic acid residue Asp13.

38. The method of claim 29, wherein at least one of the antibodies specifically binds to a synthetic peptide corresponding to amino acids 412-421, or a fragment thereof, of Δ Tau and does not recognize the sequence of the synthetic peptide when it is present internally in hTau40.

39. The method of claim 29, wherein the abnormal forms of tau proteins are selected from the group consisting of hTau40 truncated at the aspartic acid residue Asp421 and hTau40 truncated at its N-terminus at the aspartic acid residue Asp13.

40. The method of claim 39, wherein the truncated hTau40 is soluble.

41. The method of claim 40, wherein the antibodies are able to specifically recognize linear free-end specific epitopes of the abnormal forms of tau proteins.

42. The method of claim 41, wherein the antibodies are selective for soluble truncated hTau40 truncated at the aspartic acid residue Asp421.

43. The method of claim 41, wherein the abnormal form of tau protein is hTau40 truncated at its C-terminus at the glutamic acid residue Glu391, and at least one of the antibodies is MN423.

44. The method of claim 41, wherein the abnormal form of tau protein is hTau40 truncated at its C-terminus at the aspartic acid residue Asp421, and at least one of the antibodies is TauC3.

* * * * *